(12) United States Patent
Coe et al.

(10) Patent No.: US 7,241,887 B2
(45) Date of Patent: Jul. 10, 2007

(54) 3-AZABICYCLO[3.2.1]OCTANE DERIVATIVES

(75) Inventors: Jotham W. Coe, Niantic, CT (US); Stanton McHardy, Coventry, RI (US); Crystal G. Bashore, New London, CT (US)

(73) Assignee: Pfizer Inc, New York, NY (US)

( * ) Notice: Subject to any disclaimer, the term of this patent is extended or adjusted under 35 U.S.C. 154(b) by 474 days.

(21) Appl. No.: 10/824,037

(22) Filed: Apr. 14, 2004

(65) Prior Publication Data

US 2004/0259859 A1  Dec. 23, 2004

Related U.S. Application Data

(60) Provisional application No. 60/462,629, filed on Apr. 14, 2003.

(51) Int. Cl.
*C07D 223/00* (2006.01)
*A01N 43/00* (2006.01)
*A61K 31/55* (2006.01)

(52) U.S. Cl. .................. 540/581; 540/585; 514/214.03
(58) Field of Classification Search ................ 540/582, 540/585, 581; 514/214.03
See application file for complete search history.

(56) References Cited

U.S. PATENT DOCUMENTS

| | | | |
|---|---|---|---|
| 5,250,542 A | 10/1993 | Cantrell et al. | 514/315 |
| 6,235,750 B1 | 5/2001 | Lowe, III | 514/299 |
| 6,313,312 B1 | 11/2001 | Banks et al. | 548/452 |
| 6,441,000 B1 | 8/2002 | Gibson et al. | 514/322 |
| 6,479,516 B1 | 11/2002 | Gibson et al. | 514/317 |
| 6,518,282 B1 | 2/2003 | Gibson et al. | 514/317 |
| 6,605,600 B1 | 8/2003 | Ensinger et al. | 514/81 |
| 6,610,711 B2 | 8/2003 | Armer et al. | 514/331 |
| 6,750,231 B2 | 6/2004 | Gibson et al. | 514/326 |
| 6,812,236 B2 | 11/2004 | Gibson et al. | 514/317 |
| 7,049,335 B2 | 5/2006 | McHardy et al. | 514/412 |
| 7,049,444 B2 | 5/2006 | Banks et al. | 458/452 |
| 7,056,930 B2 | 6/2006 | Coe et al. | 514/299 |
| 2002/0099214 A1 | 7/2002 | Gibson et al. | |
| 2003/0207876 A1 | 11/2003 | Banks et al. | |
| 2004/0259859 A1 | 12/2004 | Coe et al. | |
| 2005/0032837 A1 | 2/2005 | McHardy et al. | |

OTHER PUBLICATIONS

Kim et al., J. Med. Chem., 2003, "Synthesis and pharmacology of site specific cocaine abuse treatment agents: 8-substituted isotropane (3-Azabicyclo[3.2.1]octane) Dopamine uptake", vol. 46, pp. 1456-1464.*

Zhou et al., Yaoxue Xuebao, 1982, "Synthesis and analgesic activity of azabicycloalkanes derivatives", vol. 17, pp. 503-509.*

Kim, Deog-III, et al., "Synthesis and Pharmacology of Site Cocaine Abuse Treatment Agents: 8-Substituted Isotropane (3-Azabicyclo[3.2.1]octane0 Dopamine Uptake Inhibitors", *J. Med. Chem*, vol. 46, pp. 1456-1464 (2003).

Zhou, Dehe, et al., "Synthesis and Analgesic Activity of Azabicycloalkanes Derivatives", *Acta Pharmaceutica Sinica*, vol. 17, No. 7, pp. 503-509 (1982).

* cited by examiner

*Primary Examiner*—Margaret D. Seaman
*Assistant Examiner*—Niloofar Rahmani
(74) *Attorney, Agent, or Firm*—Gregg C. Benson; Arlene K. Musser

(57) ABSTRACT

The subject invention relates to 3-azabicyclo[3.2.1]octane derivatives, pharmaceutical compositions comprising such derivatives and methods of using such derivatives to treat disease states, disorders and conditions mediated by opioid receptors. The subject invention also particularly relates to using such derivatives to treat certain disorders and conditions, for example irritable bowel syndrome, drug addiction, depression, anxiety, schizophrenia and eating disorders, among others.

8 Claims, No Drawings

3-AZABICYCLO[3.2.1]OCTANE DERIVATIVES

This application claims priority under 35 U.S.C. 119(e) of U.S. Provisional 60/462,629, filed Apr. 14, 2003. The entire contents of the prior application U.S. Provisional 60/462,629 is incorporated herein by reference.

FIELD OF THE INVENTION

The subject invention relates to 3-azabicyclo[3.2.1]octane derivatives, pharmaceutical compositions comprising such derivatives and methods of using such derivatives to treat disease states, disorders and conditions mediated by opioid receptors. The subject invention also particularly relates to using such derivatives to treat certain disorders and conditions, for example irritable bowel syndrome, drug addiction, including alcohol addiction, depression, anxiety, schizophrenia and eating disorders, among others as will be more fully described herein.

BACKGROUND OF THE INVENTION

The compounds of the subject invention bind to opioid receptors (e.g. mu, kappa and delta opioid receptors). Compounds that bind to such receptors are likely to be useful in the treatment of diseases modulated by opioid receptors, for example irritable bowel syndrome; constipation; nausea; vomiting; and pruritic dermatoses, such as allergic dermatitis and atopy in animals and humans. Compounds that bind to opioid receptors have also been indicated in the treatment of eating disorders, opioid overdoses, depression, anxiety, schizophrenia, alcohol addiction, including alcohol abuse and dependency, sexual dysfunction, shock, stroke, spinal damage and head trauma.

Certain 4-arylpiperidine-based compounds are disclosed in European patent applications EP 287339, EP 506468 and EP 506478 as opioid receptor binding agents. In addition, International Patent Application WO 95/15327 discloses azabicycloalkane derivatives useful as neuroleptic agents. 3-Azabicyclo[3.1.0]hexane derivatives useful as opioid receptor agents are also disclosed in WO 00/39089.

SUMMARY OF THE INVENTION

The subject invention is directed to compounds of formula I:

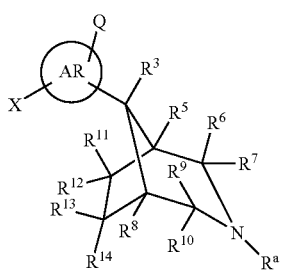

I wherein $R^a$ is H or a

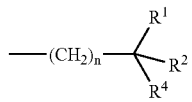

group;

is an aryl or heteroaryl group;

X is H, halogen, —OH, —CN, —C≡C—$R^{3a}$, a —$C_1$–$C_4$ alkyl group optionally substituted with from one to three halogen atoms, or a —O($C_1$–$C_4$ alkyl) group optionally substituted with from one to three halogen atoms;

Q is H, halogen, a $C_1$–$C_6$ alkyl, —OH, —CN, —OCH$_3$, —NH$_2$, —NH($C_1$–$C_4$ alkyl), —N($C_1$–$C_4$ alkyl)($C_1$–$C_4$ alkyl), —C(=O)NH$_2$, —C(=O)NH($C_1$–$C_4$ alkyl), —C(=O)N($C_1$–$C_4$ alkyl)($C_1$–$C_4$ alkyl), —NHC(=O)$R^{15}$, —NHS(=O)$_2 R^{15}$, a 5- to 7-membered carbocyclic or heterocyclic group, or forms a 5- to 7-membered phenyl-fused or heteroaryl-fused carbocyclic or heterocyclic group with an adjacent atom on the phenyl or heteroaryl group to which it is attached, said phenyl-fused or heteroaryl-fused carbocyclic or heterocyclic group optionally containing at least one unsaturated bond, said heterocyclic group or said phenyl-fused or heteroaryl-fused heterocyclic group containing at least one heteroatom selected from nitrogen, oxygen and sulfur, said carbocyclic or heterocyclic group or said phenyl- or heteroaryl-fused carbocyclic or heterocyclic group being optionally substituted with at least one substituent selected from H, halogen, —OH, =O, C≡C—$R^{3a}$, $C_1$–$C_6$ alkyl, —O($C_1$–$C_6$)alkyl, $C_3$–$C_6$ cycloalkyl, or —(CH$_2$)$_n$-aryl, wherein said $C_1$–$C_6$ alkyl, —O($C_1$–$C_6$)alkyl, or $C_3$–$C_6$ cycloalkyl groups optionally may be substituted by one or more halogen atoms and said aryl portion of said —(CH$_2$)$_n$-aryl is optionally substituted by one or more substituents selected from H, halogen, $C_1$–$C_4$ alkyl and —O($C_1$–$C_4$)alkyl, said $C_1$–$C_4$ alkyl and —O($C_1$–$C_4$)alkyl groups being optionally substituted by one or more halogen atoms, —N($R^{4a}$)($R^{5a}$), —N($R^{4b}$)S(O)$_m R^{6a}$, —N($R^{4c}$)C(O)$R^{7a}$ or —N($R^{4d}$)C(O)O$R^{7b}$ groups;

$R^{3a}$, $R^{4a}$, $R^{4b}$, $R^{4c}$, $R^{4d}$ and $R^{5a}$ are independently H or $C_1$–$C_6$ alkyl which may be optionally substituted with one or more halogen groups, or $R^{4a}$ and $R^{5a}$, together with the nitrogen atom to which they are bound, form a 4- to 7-membered heterocyclic group which may be unsubstituted or substituted with one or more substituents selected from $C_1$–$C_4$ alkyl, —O($C_1$–$C_4$)alkyl, —OH, =O, —NR$^{16a}$R$^{16b}$, halogen or —C≡C—$R^{3a}$;

$R^{6a}$ is a $C_1$–$C_6$ alkyl, an aryl or a heteroaryl group wherein said alkyl, aryl or heteroaryl group is unsubstituted or substituted with one or more substituents selected from halogen, $C_1$–$C_4$ alkyl, —OH, —O($C_1$–$C_4$ alkyl), —($C_1$–$C_4$ alkyl)-O—($C_1$–$C_4$ alkyl) or —(CH$_2$)$_n$—NR$^{21}$R$^{22}$;

$R^{7a}$ and $R^{7b}$ are independently selected from $C_1$–$C_6$ alkyl, $C_3$–$C_6$ cycloalkyl, and aryl (wherein each of said $C_1$–$C_6$ alkyl, $C_3$–$C_6$ cycloalkyl, and aryl may independently be unsubstituted or substituted with halogen or $C_1$–$C_4$ alkyl substituents), or $R^{7a}$ is H;

R$^1$ and R$^2$ are independently H, a C$_1$–C$_6$ alkyl, —(CH$_2$)$_j$-aryl, —(CH$_2$)$_j$-heteroary, wherein said alkyl, —(CH$_2$)$_j$-aryl or —(CH$_2$)$_j$-heteroaryl group is optionally substituted with one or more R$^{16}$ groups, or with the carbon to which R$^1$ and R$^2$ are attached, R$^1$ and R$^2$ form a C$_3$–C$_7$ carbocyclic or 4- to 7-membered heterocyclic group, wherein said heterocyclic group comprises from one to three heteroatoms selected from the group consisting of O, S and N and said carbocyclic or heterocyclic group optionally contains a —C(=O) group or optionally contains one or more double bonds and is optionally fused to or substituted with a C$_6$–C$_{14}$ aryl or a 5- to 14-membered heteroaryl group, wherein said C$_3$–C$_7$ carbocyclic or 4- to 7-membered heterocyclic group formed by R$^1$ and R$^2$ may optionally be substituted with from one to three R$^{16}$ groups, and said optionally fused or substituted aryl or heteroaryl group may each optionally independently be substituted with from one to six R$^{16}$ groups;

each R$^{16}$ is independently selected from R$^{17}$, H, halogen, —OR$^{17}$, —NO$_2$, —CN, —C$_1$–C$_6$ alkyl, —C$_3$–C$_6$ cycloalkyl, —C(R$^4$)R$^{16a}$R$^{16b}$, aryl optionally substituted with from 1 to 3 R$^4$ groups, —(CH$_2$)$_v$NR$^{17}$R$^{18}$, —NR$^{17}$C (=O)R$^{18}$, —C(=O)NR$^{17}$R$^{18}$, —OC(=O)R$^{17}$, —C(=O) OR$^{17}$, —C(=O)R$^{17}$, —NR$^{17}$C(=O)OR$^{18}$, —NR$^{17}$C (=O)N R$^{18}$R$^{19}$, —NR$^{17}$S(=O)$_2$R$^{18}$, —NR$^{17}$S(=O)$_2$NR$^{18}$R$^{19}$, and —S(=O)$_2$R$^{17}$;

R$^3$ is H, F, Cl, —OH, —C$_1$–C$_4$ alkyl, —C≡N, —NR$^{17}$C (=O)R$^{18}$, —C(=O)NR$^{17}$R$^{18}$, —O(C$_1$–C$_4$)alkyl, —(CH$_2$)$_n$OH, —(CH$_2$)$_n$—C≡N, —(CH$_2$)$_n$—NR$^{17}$C(=O) R$^{18}$, —(CH$_2$)$_n$—C(=O)NR$^{17}$R$^{18}$, —(CH$_2$)$_n$—O(C$_1$–C$_4$) alkyl, or —(CH$_2$)$_n$—NR$^{16a}$R$^{16b}$;

R$^4$ is absent or is H, —C$_1$–C$_4$ alkyl, which optionally contains one or two unsaturated bonds, —OH, —O(C$_1$–C$_4$) alkyl, —(C$_1$–C$_4$)alkylOH, —(CH$_2$)$_n$—NR$^{16a}$R$^{16b}$, —(CH$_2$)$_n$—NHC(=O)(C$_1$–C$_4$ alkyl), —(CH$_2$)$_n$—NO$_2$, —(CH$_2$)$_n$—C≡N, —(CH$_2$)$_n$—C(=O)NH$_2$, —(CH$_2$)$_n$—C (=O)NR$^{16a}$R$^{16b}$;

R$^5$ and R$^8$ are independently selected from H, Cl, F, —OH, C$_1$–C$_4$ alkyl, —O(C$_1$–C$_4$)alkyl, —C(=O)R$^{20}$, —(C$_1$–C$_4$ alkyl)-OR$^{20}$, —C(=O)OR$^{20}$, —OC(=O)R$^{20}$, —S(O)$_m$R$^{20}$ and —NHSO$_2$(C$_1$–C$_4$)alkyl;

R$^6$, R$^7$, R$^9$, R$^{10}$, R$^{11}$, R$^{12}$, R$^{13}$ and R$^{14}$ are each independently selected from H, F, Cl, —OH, —(C$_1$–C$_4$)alkyl and —O(C$_1$–C$_4$)alkyl;

R$^{15}$, R$^{17}$, R$^{18}$ and R$^{19}$ are independently H, —C$_1$–C$_4$ alkyl, —(C$_2$–C$_4$ alkyl)-O—(C$_1$–C$_4$ alkyl), —(CH$_2$)$_v$— NR$^{21}$R$^{22}$, or a 4- to 7-membered heterocyclic group optionally substituted with a —C$_1$–C$_4$ alkyl;

each R$^{16a}$ and R$^{16b}$ is independently selected from H and C$_1$–C$_4$ alkyl; or, independently in each instance of —C(R$^4$) R$^{16a}$R$^{16b}$, R$^{16a}$ and R$^{16b}$ connect to form a C$_3$–C$_7$ carbocyclic ring;

R$^{20}$ is a C$_1$–C$_4$ alkyl group, a C$_3$–C$_7$ carbocyclic or a 4- to 7-membered heterocyclic group comprising from one to three heteroatoms selected from the group consisting of O, S and N, wherein said carbocyclic and heterocyclic groups are optionally independently substituted with from one to three R$^{16}$ groups, optionally independently contain one or more double bonds, and are optionally fused to a C$_6$–C$_{14}$ aryl or a C$_5$–C$_{14}$ heteroaryl group comprising from one to three heteroatoms selected from the group consisting of O, S and N, and wherein said optionally fused aryl or heteroaryl groups can each optionally independently be substituted with from one to six R$^{16}$ groups;

R$^{21}$ and R$^{22}$ are each independently H or C$_1$–C$_6$ alkyl; or, independently in each instance of —NR$^{21}$R$^{22}$, R$^{21}$ and R$^{22}$ connect to form a 4- to 7-membered heterocyclic ring comprising from one to three hetero atoms selected from O, S, and N;

j is in each instance independently an integer from 0 to 5;

m is in each instance independently an integer from 0 to 2;

n is in each instance independently an integer from 0 to 5;

v is in each instance independently an integer from 0 to 5;

and pharmaceutically acceptable salts thereof;

with the provisos that a) when R$^a$ is

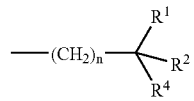

and n is 0, and when the carbon to which R$^1$, R$^2$ and R$^4$ are bound is sp$^3$ hybridized (i.e., "saturated"), then none of R$^1$, R$^2$ and R$^4$ can be a heteroatom or contain a heteroatom which is directly linked to the carbon of said

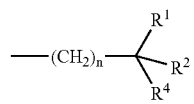

group;

b) R$^{15}$ cannot be H when part of a —NHS(=O)$_2$R$^{15}$ group, R$^{17}$ cannot be H when part of a —S(=O)$_2$R$^{17}$ group and R$^{18}$ cannot be H when part of a —NR$^{17}$S(=O)$_2$R$^{18}$ group;

c) when R$^3$ is OCH$_3$ or OH,

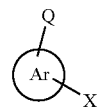

cannot be 3-hydroxyphenyl or 3-methoxyphenyl;

d) when

is a phenyl group, then Q and X are not both H;

e) when —(CH$_2$)$_v$— is connected to N, O, or S, then v cannot be 1; and f)

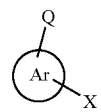

cannot be 4-(6-amino-pyridin-2-yl)-phenyl.

The subject invention also is directed to therapeutic methods and pharmaceutical compositions, as described in further detail below, comprising administration to a mammal of a compound of formula I.

Preferred embodiments of the subject invention include compounds according to formula 1, above, wherein Q is —C(=O)NH$_2$, —OH, or —NHSO$_2$R$^{15}$, most preferably —C(=O)NH$_2$ or —NHSO$_2$R$^{15}$ wherein R$^{15}$ is CH$_3$, —(CH$_2$)$_2$—O—CH$_3$, or -4-(1-methylimidazole).

In the subject invention, preferred compounds also include those wherein (AR)

is aryl, more preferably a phenyl group. Preferably (AR)

is phenyl and Q is substituted at a meta position on said phenyl group. In more preferred embodiments, (AR)

is phenyl, Q is substituted at a meta position on said phenyl group, and Q is selected from —C(=O)NH$_2$, —OH, and —NHSO$_2$R$^{15}$, most preferably —C(=O)NH$_2$ or —NHSO$^2$R$^{15}$ wherein R$^{15}$ is CH$_3$ or —(CH$_2$)$_2$—O—CH$_3$.

In other preferred embodiments;

(AR)

is phenyl; Q is substituted at a meta position on said phenyl group; and X is selected from H, F and C≡N. In other preferred embodiments;

(AR)

is phenyl; Q is substituted at a meta position on said phenyl group and is selected from —C(=O)NH$_2$, —OH, and —NHSO$_2$R$^{15}$; and X is selected from H, F and C≡N. In certain preferred compounds of the subject invention, when Q forms a phenyl-fused heterocyclic group with the adjacent phenyl group, said Q group and said phenyl group together may form a group according to the chemical structure:

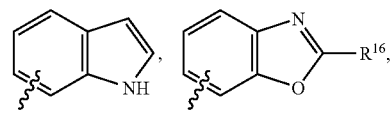

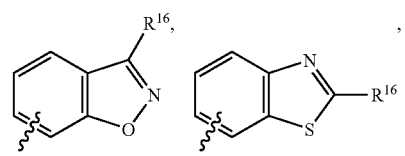

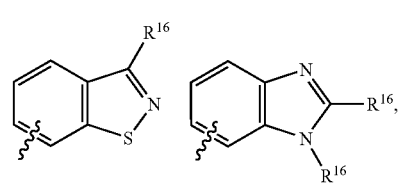

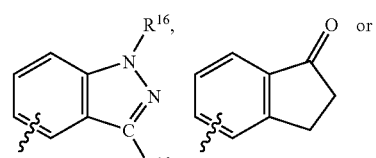

In still further aspects of the present invention, R$^1$ and R$^2$ taken together with the carbon to which they are attached, are preferably selected from cyclobutane, cyclopentane, cyclohexane, indane-2-yl, 1,2,3,4-Tetrahydronaphth-2-yl, wherein each may be substituted with R$^{16}$ groups as previously described.

In other preferred embodiments, R$^3$ is H, OH, Cl, methyl, ethyl, isopropyl, OMe, OEt, O-iPr, O-allyl or O-n-Pr.

In other preferred embodiments, R$^4$ is H, OH, —NH(=O)—CH$_3$, —C(=O)NH$_2$, —CH$_2$OH or OCH$_3$, more preferably OH.

In still further preferred aspects of the present invention, R$^5$, R$^6$, R$^7$, R$^8$, R$^9$, R$^{10}$, R$^{11}$, R$^{12}$, R$^{13}$ and R$^{14}$ are H. In such embodiments, R$^{15}$ is preferably CH$_3$ or —(CH$_2$)$_2$—O—CH$_3$.

Further preferred embodiments of the subject invention are compounds according to the following formula II and therapeutic methods and pharmaceutical composition comprising use of such compounds:

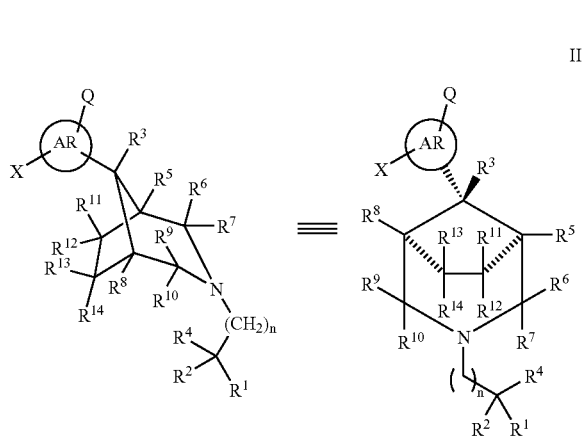

In formula II, each of the substituents is as presented hereinabove for compounds of formula I. Note that the above depictions of formula II represent identical chemical structures of formula II and are used herein for reference and to provide alternative displays of the same relative stereochemistry of the

and $R^3$ groups.

In more preferred embodiments of the subject invention, in the above formula II,

is preferably a phenyl group. In other preferred embodiments in the above formula II, Q is preferably substituted at a meta position of the phenyl group. In such embodiments of the invention according to formula II wherein

is a phenyl group substituted by Q at the meta position, Q is preferably —C(=O)NH$_2$, OH or —NHSO$_2$R$^{15}$. In still other preferred embodiments of the invention according to formula II wherein

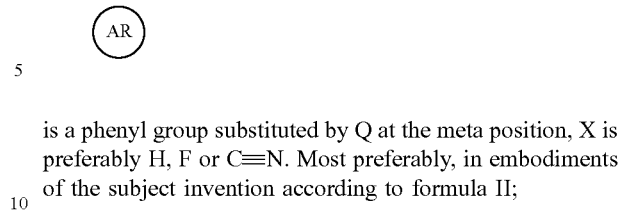

is a phenyl group substituted by Q at the meta position, X is preferably H, F or C≡N. Most preferably, in embodiments of the subject invention according to formula II;

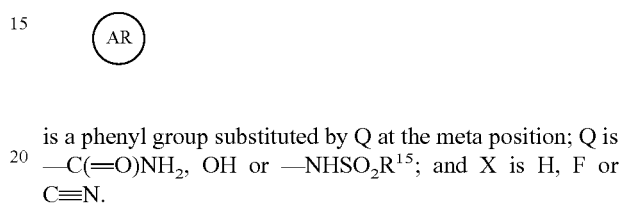

is a phenyl group substituted by Q at the meta position; Q is —C(=O)NH$_2$, OH or —NHSO$_2$R$^{15}$; and X is H, F or C≡N.

Preferred embodiments of the invention also include compounds, and therapeutic methods and pharmaceutical compositions comprising such compounds, wherein

is a phenyl group; Q is substituted at a meta position on said phenyl group and is selected from —C(=O)NH$_2$, —OH and —NHSO$_2$R$^{15}$; R$^a$ is a

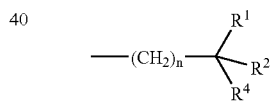

group; and R$^1$ and R$^2$ taken together with the carbon to which they are attached form a cyclobutane, cyclopentane, cyclohexane, indane-2-yl or 1,2,3,4-tetrahydronaphth-2-yl which may be unsubstituted or substituted with R$^{16}$ groups as described above. In such embodiments, R$^4$ is more preferably H, —OH, —NH(=O)—CH$_3$, —C(=O)NH$_2$, —CH$_2$OH or —OCH$_3$. Most preferably in such embodiments R$^4$ is OH.

In other preferred embodiments according to the present invention, R$^a$ is

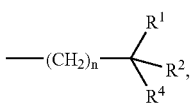

and n is 1–3, more preferably 1.

In the compounds, therapeutic methods, and pharmaceutical compositions of the subject invention, the following chemical formula III is more preferred:

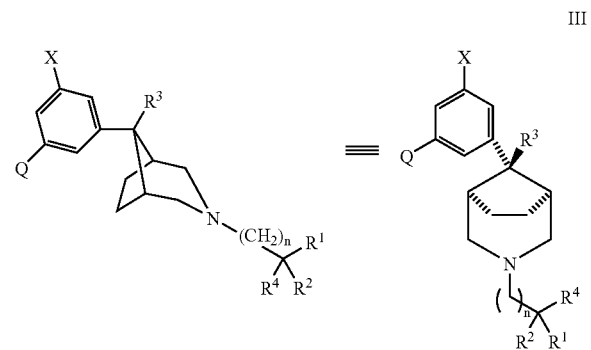

wherein Q, X, R¹, R², R³, R⁴ and n are the same as described above and the two depictions of formula III above are equivalent (identical) chemical structures which are used to indicate the relative stereochemistry of the phenyl group and the R³ group in the compound.

In the subject invention, the following compounds of formula I are also preferred:

3-(3-Cyclopropylmethyl-3-aza-bicyclo[3.2.1]oct-8-yl)-phenol;
3-(3-Ethyl-8-methoxy-3-aza-bicyclo[3.2.1]oct-8-yl)-benzamide;
3-(3-Cyclopropylmethyl-8-methoxy-3-aza-bicyclo[3.2.1]oct-8-yl)-benzamide;
3-[3-(3-Cyclohexyl-propyl)-3-aza-bicyclo[3.2.1]oct-8-yl]-phenol;
3-[8-Methoxy-3-(3-methyl-butyl)-3-aza-bicyclo[3.2.1]oct-8-yl]-benzamide;
3-(8-Methoxy-3-pentyl-3-aza-bicyclo[3.2.1]oct-8-yl)-benzamide;
3-[8-Methoxy-3-(1H-pyrrol-2-ylmethyl)-3-aza-bicyclo[3.2.1]oct-8-yl]-benzamide;
3-(3-Hexyl-8-methoxy-3-aza-bicyclo[3.2.1]oct-8-yl)-benzamide;
3-[3-(2-Ethyl-butyl)-8-methoxy-3-aza-bicyclo[3.2.1]oct-8-yl]-benzamide;
2-[8-(3-Hydroxy-phenyl)-3-aza-bicyclo[3.2.1]oct-3-ylmethyl]-indan-2-ol;
3-[8-Methoxy-3-(1-methyl-1H-pyrrol-2-ylmethyl)-3-aza-bicyclo[3.2.1]oct-8-yl]-benzamide;
3-(8-Methoxy-3-thiophen-3-ylmethyl-3-aza-bicyclo[3.2.1]oct-8-yl)-benzamide;
3-(8-Methoxy-3-thiazol-2-ylmethyl-3-aza-bicyclo[3.2.1]oct-8-yl)-benzamide;
3-[3-(1-Hydroxy-cyclohexyl)-propyl]-8-(3-hydroxy-phenyl)-3-aza-bicyclo[3.2.1]octan-8-ol;
N-[3-(3-Cyclopropylmethyl-8-methoxy-3-aza-bicyclo[3.2.1]oct-8-yl)-phenyl]-methanesulfonamide;
3-(8-Methoxy-3-phenethyl-3-aza-bicyclo[3.2.1]oct-8-yl)-benzamide;
3-(2-Hydroxy-indan-2-ylmethyl)-8-(3-hydroxy-phenyl)-3-aza-bicyclo[3.2.1]octan-8-ol;
N-[3-(3-Isobutyl-8-methoxy-3-aza-bicyclo[3.2.1]oct-8-yl)-phenyl]-methanesulfonamide;
3-(8-Methoxy-3-octyl-3-aza-bicyclo[3.2.1]oct-8-yl)-benzamide;
3-{3-[3-(1-Hydroxy-cyclohexyl)-propyl]-8-methoxy-3-aza-[3.2.1]oct-8-yl}-phenol;

3-[8-Methoxy-3-(3-phenyl-prop-2-ynyl)-3-aza-bicyclo[3.2.1]oct-8-yl]-benzamide;
3-[8-Methoxy-3-(3-phenyl-propyl)-3-aza-bicyclo[3.2.1]oct-8-yl]-benzamide;
2-[8-(3-Hydroxy-phenyl)-8-methoxy-3-aza-bicyclo[3.2.1]oct-3-ylmethyl]-indan-2-ol;
N-{3-[8-Methoxy-3-(3-methyl-butyl)-3-aza-bicyclo[3.2.1]oct-8-yl]-phenyl}-methanesulfonamide;
N-[3-(8-Methoxy-3-pentyl-3-aza-bicyclo[3.2.1]oct-8-yl)-phenyl]-methanesulfonamide;
3-[3-(1H-Indol-3-ylmethyl)-8-methoxy-3-aza-bicyclo[3.2.1]oct-8-yl]-benzamide;
3-(3-Benzofuran-2-ylmethyl-8-methoxy-3-aza-bicyclo[3.2.1]oct-8-yl)-benzamide;
3-[3-(2-Hydroxy-1,2,3,4-tetrahydro-naphthalen-2-ylmethyl)-3-aza-bicyclo[3.2.1]oct-8-yl]-benzamide;
N-{3-[3-(2-Ethyl-butyl)-8-methoxy-3-aza-bicyclo[3.2.1]oct-8-yl]-phenyl}-methanesulfonamide;
N-[3-(3-Hexyl-8-methoxy-3-aza-bicyclo[3.2.1]oct-8-yl)-phenyl]-methanesulfonamide;
3-(8-Methoxy-3-naphthalen-2-ylmethyl-3-aza-bicyclo[3.2.1]oct-8-yl)-benzamide;
3-{3-[3-(1-Hydroxy-cyclohexyl)-propyl]-8-methoxy-3-aza-bicyclo[3.2.1]oct-8-yl}-benzamide;
3-(8-Methoxy-3-quinolin-3-ylmethyl-3-aza-bicyclo[3.2.1]oct-8-yl)-benzamide;
N-[3-(8-Methoxy-3-pyridin-3-ylmethyl-3-aza-bicyclo[3.2.1]oct-8-yl)-phenyl]-methanesulfonamide;
3-[3-(4-Chloro-2-fluoro-benzyl)-8-methoxy-3-aza-bicyclo[3.2.1]oct-8-yl]-benzamide;
3-[8-Methoxy-3-(1-methyl-1H-indol-3-ylmethyl)-3-aza-bicyclo[3.2.1]oct-8-yl]-benzamide;
3-[3-(2-Hydroxy-1,2,3,4-tetrahydro-naphthalen-2-ylmethyl)-8-hydroxy-3-aza-bicyclo[3.2.1]oct-8-yl]-benzamide;
3-[3-(2-Hydroxy-indan-2-ylmethyl)-8-methoxy-3-aza-bicyclo[3.2.1]oct-8-yl]-benzamide;
N-[3-(8-Methoxy-3-thiazol-2-ylmethyl-3-aza-bicyclo[3.2.1]oct-8-yl)-phenyl]-methanesulfonamide;
3-[8-Methoxy-3-(2-phenethyloxy-ethyl)-3-aza-bicyclo[3.2.1]oct-8-yl]-benzamide;
N-[3-(3-Heptyl-8-methoxy-3-aza-bicyclo[3.2.1]oct-8-yl)-phenyl]-methanesulfonamide;
2-Methoxy-ethanesulfonic acid [3-(8-hydroxy-3-pentyl-3-aza-bicyclo[3.2.1]oct-8-yl)-phenyl]-amide;
2-Methoxy-ethanesulfonic acid {3-[8-hydroxy-3-(3-methyl-butyl)-3-aza-bicyclo[3.2.1]oct-8-yl]-phenyl}-amide;
N-[3-(8-Methoxy-3-phenethyl-3-aza-bicyclo[3.2.1]oct-8-yl)-phenyl]-methanesulfonamide;
3-[3-(4-Hydroxy-naphthalen-1-ylmethyl)-8-methoxy-3-aza-bicyclo[3.2.1]oct-8-yl]-benzamide;
N-{3-[3-(4-Fluoro-benzyl)-8-methoxy-3-aza-bicyclo[3.2.1]oct-8-yl]-phenyl}-methanesulfonamide;
3-[8-Methoxy-3-(4-pyrrol idin-1-yl-benzyl)-3-aza-bicyclo[3.2.1]oct-8-yl]-benzamide;
3-[8-Methoxy-3-(3-methyl-benzo[b]thiophen-2-ylmethyl)-3-aza-bicyclo[3.2.1]oct-8-yl]-benzamide;
3-[3-(2-Hydroxy-1,2,3,4-tetrahydro-naphthalen-2-ylmethyl)-8-methoxy-3-aza-bicyclo[3.2.1]oct-8-yl]-benzamide;
3-[3-(1-Hydroxy-3-phenyl-cyclobutylmethyl)-8-methoxy-3-aza-bicyclo[3.2.1]oct-8-yl]-benzamide;
N-{3-[3-(2-Ethyl-hexyl)-8-methoxy-3-aza-bicyclo[3.2.1]oct-8-yl]-phenyl}-methanesulfonamide;
N-[3-(8-Methoxy-3-octyl-3-aza-bicyclo[3.2.1]oct-8-yl)-phenyl]-methanesulfonamide;

2-Methoxy-ethanesulfonic acid [3-(3-hexyl-8-hydroxy-3-aza-bicyclo[3.2.1]oct-8-yl)-phenyl]-amide;
3-(3-Biphenyl-4-ylmethyl-8-methoxy-3-aza-bicyclo[3.2.1]oct-8-yl)-benzamide;
N-{3-[3-(2-Hydroxy-indan-2-ylmethyl)-3-aza-bicyclo[3.2.1]oct-8-yl]-phenyl}-methanesulfonamide;
N-{3-[8-Methoxy-3-(4-methoxy-benzyl)-3-aza-bicyclo[3.2.1]oct-8-yl]-phenyl}-methanesulfonamide;
2-Methoxy-ethanesulfonic acid [3-(8-hydroxy-3-pyridin-3-ylmethyl-3-aza-bicyclo[3.2.1]oct-8-yl)-phenyl]-amide;
3-[8-Methoxy-3-(3-trifluoromethoxy-benzyl)-3-aza-bicyclo[3.2.1]oct-8-yl]-benzamide;
N-{3-[3-(4-Chloro-benzyl)-8-methoxy-3-aza-bicyclo[3.2.1]oct-8-yl]-phenyl}-methanesulfonamide;
2-Methoxy-ethanesulfonic acid [3-(8-hydroxy-3-thiophen-3-ylmethyl-3-aza-bicyclo[3.2.1]oct-8-yl)-phenyl]-amide;
2-Methoxy-ethanesulfonic acid [3-(3-cyclohexylmethyl-8-hydroxy-3-aza-bicyclo[3.2.1]oct-8-yl)-phenyl]-amide;
N-(3-{8-Hydroxy-3-[3-(1-hydroxy-cyclohexyl)-propyl]-3-aza-bicyclo[3.2.1]oct-8-yl -phenyl)-methanesulfonamide;
3-[3-(9H-Fluoren-2-ylmethyl)-8-methoxy-3-aza-bicyclo[3.2.1]oct-8-yl]-benzamide;
N-{3-[3-(1H-Indol-3-ylmethyl)-8-methoxy-3-aza-bicyclo[3.2.1]oct-8-yl]-phenyl}-methanesulfonamide;
N-[3-(3-Benzofuran-2-ylmethyl-8-methoxy-3-aza-bicyclo[3.2.1]oct-8-yl)-phenyl]-methanesulfonamide;
N-{3-[3-(2-Hydroxy-1,2,3,4-tetrahydro-naphthalen-2-ylmethyl)-3-aza-bicyclo[3.2.1]oct-8-yl]-phenyl}-methanesulfonamide;
3-[8-Methoxy-3-(3-phenoxy-benzyl)-3-aza-bicyclo[3.2.1]oct-8-yl]-benzamide;
N-{3-[8-Hydroxy-3-(2-hydroxy-indan-2-ylmethyl)-3-aza-bicyclo[3.2.1]oct-8-yl]-phenyl}-methanesulfonamide;
3-[3-(4-Dimethylamino-naphthalen-1-ylmethyl)-8-methoxy-3-aza-bicyclo[3.2.1]oct-8-yl]-benzamide;
2-Methoxy-ethanesulfonic acid [3-(8-hydroxy-3-phenethyl-3-aza-bicyclo[3.2.1]oct-8-yl)-phenyl]-amide;
N-[3-(8-Methoxy-3-naphthalen-1-ylmethyl-3-aza-bicyclo[3.2.1]oct-8-yl)-phenyl]-methanesulfonamide;
N-[3-(8-Methoxy-3-naphthalen-2-ylmethyl-3-aza-bicyclo[3.2.1]oct-8-yl)-phenyl]-methanesulfonamide;
N-(3-{3-[3-(1-Hydroxy-cyclohexyl)-propyl]-8-methoxy-3-aza-bicyclo[3.2.1]oct-8-yl}-phenyl)-methanesulfonamide;
N-[3-(8-Methoxy-3-quinolin-4-ylmethyl-3-aza-bicyclo[3.2.1]oct-8-yl)-phenyl]-methanesulfonamide;
N-[3-(8-Methoxy-3-quinolin-3-ylmethyl-3-aza-bicyclo[3.2.1]oct-8-yl)-phenyl]-methanesulfonamide;
N-{3-[3-(4-Chloro-2-fluoro-benzyl)-8-methoxy-3-aza-bicyclo[3.2.1]oct-8-yl]-phenyl}-methanesulfonamide;
2-Methoxy-ethanesulfonic acid [3-(8-hydroxy-3-octyl-3-aza-bicyclo[3.2.1]oct-8-yl)-phenyl]-amide;
N-{3-[8-Methoxy-3-(1-methyl-1H-indol-3-ylmethyl)-3-aza-bicyclo[3.2.1]oct-8-yl]-phenyl}-methanesulfonamide;
2-Methoxy-ethanesulfonic acid {3-[8-hydroxy-3-(3-phenyl-prop-2-ynyl)-3-aza-bicyclo[3.2.1]oct-8-yl]-phenyl}-amide;
N-{3-[8-Hydroxy-3-(2-hydroxy-1,2,3,4-tetrahydro-naphthalen-2-ylmethyl)-3-aza-bicyclo[3.2.1]oct-8-yl]-phenyl}-methanesulfonamide;
N-{3-[3-(2-Hydroxy-indan-2-ylmethyl)-8-methoxy-3-aza-bicyclo[3.2.1]oct-8-yl]-phenyl}-methanesulfonamide;
2-Methoxy-ethanesulfonic acid {3-[8-hydroxy-3-(3-phenyl-propyl)-3-aza-bicyclo[3.2.1]oct-8-yl]-phenyl}-amide;
2-Methoxy-ethanesulfonic acid {3-[3-(4-chloro-benzyl)-8-hydroxy-3-aza-bicyclo[3.2.1]oct-8-yl]-phenyl}-amide;
N-{3-[3-(4-Hydroxy-naphthalen-1-ylmethyl)-8-methoxy-3-aza-bicyclo[3.2.1]oct-8-yl]-phenyl}-methanesulfonamide;
2-Methoxy-ethanesulfonic acid {3-[8-hydroxy-3-(1H-indol-3-ylmethyl)-3-aza-bicyclo[3.2.1]oct-8-yl]-phenyl}-amide;
N-{3-[8-Methoxy-3-(4-pyrrolidin-1-yl-benzyl)-3-aza-bicyclo[3.2.1]oct-8-yl]-phenyl}-methanesulfonamide;
N-{3-[8-Methoxy-3-(3-methyl-benzo[b]thiophen-2-ylmethyl)-3-aza-bicyclo[3.2.1]oct-8-yl]-phenyl}-methanesulfonamide;
2-Methoxy-ethanesulfonic acid [3-(3-benzofuran-2-ylmethyl-8-hydroxy-3-aza-bicyclo[3.2.1]oct-8-yl)-phenyl]-amide;
N-{3-[3-(2-Hydroxy-1,2,3,4-tetrahydro-naphthalen-2-ylmethyl)-8-methoxy-3-aza-bicyclo[3.2.1]oct-8-yl]-phenyl}-methanesulfonamide;
2,2,2-Trifluoro-N-{3-[3-(2-hydroxy-indan-2-ylmethyl)-8-methoxy-3-aza-bicyclo[3.2.1]oct-8-yl]-phenyl}-acetamide;
N-[3-(3-Biphenyl-4-ylmethyl-8-methoxy-3-aza-bicyclo[3.2.1]oct-8-yl)-phenyl]-methanesulfonamide;
2-Methoxy-ethanesulfonic acid [3-(8-hydroxy-3-naphthalen-2-ylmethyl-3-aza-bicyclo[3.2.1]oct-8-yl)-phenyl]-amide;
2-Methoxy-ethanesulfonic acid [3-(8-hydroxy-3-naphthalen-1-ylmethyl-3-aza-bicyclo[3.2.1]oct-8-yl)-phenyl]-amide;
2-Methoxy-ethanesulfonic acid (3-{8-hydroxy-3-[3-(1-hydroxy-cyclohexyl)-propyl]-3-aza-bicyclo[3.2.1]oct-8-yl}-phenyl)-amide;
2-Methoxy-ethanesulfonic acid [3-(8-hydroxy-3-quinolin-4-ylmethyl-3-aza-bicyclo[3.2.1]oct-8-yl)-phenyl]-amide;
2-Methoxy-ethanesulfonic acid [3-(8-hydroxy-3-quinolin-3-ylmethyl-3-aza-bicyclo[3.2.1]oct-8-yl)-phenyl]-amide;
2-Methoxy-ethanesulfonic acid {3-[8-hydroxy-3-(1-methyl-1H-indol-3-ylmethyl)-3-aza-bicyclo[3.2.1]oct-8-yl]-phenyl}-amide;
N-{3-[8-Methoxy-3-(3-trifluoromethoxy-benzyl)-3-aza-bicyclo[3.2.1]oct-8-yl]-phenyl}-methanesulfonamide;
2-Methoxy-ethanesulfonic acid{3-[3-(2-hydroxy-1,2,3,4-tetrahydro-naphthalen-2-ylmethyl)-3-aza-bicyclo[3.2.1]oct-8-yl]-phenyl}-amide;
2-Methoxy-ethanesulfonic acid {3-[8-hydroxy-3-(2-hydroxy-indan-2-ylmethyl)-3-aza-bicyclo[3.2.1]oct-8-yl]-phenyl}-amide;
N-{3-[3-(9H-Fluoren-2-ylmethyl)-8-methoxy-3-aza-bicyclo[3.2.1]oct-8-yl]-phenyl}-methanesulfonamide;
2-Methoxy-ethanesulfonic acid {3-[8-hydroxy-3-(2-phenethyloxy-ethyl)-3-aza-bicyclo[3.2.1]oct-8-yl]-phenyl}-amide;
N-{3-[8-Methoxy-3-(3-phenoxy-benzyl)-3-aza-bicyclo[3.2.1]oct-8-yl]-phenyl}-methanesulfonamide;
N-{3-[3-(4-Dimethylamino-naphthalen-1-ylmethyl)-8-methoxy-3-aza-bicyclo[3.2.1]oct-8-yl]-phenyl}-methanesulfonamide;
2-Methoxy-ethanesulfonic acid {3-[8-hydroxy-3-(4-hydroxy-naphthalen-1-ylmethyl)-3-aza-bicyclo[3.2.1]oct-8-yl]-phenyl}-amide;
2-Methoxy-ethanesulfonic acid {3-[8-hydroxy-3-(4-pyrrolidin-1-yl-benzyl)-3-aza-bicyclo[3.2.1]oct-8-yl]-phenyl}-amide;
2-Methoxy-ethanesulfonic acid {3-[8-hydroxy-3-(3-methyl-benzo[b]thiophen-2-ylmethyl)-3-aza-bicyclo[3.2.1]oct-8-yl]-phenyl}-amide;

2-Methoxy-ethanesulfonic acid {3-[3-(2-hydroxy-1,2,3,4-tetrahydro-naphthalen-2-ylmethyl)-8-hydroxy-3-aza-bicyclo[3.2.1]oct-8-yl]-phenyl}-amide;
2-Methoxy-ethanesulfonic acid {3-[3-(2-hydroxy-indan-2-ylmethyl)-8-methoxy-3-aza-bicyclo[3.2.1]oct-8-yl]-phenyl}-amide;
2-Methoxy-ethanesulfonic acid [3-(3-biphenyl-4-ylmethyl-8-hydroxy-3-aza-bicyclo[3.2.1]oct-8-yl)-phenyl]-amide;
2-Methoxy-ethanesulfonic acid {3-[3-(2-hydroxy-1,2,3,4-tetrahydro-naphthalen-2-ylmethyl)-8-methoxy-3-aza-bicyclo[3.2.1]oct-8-yl]-phenyl}-amide;
2-Methoxy-ethanesulfonic acid {3-[3-(9H-fluoren-2-ylmethyl)-8-hydroxy-3-aza-bicyclo[3.2.1]oct-8-yl]-phenyl}-amide;
2-Methoxy-ethanesulfonic acid {3-[8-hydroxy-3-(3-phenoxy-benzyl)-3-aza-bicyclo[3.2.1]oct-8-yl]-phenyl}-amide; and
2-Methoxy-ethanesulfonic acid {3-[3-(4-dimethylamino-naphthalen-1-ylmethyl)-8-hydroxy-3-aza-bicyclo[3.2.1]oct-8-yl]-phenyl}-amide;
and pharmaceutically acceptable salts of said compounds.
In further embodiments, the following compounds are more preferred:
3-(3-Cyclopropylmethyl-3-aza-bicyclo[3.2.1]oct-8-yl)-phenol;
3-(3-Ethyl-8-methoxy-3-aza-bicyclo[3.2.1]oct-8-yl)-benzamide;
3-(3-Cyclopropylmethyl-8-methoxy-3-aza-bicyclo[3.2.1]oct-8-yl)-benzamide;
3-[3-(3-Cyclohexyl-propyl)-3-aza-bicyclo[3.2.1]oct-8-yl]-phenol;
3-[8-Methoxy-3-(3-methyl-butyl)-3-aza-bicyclo[3.2.1]oct-8-yl]-benzamide;
3-(8-Methoxy-3-pentyl-3-aza-bicyclo[3.2.1]oct-8-yl)-benzamide;
3-(3-Hexyl-8-methoxy-3-aza-bicyclo[3.2.1]oct-8-yl)-benzamide;
3-[3-(2-Ethyl-butyl)-8-methoxy-3-aza-bicyclo[3.2.1]oct-8-yl]-benzamide;
2-[8-(3-Hydroxy-phenyl)-3-aza-bicyclo[3.2.1]oct-3-ylmethyl]-indan-2-ol;
3-[3-(1-Hydroxy-cyclohexyl)-propyl]-8-(3-hydroxy-phenyl)-3-aza-bicyclo[3.2.1]octan-8-ol;
N-[3-(3-Cyclopropylmethyl-8-methoxy-3-aza-bicyclo[3.2.1]oct-8-yl)-phenyl]-methanesulfonamide;
3-(2-Hydroxy-indan-2-ylmethyl)-8-(3-hydroxy-phenyl)-3-aza-bicyclo[3.2.1]octan-8-ol;
N-[3-(3-Isobutyl-8-methoxy-3-aza-bicyclo[3.2.1]oct-8-yl)-phenyl]-methanesulfonamide;
3-(8-Methoxy-3-octyl-3-aza-bicyclo[3.2.1]oct-8-yl)-benzamide;
3-{3-[3-(1-Hydroxy-cyclohexyl)-propyl]-8-methoxy-3-aza-[3.2.1]oct-8-yl}-phenol;
3-[8-Methoxy-3-(3-phenyl-propyl)-3-aza-bicyclo[3.2.1]oct-8-yl]-benzamide;
2-[8-(3-Hydroxy-phenyl)-8-methoxy-3-aza-bicyclo[3.2.1]oct-3-ylmethyl]-indan-2-ol;
N-{3-[8-Methoxy-3-(3-methyl-butyl)-3-aza-bicyclo[3.2.1]oct-8-yl]-phenyl}-methanesulfonamide;
N-[3-(8-Methoxy-3-pentyl-3-aza-bicyclo[3.2.1]oct-8-yl)-phenyl]-methanesulfonamide;
3-[3-(2-Hydroxy-1,2,3,4-tetrahydro-naphthalen-2-ylmethyl)-3-aza-bicyclo[3.2.1]oct-8-yl]-benzamide;
N-{3-[3-(2-Ethyl-butyl)-8-methoxy-3-aza-bicyclo[3.2.1]oct-8-yl]-phenyl}-methanesulfonamide;
N-[3-(3-Hexyl-8-methoxy-3-aza-bicyclo[3.2.1]oct-8-yl)-phenyl]-methanesulfonamide;
3-{3-[3-(1-Hydroxy-cyclohexyl)-propyl]-8-methoxy-3-aza-bicyclo[3.2.1]oct-8-yl}-benzamide;
3-[3-(2-Hydroxy-1,2,3,4-tetrahydro-naphthalen-2-ylmethyl)-8-hydroxy-3-aza-bicyclo[3.2.1]oct-8-yl]-benzamide;
3-[3-(2-Hydroxy-indan-2-ylmethyl)-8-methoxy-3-aza-bicyclo[3.2.1]oct-8-yl]-benzamide;
3-[8-Methoxy-3-(2-phenethyloxy-ethyl)-3-aza-bicyclo[3.2.1]oct-8-yl]-benzamide;
N-[3-(3-Heptyl-8-methoxy-3-aza-bicyclo[3.2.1]oct-8-yl)-phenyl]-methanesulfonamide;
2-Methoxy-ethanesulfonic acid [3-(8-hydroxy-3-pentyl-3-aza-bicyclo[3.2.1]oct-8-yl)-phenyl]-amide;
2-Methoxy-ethanesulfonic acid {3-[8-hydroxy-3-(3-methyl-butyl)-3-aza-bicyclo[3.2.1]oct-8-yl]-phenyl}-amide;
N-[3-(8-Methoxy-3-phenethyl-3-aza-bicyclo[3.2.1]oct-8-yl)-phenyl]-methanesulfonamide;
N-{3-[3-(4-Fluoro-benzyl)-8-methoxy-3-aza-bicyclo[3.2.1]oct-8-yl]-phenyl}-methanesulfonamide;
3-[3-(2-Hydroxy-1,2,3,4-tetrahydro-naphthalen-2-ylmethyl)-8-methoxy-3-aza-bicyclo[3.2.1]oct-8-yl]-benzamide;
3-[3-(1-Hydroxy-3-phenyl-cyclobutylmethyl)-8-methoxy-3-aza-bicyclo[3.2.1]oct-8-yl]-benzamide;
N-{3-[3-(2-Ethyl-hexyl)-8-methoxy-3-aza-bicyclo[3.2.1]oct-8-yl]-phenyl}-methanesulfonamide;
N-[3-(8-Methoxy-3-octyl-3-aza-bicyclo[3.2.1]oct-8-yl)-phenyl]-methanesulfonamide;
2-Methoxy-ethanesulfonic acid [3-(3-hexyl-8-hydroxy-3-aza-bicyclo[3.2.1]oct-8-yl)-phenyl]-amide;
N-{3-[3-(2-Hydroxy-indan-2-ylmethyl)-3-aza-bicyclo[3.2.1]oct-8-yl]-phenyl}-methanesulfonamide;
N-{3-[3-(4-Chloro-benzyl)-8-methoxy-3-aza-bicyclo[3.2.1]oct-8-yl]-phenyl}-methanesulfonamide;
2-Methoxy-ethanesulfonic acid [3-(3-cyclohexylmethyl-8-hydroxy-3-aza-bicyclo[3.2.1]oct-8-yl)-phenyl]-amide;
N-(3-{8-Hydroxy-3-[3-(1-hydroxy-cyclohexyl)-propyl]-3-aza-bicyclo[3.2.1]oct-8-yl}-phenyl)-methanesulfonamide;
N-{3-[3-(2-Hydroxy-1,2,3,4-tetrahydro-naphthalen-2-ylmethyl)-3-aza-bicyclo[3.2.1]oct-8-yl]-phenyl}-methanesulfonamide;
N-{3-[8-Hydroxy-3-(2-hydroxy-indan-2-ylmethyl)-3-aza-bicyclo[3.2.1]oct-8-yl]-phenyl}-methanesulfonamide;
2-Methoxy-ethanesulfonic acid [3-(8-hydroxy-3-phenethyl-3-aza-bicyclo[3.2.1]oct-8-yl)-phenyl]-amide;
N-(3-{3-[3-(1-Hydroxy-cyclohexyl)-propyl]-8-methoxy-3-aza-bicyclo[3.2.1]oct-8-yl}-phenyl)-methanesulfonamide;
2-Methoxy-ethanesulfonic acid [3-(8-hydroxy-3-octyl-3-aza-bicyclo[3.2.1]oct-8-yl)-phenyl]-amide;
N-{3-[8-Hydroxy-3-(2-hydroxy-1,2,3,4-tetrahydro-naphthalen-2-ylmethyl)-3-aza-bicyclo[3.2.1]oct-8-yl]-phenyl}-methanesulfonamide;
N-{3-[3-(2-Hydroxy-indan-2-ylmethyl)-8-methoxy-3-aza-bicyclo[3.2.1]oct-8-yl]-phenyl}-methanesulfonamide;
2-Methoxy-ethanesulfonic acid {3-[8-hydroxy-3-(3-phenyl-propyl)-3-aza-bicyclo[3.2.1]oct-8-yl]-phenyl}-amide;
N-{3-[3-(2-Hydroxy-1,2,3,4-tetrahydro-naphthalen-2-ylmethyl)-8-methoxy-3-aza-bicyclo[3.2.1]oct-8-yl]-phenyl}-methanesulfonamide;
2,2,2-Trifluoro-N-{3-[3-(2-hydroxy-indan-2-ylmethyl)-8-methoxy-3-aza-bicyclo[3.2.1]oct-8-yl]-phenyl}-acetamide;
2-Methoxy-ethanesulfonic acid (3-{8-hydroxy-3-[3-(1-hydroxy-cyclohexyl)-propyl]-3-aza-bicyclo[3.2.1]oct-8-yl}-phenyl)-amide;

2-Methoxy-ethanesulfonic acid{3-[3-(2-hydroxy-1,2,3,4-tetrahydro-naphthalen-2-ylmethyl)-3-aza-bicyclo[3.2.1]oct-8-yl]-phenyl}-amide;

2-Methoxy-ethanesulfonic acid {3-[8-hydroxy-3-(2-hydroxy-indan-2-ylmethyl)-3-aza-bicyclo[3.2.1]oct-8-yl]-phenyl}-amide;

2-Methoxy-ethanesulfonic acid {3-[8-hydroxy-3-(2-phenethyloxy-ethyl)-3-aza-bicyclo[3.2.1]oct-8-yl]-phenyl}-amide;

2-Methoxy-ethanesulfonic acid {3-[3-(2-hydroxy-1,2,3,4-tetrahydro-naphthalen-2-ylmethyl)-8-hydroxy-3-aza-bicyclo[3.2.1]oct-8-yl]-phenyl}-amide;

2-Methoxy-ethanesulfonic acid {3-[3-(2-hydroxy-indan-2-ylmethyl)-8-methoxy-3-aza-bicyclo[3.2.1]oct-8-yl]-phenyl}-amide; and 2-Methoxy-ethanesulfonic acid {3-[3-(2-hydroxy-1,2,3,4-tetrahydro-naphthalen-2-ylmethyl)-8-methoxy-3-aza-bicyclo[3.2.1]oct-8-yl]-phenyl}-amide;

and pharmaceutically acceptable salts of said compounds.

The compounds of the present invention may be used to bind to and modulate (i.e., inhibit, partially inhibit, activate, or partially activate) an opioid receptor or receptors in a mammal, including a human. The present compounds exhibit pharmacological activity consistent with such binding. Compounds according to the present invention may also be used as reference materials, reference standards, including calibration standards and as synthetic intermediates.

The subject invention is also directed to pharmaceutical compositions comprising an effective amount of one or more compounds according to the invention as otherwise described herein, optionally in combination with a pharmaceutically acceptable additive, carrier or excipient.

The subject invention also provides a pharmaceutical composition for treating in a mammal, including a human, in need thereof a disease state, disorder or condition mediated by an opioid receptor or receptors which composition comprises an amount of a compound according to formula I effective in modulating an opioid receptor or receptors and a pharmaceutically acceptable carrier.

The subject invention also provides a pharmaceutical composition for treating in a mammal, including a human, in need thereof a disorder or condition mediated by an opioid receptor or receptors which composition comprises an amount of a compound according to formula I effective in treating said disorder or condition and a pharmaceutically acceptable carrier.

The subject invention also provides a pharmaceutical composition for treating in a mammal, including a human, in need thereof a disorder or condition selected from irritable bowel syndrome; constipation; nausea; vomiting; pruritic dermatoses, for example allergic dermatitis or contact dermatitis; psoriasis; eczema; an insect bite; an eating disorder, for example anorexia, bulimia, or obesity; depression, anxiety, schizophrenia; drug addiction, for example alcohol addiction, amphetamine addiction, cocaine addiction or addiction to an opioid, for example morphine, opium, or heroine; an opioid overdose; a sexual dysfunction, for example erectile dysfunction or impotence; stroke; head trauma; traumatic brain injury; spinal damage; Parkinson's disease; Alzheimer's disease, age-related cognitive decline; and Attention Deficit and Hyperactivity Disorder; which composition comprises an amount of a compound of formula I effective in modulating an opioid receptor or receptors and a pharmaceutically acceptable carrier.

The subject invention also provides a pharmaceutical composition for treating in a mammal, including a human, in need thereof, a disorder or condition selected from irritable bowel syndrome; constipation; nausea; vomiting; pruritic dermatoses, for example allergic dermatitis or contact dermatitis; psoriasis; eczema; an insect bite; an eating disorder, for example anorexia, bulimia, or obesity; depression, anxiety, schizophrenia; drug addiction, for example alcohol addiction, amphetamine addiction, cocaine addiction or addiction to an opioid, for example morphine, opium, or heroine; an opioid overdose; a sexual dysfunction, for example erectile dysfunction or impotence; stroke; head trauma; traumatic brain injury; spinal damage; Parkinson's disease; Alzheimer's disease, age-related cognitive decline; and Attention Deficit and Hyperactivity Disorder; which composition comprises an amount of a compound of formula I effective in treating said disorder or condition and a pharmaceutically acceptable carrier.

Another aspect of the subject invention is directed to treating in a mammal, including a human, in need thereof, a disorder or condition mediated by an opioid receptor or receptors which method comprises administering to said mammal an amount of a compound according to formula I, or a pharmaceutically acceptabls salt of such a compound, effective in modulating an opioid receptor or receptors.

The subject invention also provides a method for treating in a mammal, including a human, in need thereof, a disease state, disorder or condition selected from irritable bowel syndrome; constipation; nausea; vomiting; pruritic dermatoses, for example allergic dermatitis or contact dermatitis; psoriasis; eczema; an insect bite; an eating disorder, for example anorexia, bulimia, and obesity; depression, anxiety, schizophrenia; drug addiction, for example alcohol addiction, amphetamine addiction, cocaine addiction or addiction to an opioid, for example morphine, opium, or heroine; an opioid overdose; a sexual dysfunction, for example erectile dysfunction or impotence; stroke; head trauma; traumatic brain injury; spinal damage; Parkinson's disease; Alzheimer's disease, age-related cognitive decline; and Attention Deficit and Hyperactivity Disorder; which method comprises administering to said mammal an amount of a compound of formula I as described, above effective to modulate an opioid receptor or receptors in said mammal.

The subject invention also provides a method for treating in a mammal, including a human, in need thereof, a disease state, disorder or condition selected from irritable bowel syndrome; constipation; nausea; vomiting; pruritic dermatoses, for example allergic dermatitis or contact dermatitis; psoriasis; eczema; an insect bite; an eating disorder, for example anorexia, bulimia, or obesity; depression, anxiety, schizophrenia; drug addiction, for example alcohol addiction, amphetamine addiction, cocaine addiction and addiction to an opioid, for example morphine, opium, or heroine; an opioid overdose; a sexual dysfunction, for example erectile dysfunction or impotence; stroke; head trauma; traumatic brain injury; spinal damage; Parkinson's disease; Alzheimer's disease, age-related cognitive decline; and Attention Deficit and Hyperactivity Disorder; which method comprises administering to said mammal an amount of a compound of formula I as described above effective in treating said disease state, disorder or condition in said mammal.

Thus, compounds of the present invention are useful because they possess pharmacological activity in animals, especially mammals, including humans. These compounds may also find use as standards in analytical assays or as intermediates in the synthesis of final compounds exhibiting pharmacological activity.

The subject invention also provides a method for treating in a mammal, including a human, in need thereof a disorder or condition mediated by an opioid receptor or receptors which method comprises administering to said mammal an amount of a compound according to formula I effective in treating said disorder or condition.

In the therapeutic methods of the subject invention as described above, the disease state, disorder or condition that is being treated is preferably irritable bowel syndrome, drug addiction, depression, anxiety, schizophrenia, or an eating disorder.

Methods of synthesizing compounds according to the present invention and key intermediates which can be in such methods are additional aspects of the present invention. These methods are described in greater detail hereinbelow.

DETAILED DESCRIPTION OF THE INVENTION

The following terms shall be used to describe the subject invention.

The term "compound", as used herein, unless otherwise indicated, refers to any specific chemical compound disclosed herein. Within its use in context, the term generally refers to a single compound, but in certain instances may also refer to stereoisomers and/or optical isomers (including racemic mixtures), as well as specific enantiomers or enantiomerically enriched mixtures of disclosed compounds, noting that in the subject invention, the relative chemistry of (AR)

and $R^3$ at the C-8 position of the present compounds is set as depicted in formula II, above. This diastereomeric relationship places the $R^3$ substituent on the same side of the bicyclic ring system as N-3.

The term "effective" is used herein, unless otherwise indicated, to describe an amount of a compound which, in context, is used to produce or effect an intended result, whether that result relates to the treatment of a disease state, disorder or condition or alternatively, is used to produce another compound, agent or composition.

The terms "treatment", "treating", and the like, refers to reversing, alleviating, or inhibiting the progress of the disorder or condition to which such term applies, or one or more symptoms of such disorder or condition. As used herein, these terms also encompass, depending on the condition of the patient, preventing the onset of a disorder or condition, or of symptoms associated with a disorder or condition, including reducing the severity of a disorder or condition or symptoms associated therewith prior to affliction with said disorder or condition. Thus, "treatment", as used herein, can refer to administration of a compound of the invention to a subject that is not at the time of administration afflicted with the disorder or condition. "Treating" thus also encompasses preventing the recurrence of a disorder or condition or of symptoms associated therewith.

The term "addiction", as used herein, for example in "drug addiction" and "alcohol addiction", unless otherwise indicated, refers to a maladaptive use of a substance, which may be either with physiological dependence or without. The term "addiction" thus includes both substance abuse (e.g. alcohol, amphetamine, cocaine or an opioid, for example morphine, opium, or heroine, abuse) and substance dependence (e.g. alcohol, amphetamine, cocaine or an opioid, for example morphine, opium, or heroine, dependence). The maladaptive pattern of substance use may manifest itself in recurrent and significant adverse consequences related to the repeated use of the substance. The recurrent substance use may result in a failure to fulfill major role obligations at work, school, or home. The maladaptive use of a substance may involve continued use of the substance despite persistent, or recurrent social or interpersonal problems caused or exacerbated by the effects of the substance (e.g., arguments with spouse, physical fights). The maladaptive pattern of substance use may involve clinically significant impairment or distress, for example manifested by tolerance for the substance, withdrawal symptoms, self-injurious behavior, unsuccessful efforts to cut down or control the substance use, and/or taking larger amounts of the substance and/or taking amounts of the substance over a longer period than was intended. Substances to which an addiction may be formed include, but are not limited to, the drugs recited above (including alcohol), as well as others, for example benzodiazepines such as Valium®.

The term "mammal", as used herein, and unless otherwise indicated, means any mammal. The term "mammal" includes, for example and without limitation, dogs, cats, and humans. The term "patient" or "subject" may be alternatively used to describe such a mammal, including a human, to whom treatment or use with the compounds or compositions according to the subject invention is provided. For treatment or use with/or of those disease states, conditions or disease states which are specific for a specific animal (especially, for example, a human subject or patient), the term patient or subject refers to that particular animal.

References herein to disease states, disorders and conditions "mediated by an opioid receptor or receptors" indicate disorders or conditions the treatment of which can be fascilitated by modulating (i.e. inhibiting, partially inhibiting, activating, or partially activating) an opioid receptor or receptors. Examples of disorders and conditions the treatment of which is fascilitated by modulation of an opioid receptor or receptors include, but are not limited to, irritable bowel syndrome, eating disorders, sexual dysfunction, depression, anxiety, schizophrenia and drug addictions, as well as the other specific disorders and conditions recited herein.

The term "alkyl", as used herein, unless otherwise indicated, includes saturated monovalent hydrocarbon radicals having straight, cyclic or branched moieties. Examples of alkyl groups include, but are not limited to, methyl, ethyl, propyl, isopropyl, sec-butyl and t-butyl. Within context, the use of the term "alkyl" may also subsume the use of or refer to alkylene groups, i.e., a hydrocarbon radical derived from alkyl groups which are diradicals, rather than monoradicals.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl.

The term "carbocyclic", as used herein, unless otherwise indicated, refers to a cyclic group in which all of the atoms of the ring are carbon atoms. Representative carbocyclic groups include cycloalkyl groups as described above. The term carbocyclic subsumes the term aryl within it.

The term "heterocyclic", as used herein, unless otherwise indicated, refers to a cyclic group in which at least one atom of the ring is a heteroatom (i.e., O, S or N). The term heterocyclic subsumes the term heteroaryl within it. Thus, a 5- to 7-membered heterocyclic group subsumes a 5- to 7-membered heteroaryl group within it.

The term "aryl", as used herein, unless otherwise indicated, includes an organic radical derived from an aromatic hydrocarbon by removal of one hydrogen, such as phenyl, naphthyl, indenyl, and fluorenyl.

The term "heteroaryl", as used herein, refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. The foregoing groups, as derived from the compounds listed above, may be C-attached or N-attached where such is possible. For instance, a group derived from pyrrole may be pyrrol-1-yl (N-attached), pyrrol-2-yl or pyrrol-3-yl (C-attached). The terms referring to the groups also encompass all possible tautomers.

The term "phenyl-fused" or "heteroaryl-fused", as used herein, refers to a heterocyclic or carbocyclic group, which forms a ring by attaching or bonding two atoms (carbon and/or heteroatoms) of the heterocyclic or carbocyclic group to two atoms of the phenyl or heteroaryl group.

The term "reductive amination", as used herein, refers to any process whereby the combination of an aldehyde or a ketone, or aldehyde or ketone equivalent, such as a bisulfite addition complex of an aldehyde, is combined with, in reference to the subject invention, a primary amine, secondary amine or ammonia, or ammonia source, such that the compounds condense to generate an intermediate imine or iminium ion that may be subjected to reduction by means of hydrogenation, such as mediated by a metal species such as palladium or platinum in many forms useful for reduction and a hydrogen source, such as hydrogen gas, or any precursor to hydrogen gas, including but not limited to formate derivatives or cyclohexadiene, or other hydride sources whereby hydride delivery from said source occurs by mechanisms commonly understood and employed. These include hydride reagents such as boron or aluminum hydride sources, for instance borohydrides, such as $[(X)_nBH_{4-n}]^-$ (n=0, 1, 2, 3) or aluminum hydrides such as $[(X)_nAlH_{4-n}]^-$ (n=0, 1, 2, 3) (wherein X may be any of the commonly cited ligands for transformations such a reductive amination including but not limited to acetoxy, trifluoroacetoxy, alkoxy, or lower alkyl for boron or alkoxy or lower alkyl for aluminum). Other hydrides may be equally suited to these transformations (for instance silanes or stannanes).

The term "reducing" or "reductive conditions", as used herein, refers to any process whereby dehydrohalogenation, hydrogenolysis, hydrogenation, or reduction of unsaturated bonds occurs as desired.

The term "leaving group", as used herein, refers to any group suitable in the conversion of a primary amine, secondary amine or ammonia or ammonia source that effectively departs in a bond-forming event from a carbon atom of interest, such as in an alkylation reaction. Suitable groups include halides (iodide, bromide or chloride), sulfonates (such methane sulfonate, trifluoromethanesulfonate or, aryl sulfonates such as tosyl or nosyl groups), epoxides or aziridines or any variation that is well known to those of skill in the art. In addition, the processes involving leaving groups may be employed in the formation of other C—X bonds where the nucleophile X is oxygen, sulfur, or carbon centered.

The term "carbonyl protecting group", as used herein, refers to any group that can withstand chemistry performed on other portions of the molecule without being substantially structurally compromised. Such groups must withstand reduction, reductive amination and alkylation chemistry as defined. These groups may include alkoxy groups such as dimethoxy, diethoxy, other $C_1$–$C_6$ dialkoxy, diphenoxy, or cyclic ketals such as cyclic dialkoxy groups such as dioxolanes, 1,3-dioxanes or catechols, among others.

Pharmaceutical salts of compounds according to the present invention are an important aspect. Pharmaceutical salts of compounds of formula I can be obtained by forming salts with any acidic or basic group present on a compound of formula I. Examples of pharmaceutically acceptable salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid, mandelic acid, sodium, potassium, magnesium, calcium, and lithium. Mesylate and/or citrate salts may be particularly preferred in the subject invention.

As noted above, the compounds of formula I may have optical centers and therefore may occur in different enantiomeric and other stereoisomeric configurations. The invention includes all enantiomers, diastereomers, and other stereoisomers of such compounds of formula I, as well as racemic and other mixtures thereof.

The synthetic methods described below in the "Detailed Description" section and in Examples produce primarily compounds of formula I having the relative stereochemistry illustrated by compounds of formula I below:

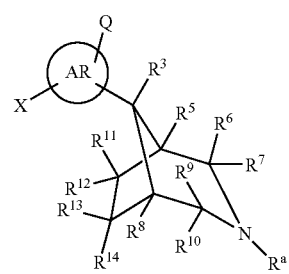

I

Preferred compounds according to the subject invention, generally as depicted in formula I and as more specifically depicted in formula III, and as described more fully herein, and their pharmaceutically acceptable salts can be prepared according to the following reaction Schemes I through XIX as described herein. Unless otherwise indicated Q, n, j, m, n, v, $R^a$ and $R^1$ through $R^{22}$ are as defined generally above. Isolation and purification of the products is accomplished by standard procedures which are known to a chemist of ordinary skill in the art. In addition, by following the disclosed chemistry more generically and/or by analogy, one of ordinary skill may readily provide all of the compounds according to the subject invention.

As used herein, the expression "reaction inert solvent" refers to a solvent system in which the components do not interact with starting materials, reagents, or intermediates of products in a manner that adversely affects the yield of the desired product.

During any of the following synthetic sequences it may be necessary and/or desirable to protect sensitive or reactive groups on any of the molecules concerned. This may be achieved by means of conventional protecting groups, such as those described in T. W. Greene, *Protective Groups in Organic Chemistry*, John Wiley —Sons, 1981; and T. W. Greene and P. G. M. Wuts, *Protective Groups in Organic Chemistry*, John Wiley —Sons, 1991.

Scheme I–XIX illustrate methods for the preparation of compounds having the basic structure of formula I, where Q=Br, CN, $NH_2$, $OCH_3$, OH, $NHSO_2R^{15}$, $CONH_2$, $R^3$=H, Cl, OH, $OCH_3$, $R^5$–$R^{14}$=H and $R^1$, $R^2$, and $R^4$ are described as above. Other compounds according of formula I may be readily synthesized by analogy following the specific methods described in detail herein and following well-known synthetic methods in the art.

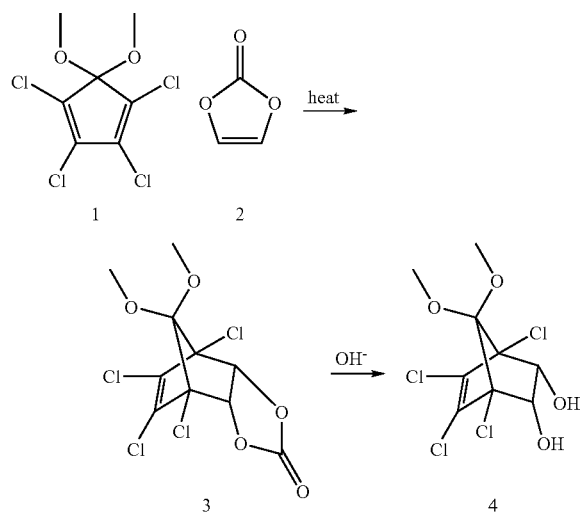

Referring to Scheme I, a diene of formula 1 can be combined with a dienophile of formula 2 and heated to temperatures ranging from room to 100° C., preferably 100° C., to produce a compound of formula 3. Hydrolysis of this compound of formula 3 under basic aqueous conditions at temperatures ranging from room to reflux, preferably room temperature, produces the corresponding diol of formula 4.

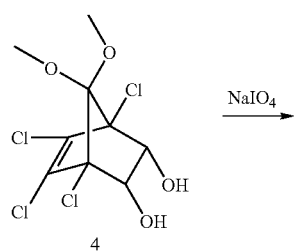

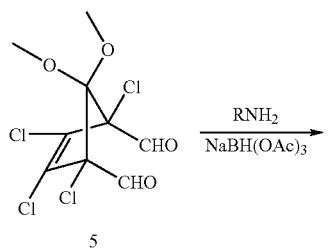

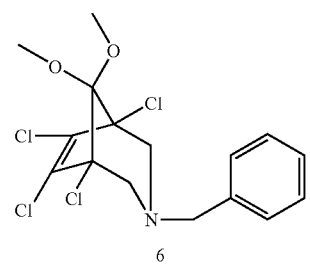

Referring to Scheme II, treatment of a diol of formula 4 with an appropriate oxidizing agent such as sodium periodate in a biphasic aqueous/organic medium such as aqueous dichloroethane, will produce the corresponding compound of formula 5. This may alternatively be performed as desired in an organic solvent such as an alcohol, for instance methanol, ethanol or isopropanol or an ethereal solvent such as THF or dimethoxyethane or dioxane, or a dipolar aprotic solvent such as DMF, DMA or NMP, or a chlorinated solvent such as cichloromethane or dichloroethane, if the counterion of the $IO_4^-$ ion is an alkali metal ion such $Na^+$, tetraalkylammonium ion such as $Et_3NBn^+$ or $n-Bu_4N$ or other suitable organic solublizing cations, if the medium is vigorously stirred. This may be preferably performed using sodium periodate in dichloroethane at ambient temperature with vigorous stirring. Treatment of the di-aldehyde of formula 5 with an appropriate reducing agent such as for example sodium triacetoxyborohydride in the presence of an appropriate primary amine such as benzyl amine at temperatures ranging from 0° C. to room temperature in chlorinated solvents such as dichloromethane or dichloroethane will produce the corresponding amine of formula 6. By analogy, $RNH_2$ may be any suitable $H_2N(CH_2)_nR^1R^2R^4$, or $R^aNH_2$ group or $PNH_2$, where P is any suitable protecting group.

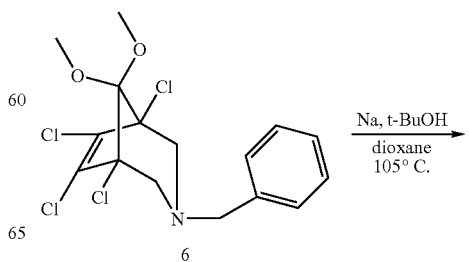

-continued

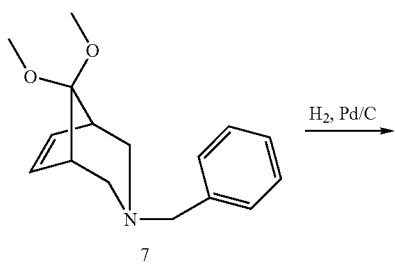

7

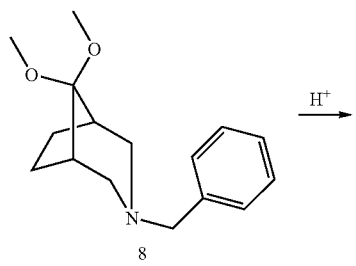

8

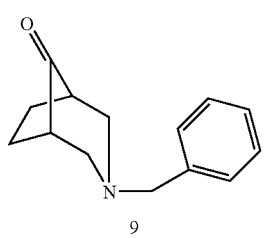

9

-continued

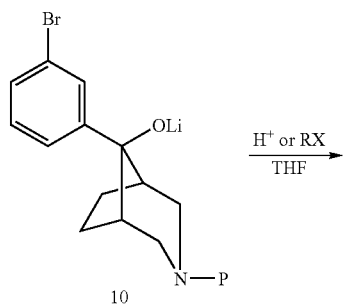

10

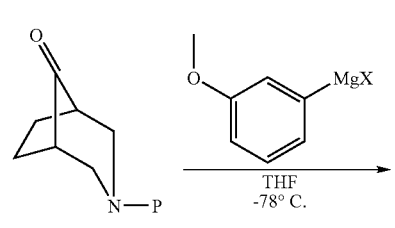

11

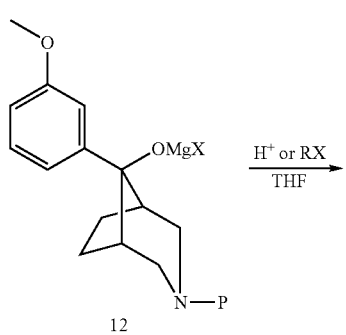

12

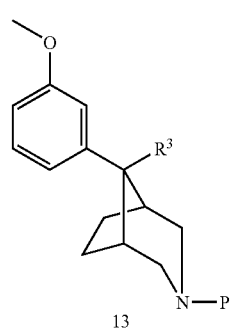

13

P = benzyl, p-methoxybenzyl or $R^a$
$R^3$ = OH, OCH$_3$

Referring to Scheme III, reduction of a compound of formula 6 with sodium metal in ethereal solvents such as tetrahydrofuran, dimethoxyethane or dioxane, preferably dioxane, in the presence of an alcohol such as ethanol, isopropanol or t-butanol, preferably t-butanol at temperatures ranging from room temperature to the reflux temperature, preferably the reflux temperature, will produce the desired compound of formula 7. Hydrogenation of this compound of formula 7 with hydrogen gas (at pressures ranging from atmospheric to 50 psi) in the presence of a suitable catalyst such as palladium on carbon, in an organic solvent such as ethyl acetate at room temperature to the reflux temperature, preferably at room temperature, produces the compound of formula 8. Hydrolysis of this compound of formula 8 under acidic aqueous conditions at temperatures ranging from room to reflux, produces the desired compound of formula 9.

Scheme IV

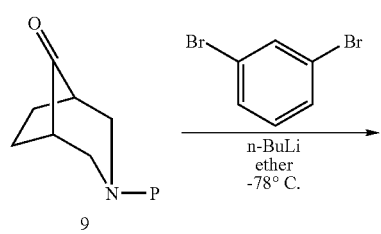

9

Referring to Scheme IV, a ketone of formula 9 can be treated with an aryl lithium or aryl Grignard species in an ethereal solvent such as diethyl ether at temperatures from −78° C. to room temperature, preferably at −78° C. The aryl metal species may be substituted with Q groups (and X groups) or suitable Q group precursors (and X group precursors). The aryl metal addition generates an intermediate alcoholate 10 that may be quenched with, electrophilic agents. Suitable electrophilic agents, such as a proton source, for instance a protic acid or water, or alkylating agents such as alkyl halides, for instance iodomethane in an aprotic solvent such as tetrahydrofuran at room temperature to the reflux temperature, preferably room temperature, produces the desired compound of formula 11. The aryl metal species may be aryl Grignard reagents, used preferably in an ethereal solvent such as tetrahydrofuran to produce a corresponding derivative 12, which in turn may be converted to the desired compound of formula 13 as described above. It may be desirable to generate aryl-CeCl$_2$ species, an aryl-ZnX species, both usually derived from aryl-Li or aryl-MgX species, as is known in the art. Such species may improve the yield in a particular addition, but are preferably not required.

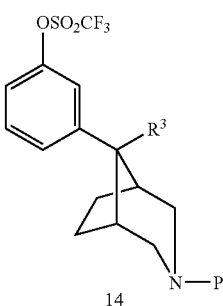

P = benzyl, p-methoxybenzyl or R$^a$

Referring to Scheme V, treatment of a compound of formula 11 with benzophenone imine, a suitable catalyst such as palladium (II) acetate, a suitable phosphine ligand such as BINAP, and a suitable base, such as sodium t-butoxide, in a suitable solvent such as toluene, at temperatures ranging from room temperature to about the reflux temperature, produces the intermediate imine, which is then treated in situ with aqueous acid at temperatures ranging from room to reflux, preferably at 80–100° C., producing the aniline of formula 15. Alternatively, treatment of a compound of formula 16 with C$_6$H$_5$N(SO$_2$CF$_3$)$_2$ in the presence of a suitable base, such as triethylamine in a solvent such as methylene chloride, will produce the trifluoromethanesulfonate (triflate) of formula 14. Treatment of a triflate of formula 14 with benzophenone imine, a described above produces the aniline of formula 15.

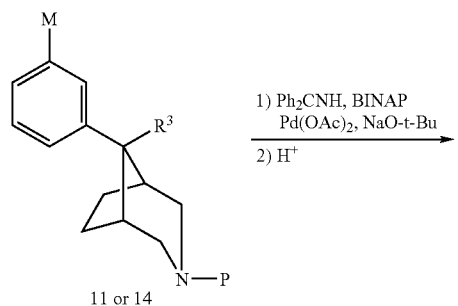

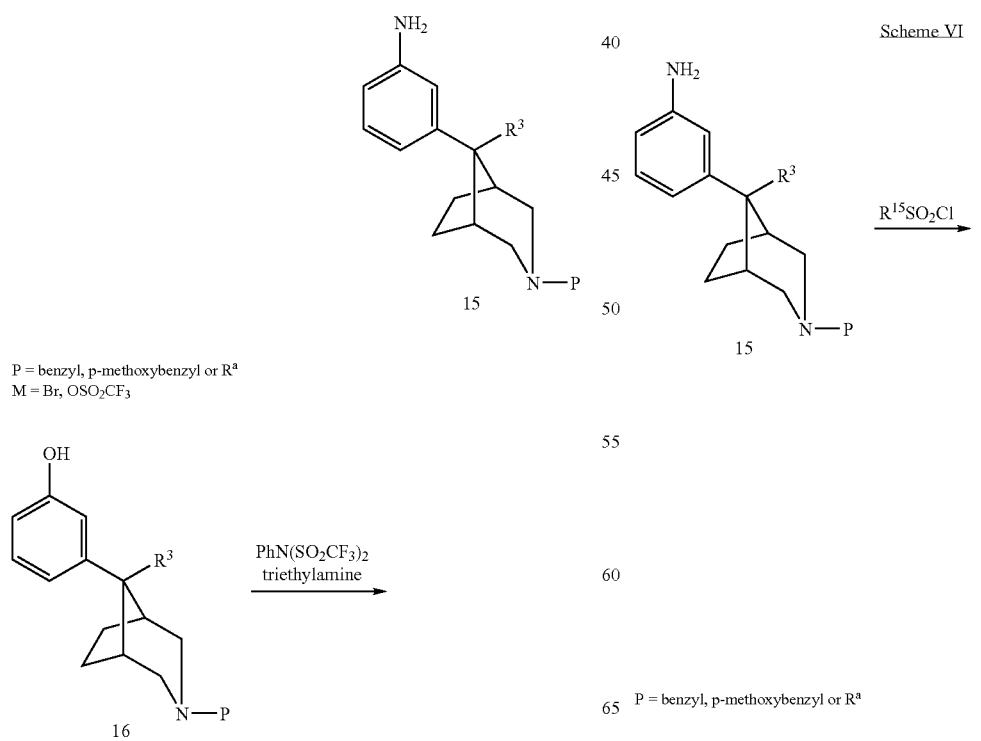

Referring to Scheme VI, treatment of an aniline of formula 15 with an appropriately substituted sulfonyl chloride, such as methanesulfonyl chloride or 2-methoxy-ethanesulfonyl chloride, in the presence of a suitable base, such as pyridine, in a solvent such as methylene chloride, at temperatures ranging from 0° C. to room temperature, preferably at about room temperature, produces the desired sulfonamide of formula 17.

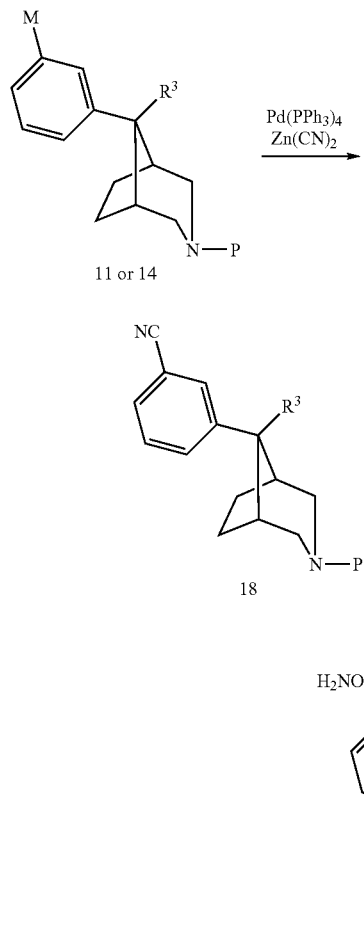

P = benzyl, p-methoxybenzyl or $R^a$
M = Br, $OSO_2CF_3$

Referring to Scheme VII above, treatment of a bromide of formula 11 or triflate of formula 14 with zinc cyanide, in the presence of a suitable catalyst, such as tetrakistriphenylphosphine palladium (0), in solvents such as dimethylformamide, at temperatures ranging from room temperature to about reflux temperature, preferably at about 85° C., produces the corresponding nitrile of formula 18. Conversion of a nitrile of formula 18 by the action of; for instance dilute hydrogen peroxide, in the presence of a suitable alkali metal base, such as potassium carbonate, in solvents such as dimethylformamide or dimethylsulfoxide, at temperatures ranging from 0° C. to about room temperature, preferably at about room temperature, produces the corresponding amide of formula 19.

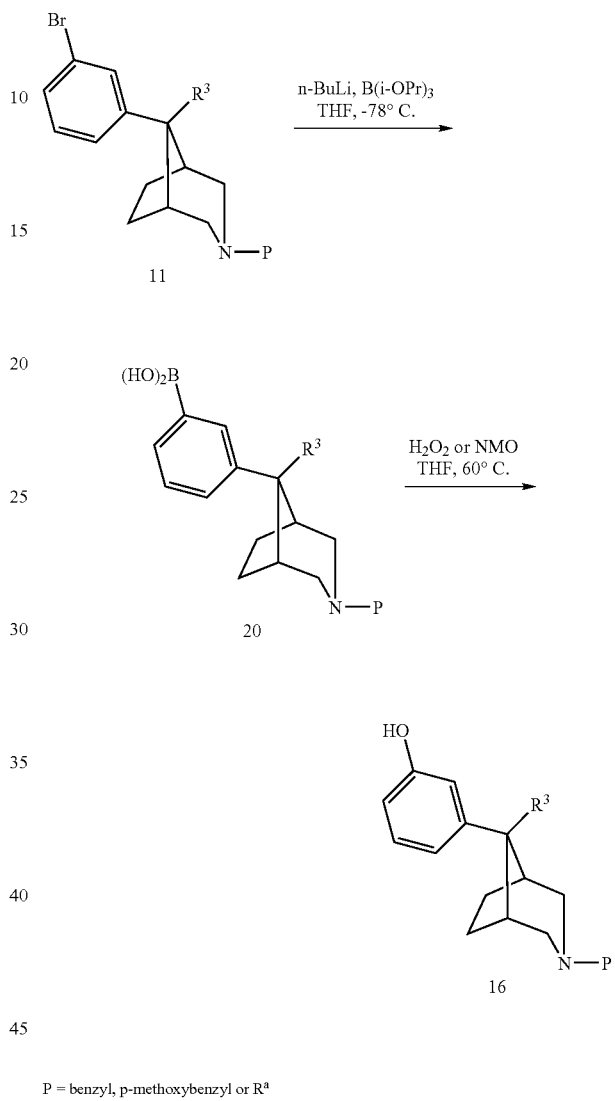

P = benzyl, p-methoxybenzyl or $R^a$

Referring to Scheme VIII, treatment of a suitable halide, such as a bromide of formula 11 with n-butyllithium in aprotic solvents, such as tetrahydrofuran, at temperatures ranging from −78° C. to room temperature, preferably −78° C., followed by treatment with borane or borate source, such as borane or a trialkoxyborate, such as triisopropylborate will produce an intermediate boron "ate complex" which after hydrolysis with aqueous media will produce the boronic acid of formula 20. Oxidation of boronic acid of formula 20 with suitable oxidants such as hydrogen peroxide or preferably 4-methylmorpholine-N-oxide in aprotic solvents such as tetrahydrofuran, at temperatures ranging from room temperature to reflux temperature, preferably at reflux, produces the corresponding phenol of formula 16.

Scheme IX

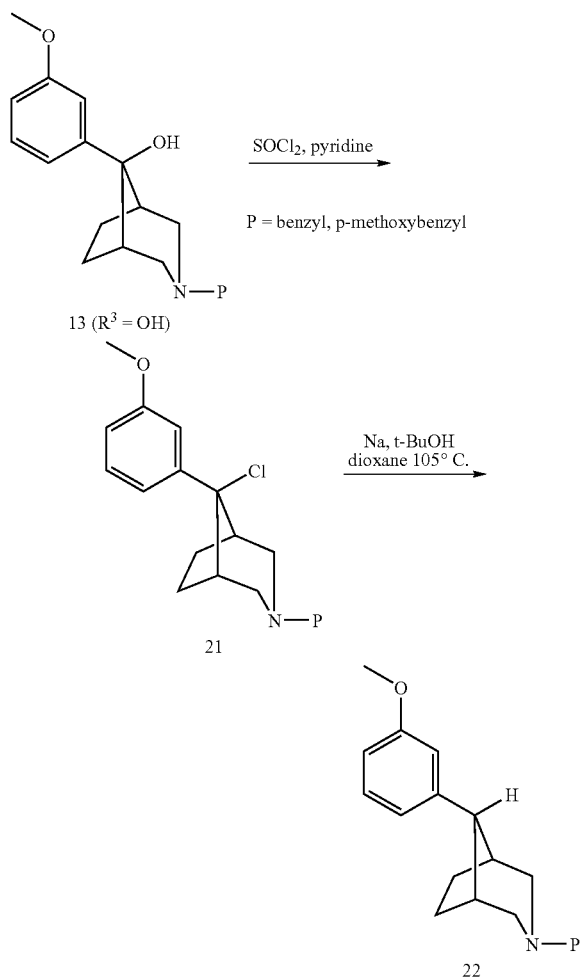

Referring to Scheme IX, treatment of compounds of formula 13 (R$^a$=OH) with thionyl chloride in the presence of a suitable base, such as pyridine, in a chlorinated solvent such as methylene chloride produces the desired product of formula 21. Treatment of a compound of formula 21 with sodium metal in the presence of weak acid such as t-butanol in an aprotic solvent such as dioxane at temperatures ranging from room temperature to reflux, preferably reflux, produces the desired product of formula 22.

Scheme X

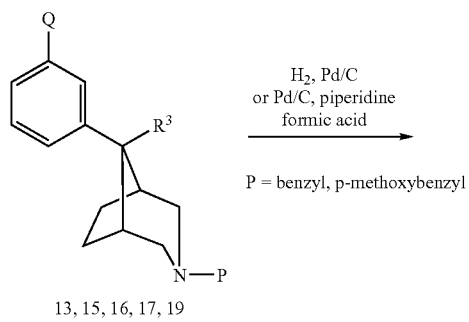

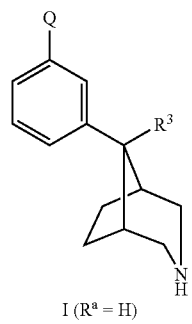

As shown above in Scheme X, compounds of formula I (R$^a$=H) can be prepared by the hydrogenolysis of compounds of formula 13, 15, 16, 17 or 19 with hydrogen gas (at pressures ranging from atmospheric to 50 psi) in the presence of a suitable catalyst such as palladium on carbon, in alcoholic solvents such as methanol, at temperatures ranging from room temperature to reflux, preferably at about 60° C. Alternatively, compounds of formula I (R$^a$=H) can be prepared by treatment of compounds of formula 13, 15, 16, 17 or 19 with ammonium salts of formic acid, such as ammonium formate, or more preferably, that formed by contacting piperidine and formic acid in the presence of a suitable catalyst, such as palladium on carbon, in alcoholic solvents, such as methanol or ethanol, at temperatures ranging from room temperature to about the reflux temperature, preferably at about reflux temperature. These methods are useful for the conversion of any compound wherein Q or X as described previously are stable to the conditions as describe here, as may be determined by one skilled in the art.

Scheme XI

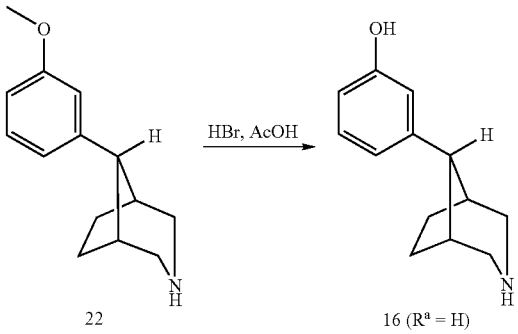

Referring to Scheme XI above, compounds of formula 16 (R$^a$=H) can be prepared by treatment of a compound of formula 22 with hydrobromic acid in the presence of acetic acid at temperatures ranging from room temperature to about the reflux temperature, preferably about the reflux temperature.

Scheme XII

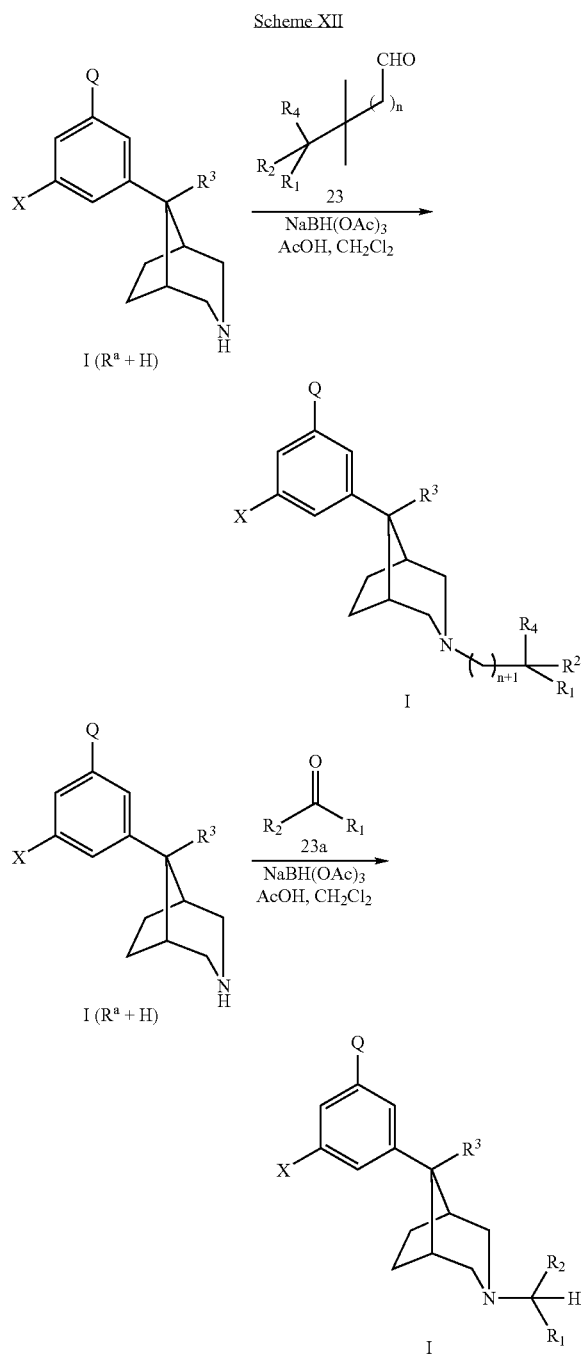

Referring to Scheme XII, treatment of a compound of formula I ($R^a$=H) with an appropriately substituted aldehyde of formula 23 (or the corresponding alkali metal bisulfite addition compound of said aldehyde) or ketone of formula 23a and a reducing agent such as sodium triacetoxyborohydride, in the presence of acetic acid, in solvents such as chlorinated solvents, such as dichloromethane or dichloroethane or an alcohol, such as methanol, or an ethereal solvent such as THF, or any combination of these solvents, at temperatures ranging from 0° C. to about room temperature, preferably at about room temperature, produce the corresponding compounds of formula I. Precursors to this step can be prepared using methods that are known to one of ordinary skill in the art. Equally useful in this step is the use of ketones, such that compounds wherein n=0 may be prepared.

Scheme XIII

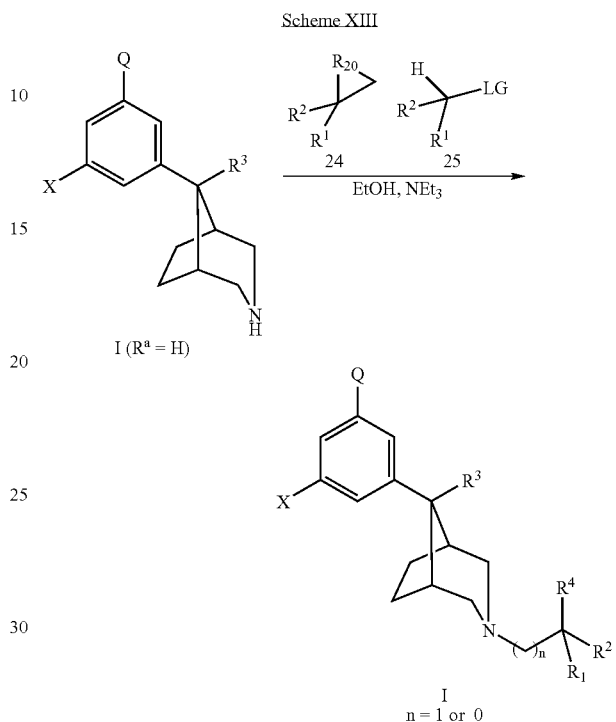

Referring to Scheme XIII above, compounds of formula I can be prepared by treatment of a compound of formula I ($R^a$=H) with a reagent of formula 24 wherein $R^{20}$ is oxygen or —NH or —NSO$_2$R or —NCOOR, or a compound of formula 25 wherein LG (leaving group) is a suitable sulfonate, such as methansulfonate, trifluoromethanesulfonate or arylsulfonate, or a halide, such as chloride, bromide or iodide. This reaction should be carried out in the presence of a suitable base such as a tertiary amine, for instance triethylamine, in alcoholic solvents such as ethanol or isopropanol at temperatures ranging from room temperature to about the reflux temperature, preferably at about the reflux temperature to produce the desired compound of formula I.

Scheme XIV

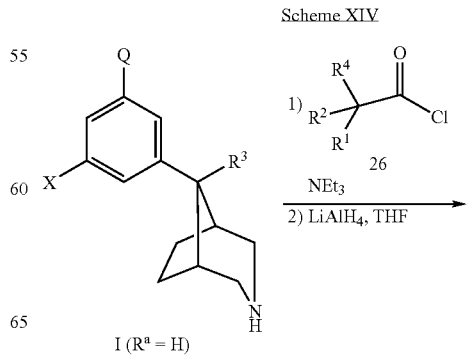

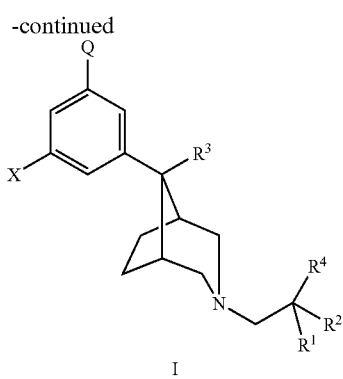

Alternatively, referring to Scheme XIV compounds of formula I can also be prepared by treatment of a compound of formula I ($R^a$=H) with an appropriately substituted acid chloride of formula 26. The reaction should be carried out in the presence of a suitable base such as hydroxide ion, $Et_3N$ or pyridine, in solvents such as water, tetrahydrofuran or methylene chloride, at temperature ranging from 0° C. to room temperature, preferably at about room temperature. Any of the suitable methods for preparing amides known to those skilled in the art are appropriate for use in this transformation. The amide products from this reaction (not depicted) are then reduced with a suitable reducing agent, such as lithium aluminum hydride Dibal-H or borane in solvents such as ethyl ether or tetrahydrofuran, at temperatures ranging from room temperature to about the reflux temperature, preferably at about the reflux temperature, which produce the desired products of formula I. Any of the suitable methods for reducing amides known to those skilled in the art that will not affect other functionalities present in the target compound are appropriate for use in this transformation. Reagents 26 can be prepared using methods that are known to one of ordinary skill in the art.

Alternative methods of preparation are equally suited to the generation of compounds of the invention. For instance as is indicated in Scheme XV, it is possible to access bicyclic ketones, such as that depicted as formula 28, by methods previously described in the literature from cyclopentanones such as 27 (House, H. O., Bryant III, W. M. J. Org. Chem. 1965, 30, 3634. Afsah, E. M.; Metwally, M. A.; Khalifa, M. M. Monatsh. Chem. 1984, 115, 303–308. House; Mueller; J. Org. Chem. 1962, 27, 4436 and 4439. Lowe, J. A.; Drozda, S. E.; McLean, S.; Bryce, D. K.; Crawford, R. T. J. Med. Chem. 1994, 37, 2831). This allows the generation of materials with radicals $R^5$ and $R^8$ as defined previously, or to be precursors to such radicals as defined. As such these radicals may be H, esters, ketones, nitriles and sulfones and methylene amines (as described in the references above). These may be converted to alcohols, for instance at a later step from ketones by from which halides may be introduced by for instance DAST (F incorporation) and HX. Certain $R^5$ and $R^8$ radicals are precursors to other radicals, including where $R^5$ and $R^8$=H. This may be accomplished by methods known to those in the art. For instance, sulfones and nitriles may be reduced by dissolving alkali metal reductions (e.g. see Arapakos, P. G. J. Am. Chem. Soc. 1967, 89, 6794).

A further method of preparing compounds of the invention as described here in Scheme XV, and that may be utilized by analogy in Scheme II. As such it is possible to incorporate the $H_2N(CH_2)_nCR^1R^2R^3$ radical in the reductive amination (Scheme II) or Mannich cyclization (Scheme XV) approaches. In such cases this radical, —P or —$R^a$ as defined in compounds of formula I, may be protecting groups such as for instance benzyl, which has been indicated throughout this description, and it may be desirable to incorporate the radical as desired in a compound of the invention such as depicted in formula I, II or III.

It is further indicated that aryl metal species, wherein X and Q, or suitable precursors to X and Q, are present in this species, may provide an expeditious route to compounds of formula I, II or III of the invention.

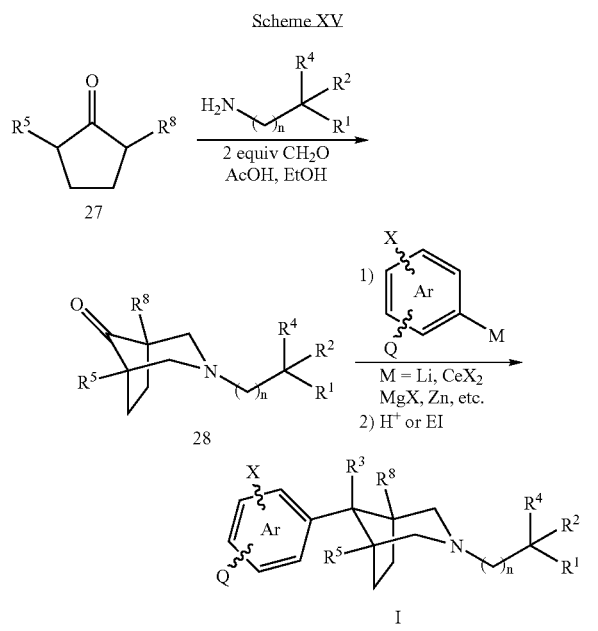

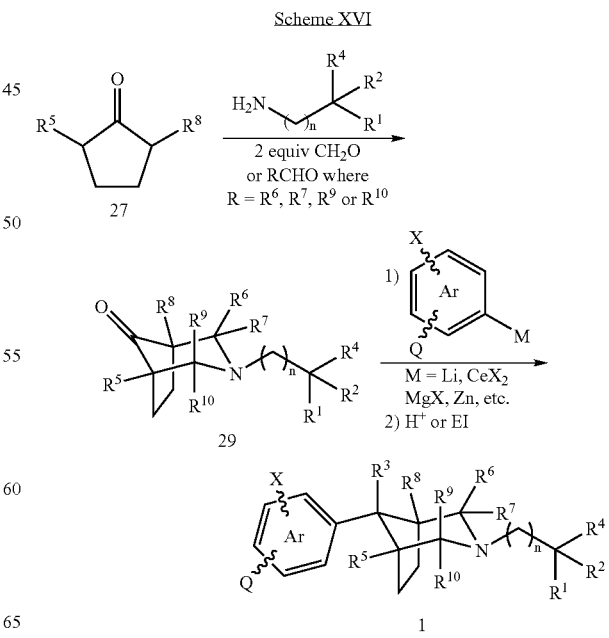

Furthermore, it is possible that the use of aldehydes in place of formaldehyde may conveniently provide access to compounds where either $R^6$ or $R^7$ or $R^9$ or $R^{10}$ is varied as described above (Scheme XVI).

Scheme XVII

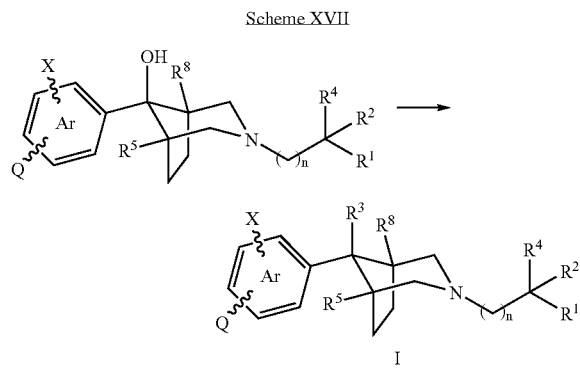

The preparation of compounds of the invention whereby $R^3$ is not H, OH or OMe as described in prior discussion may be prepared from intermediates as in Scheme XVII. In this regard, conversion of a compound whereby $R^3$=OH may be converted into a compound with $R^3$=Cl, (by the action of $SOCl_2$), F (by the action of DAST) or Br (by the action of $SOBr_2$). These may be further converted to compounds described in the invention by methods described in the art. For instance for $R^3$=Cl or Br, compounds of this type may be converted to for instance lithium, magnesium or transition metals by methods known in the art. Metal mediated processes are known for conversion to materials where $R^3$=alkyl, unsaturated (such as vinyl), aryl and carbonyl. For instance $TiCl_4/ZnR^3{}_2$ may be used to generate methyl, ethyl or other saturated radicals. $R^3$=Br may be induced to oxidatively insert transition metal species, for instance palladium° species to generate useful intermediates for conversion to unsaturated products such as vinyl, allyl, CN, COOR or CONRR. These in turn can then be converted to compounds of the invention as described by methods known to those in the art.

Scheme XVIII

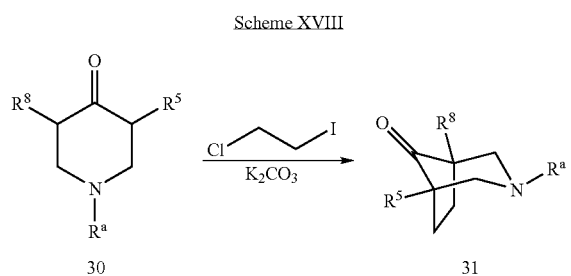

A further method of preparing compounds of the invention as described here in Scheme XVIII, whereby a piperidone such as 30, suitably substituted, may be converted by dialkylation to a ketone intermediate as previously depicted. For instance, when $R^5$ and/or $R^8$ are sulfones, carbonyls or nitriles a dialkylation with for instance 2-chloroiodoethane will furnish the bicyclic ketone of formula 31.

Scheme XIX

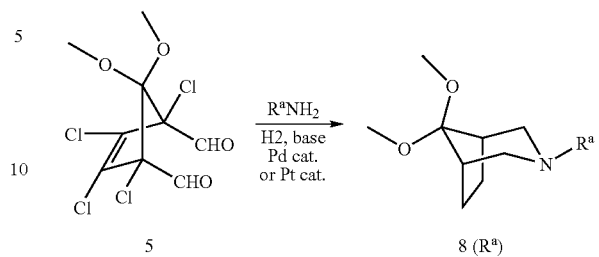

It is envisioned that the processes required to prepare intermediate ketals such as compounds of the formula 8 as depicted in Scheme III may be generated under the appropriate reducing conditions such as with Pd or Pt catalysis in the presence of hydrogen gas and in the presence of an appropriate base such as an alkali metal hydroxide or carbonate at room or elevated temperature, and from atmospheric to 300 atmospheres of pressure, such as that generated in a pressure chamber. Under such conditions, ketals 8 ($R^a$ as defined previously) may be prepared as depicted in Scheme XIX and used as described previously in conversions to compounds of formula I of the invention.

The stereochemistry of compounds of formula I synthesized according to the methods described above can be determined using standard spectroscopic methods. Isolation of the desired diastereomer of a compound of formula I from a diastereomeric mixture can be accomplished using standard separation methods know to those of ordinary skill in the art, for example crystallization or chromatographic methods. In such compounds as defined in the subject invention, the relative chemistry of (AR)

and $R^3$ at the C-8 position is set as depicted in formula II, above. This diastereomeric relationship places the $R^3$ substituent on the same side of the bicyclic ring system as the N-3.

The subject invention also includes isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$. Compounds of the subject invention and pharmaceutically acceptable salts of said compounds that contain the aforementioned isotopes and/or other isotopes of other atoms are within the scope of this invention. Isotopically labeled compounds of the subject invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula I of this invention can generally be prepared by carrying out the procedures disclosed in the Schemes and/or in the Examples above, by substituting a readily available isotopically labeled reagent for a non-isotopically labeled reagent.

Accordingly, the subject invention also provides a compound of formula I wherein one or more atoms thereof have an atomic mass or mass number different from the atomic mass or mass number usually found in nature, or a pharmaceutically acceptable salt of such compound. The subject invention also provides a method for obtaining an image of opioid receptors in a mammalian, including a human, subject which method comprises administering to said subject an amount of an isotopically-labeled compound of formula I, or pharmaceutically acceptable salt thereof, effective in imaging opioid receptors in said subject.

Pharmaceutically acceptable salts of a compound of formula I can be prepared in a conventional manner by treating a solution or suspension of the corresponding free base or acid with a pharmaceutically acceptable acid or base. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids. Illustrative bases are sodium, potassium, and calcium.

A compound of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining a compound of formula I or a pharmaceutically acceptable salt thereof can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing a compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

A compound of formula I or a pharmaceutically acceptable salt thereof can be administered orally, transdermally (e.g., through the use of a patch), parenterally (e.g. intravenously), rectally, topically, or by inhalation. In general, the daily dosage for treating a disorder or condition as described herein using a compound of formula I will be about from about 0.01 to about 100 mg per kg, preferably from about 0.1 to about 10 mg per kg, of the body weight of the animal to be treated. As an example, a compound of the formula I, or a pharmaceutically acceptable salt thereof, can be administered for treatment to an adult human of average weight (about 70 kg) in a dose ranging from about 0.1 mg up to about 10 g per day, preferably from about 1 mg to about 1 g per day, in single or divided (i.e., multiple) portions. Variations based on the aforementioned dosage ranges may be made by a physician of ordinary skill taking into account known considerations such as the weight, age, and condition of the animal being treated, the severity of the affliction, and the particular route of administration chosen.

Biological Activity

Compounds of formula I of the subject invention have been found to display activity in opioid receptor binding assays selective for the mu, kappa and delta opioid receptors. Assays for mu, kappa and delta opioid receptor binding can be performed according to the following procedure:

Affinity of a compound for the delta opioid receptor can be assessed using binding of the delta opioid receptor ligand [$^3$H]-naltrindole to NG108-15 neuroblastoma-glioma cells according to modification of the protocol described in Law et al. (Law, P. Y., Koehler, J. E. and Loh, H. H., "Comparison of Opioid Inhibition of Adenylate Cyclase Activity in Neuroblastoma N18TG2 and Neuroblastoma X Glioma NG108-15 Hybrid Cell Lines", *Molecular Pharmacology*, 21: 483–491 (1982)). Law et al. is incorporated herein in its entirety by reference. Affinity of a compound for the kappa opioid receptor can be assessed using binding of [$^3$H]-bremazocine to kappa receptors as described in Robson, L. E., et al., "Opioid Binding Sites of the Kappa-type in Guinea-pig Cerebellum", *Neuroscience* (*Oxford*), 12(2): 621–627 (1984). Robson et al. is incorporated herein it its entirey by reference. For assessment of a compound for mu opioid receptor activity, the mu receptor ligand [$^3$H]-DAMGO (Perkin Elmer Life Sciences, Boston, Mass.; specific activity 55 Ci/mmol, 1.5 nM) is used with rat forebrain tissue. Briefly, the binding is initiated with the addition of a crude membrane preparation of rat forebrain tissue to 96-well polypropylene plates containing the radioligand [$^3$H]-DAMGO and test compound, and are incubated for about 90 minutes at about 25° C. The assay is terminated by rapid filtration with 50 mM Tris HCl pH 7.4 onto Wallac Filtermat B and counted on a Betaplate reader (Wallac).

The data generated can be analyzed using $IC_{50}$ analysis software in Graphpad Prism. Ki values can be calculated using Graphpad Prism according to the following formula:

$$Ki=IC_{50}/1+[^3H \text{ ligand}]/K_D$$

where $IC_{50}$ is the concentration at which 50% of the $^3H$ ligand is displaced by the test compound and $K_D$ is the dissociation constant for the $^3H$ ligand at the receptor site.

The Ki values of certain compounds of formula I of the Examples, as described, infra, in a mu opioid receptor binding assay to brain tissue such as that described above, were determined. All of the compounds tested in this manner were all found to have Ki values of about 800 nM or less for the mu opioid receptor.

The inhibition (%) of [$^3H$]-DAMGO binding by certain compounds of formula I of the Examples, as described, infra, in a mu opioid receptor binding assay to brain tissue such as that described above, were determined. Most of the compounds tested at 100 nM were found to inhibit [$^3H$]-DAMGO binding at the mu opioid receptor in a range of 10–100%.

Other assays which may be used for determining the binding of compounds according to the present invention to opioid receptors are well known in the art. These assays may be used to assess the ability of a compound to modulate (i.e., inhibit, partially inhibit, activate or partially activate) an opioid receptor or receptors by determining a compound's agonist or antagonist activity in the in vitro or in vivo assay. These assays include, for example, the GTP gamma S binding assay as described in Martin, et al., *J. Pharm. Exp. Ther.*, 301, 661–671 (2003) and Zaki, et al., *J. Pharm. Exp. Ther.*, 298, 1015–1020 (2002), as well as other binding assays, such as the isolated guinea pig ileum and receptor binding assay as disclosed, for example, by Takayama, et al., *J. Med. Chem.*, 45, 1949–1956 (2002) and the guinea pig brain binding assay as described by Wentland, et al., *J. Med. Chem.*, 46, 838–849 (2003). The use of mouse brain tissue to determine the functional activity of the compounds of interest is another binding assay which can be used for characterizing the modulation of the present compounds at opioid receptors, as disclosed by Martin, et al., *Idem*. Other binding assays include the tail-flick assay in mice or the radiant heat paw-withdrawal hyperalgesic testing in mice, as described by Hosohata, et al., *J. Pharm. Exp. Ther.*, 304, 683–688 (2003), among others. These assays or variations of these assays are well-known to those of ordinary skill in the art.

The present invention also relates to methods of synthesizing compounds according to the present invention or to key intermediates which may be used to synthesize compounds according to the present invention.

A first synthetic aspect relates to a method of synthesizing a compound according to the chemical structure:

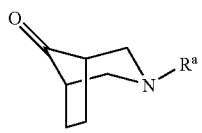

comprising reacting a primary amine compound of formula $R^a NH_2$ with a compound according to the chemical structure:

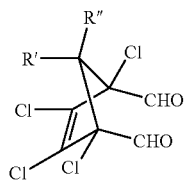

where $R^a$ is as otherwise described hereinabove and is suitably disposed to the reaction conditions by either maintaining chemical integrity or becoming another desired $R^a$ group and R' and R" together represent carbonyl protecting groups, and are each independently $C_1$–$C_6$ alkoxy groups, phenoxy groups or together form a cyclic ketal group, said reacting step occurring under reductive amination or reducing conditions (preferably, at room or elevated temperature in the presence of base, a hydrogenation catalyst and hydrogen gas at a pressure ranging from atmospheric pressure to about 300 atmospheres of pressure); and thereafter removing said protecting groups R' and R" to form

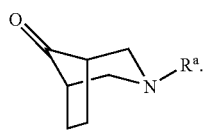

In this first synthetic aspect of the present invention, the cyclic ketal is a dioxolane, 1,3 dioxane group or catechol, the hydrogenation catalyst is a platinum or palladium hydrogenation catalyst and the base is an alkali metal hydroxide or a carbonate.

In a second synthetic aspect of the present invention, compounds according to the following chemical structure IV:

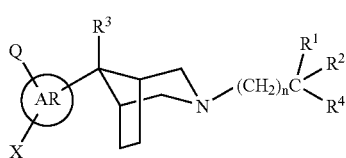

where AR, Q, X, $R^1$, $R^2$ $R^3$, $R^4$ and j, m, n and v are as otherwise described hereinabove are prepared by reacting a compound according to the chemical structure:

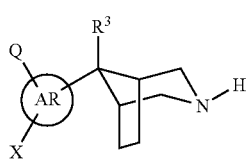

with a reactive compound according to the chemical structure:

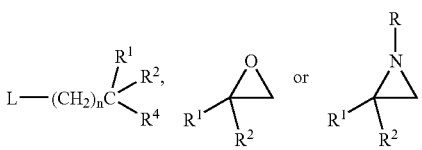

where L is a leaving group, R is H, $SO_2R^b$ or $CO_2R^b$ and $R^b$ is an aryl group or a $C_1$–$C_4$ alky group to provide a compound according to structure IV.

In a third synthetic aspect of the present invention, compounds according to the following chemical structure IVa:

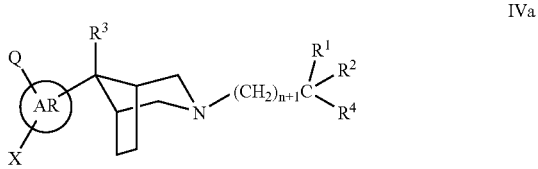

IVa are prepared by reacting a compound according to the chemical structure:

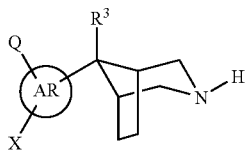

with a compound according to the structure:

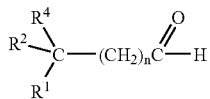

under reductive amination conditions to produce the compound according to structure IVa.

The following specific examples illustrate the subject invention. It is to be understood, however, that the invention, as fully described herein and as recited in the claims, is not intended to be limited by the details of the following Examples.

EXAMPLES

Preparation 1

1,7,8,9-Tetrachloro-10,10-dimethoxy-3,5-dioxa-tricyclo[5.2.1.0$^{2,6}$]dec-8-en-4-one In a 500 mL 3N RB flask equipped with a water condenser, $N_2$ flow adapter and thermometer, was placed 5,5-dimethoxy-1,2,3,4-tetrachlorocyclopentadiene (20.7 g, 0.078 mol) and vinylene carbonate (6.7 g, 0.078 mol). The mixture was heated to 90° C. for 4 h, then at 60° C. for 63 h. The reaction was judged complete by TLC and upon cooling, the product solidified, was recrystallized from THF and filtered to provide a white solid (25.80 g, 94%). (TLC 20% EtOAc/hexanes $R_f$ 0.29); $^1$H NMR (400 MHz, CDCl$_3$) δ 5.13 (s, 2H), 3.59 (s, 3H), 3.56 (s, 3H); GCMS m/z 348 (M)$^+$; mp 160–162° C.; Anal. Calcd. for $C_{10}H_8Cl_4O_5$: C, 34.32; H, 2.30. Found C, 34.32; H, 2.27.

1,4,5,6-Tetrachloro-7,7-dimethoxy-bicyclo[2.2.1]hept-5-ene-2,3-diol

Potassium hydroxide (112 g, 1.20 mol) in water (1 L) was treated with 1,7,8,9-tetrachloro-10,10-dimethoxy-3,5-dioxatricyclo[5.2.1.0$^{2,6}$]dec-8-en-4-one (358.3 g, 1.23 mol) in THF (500 mL) via addition funnel, producing a slight exotherm. The reddish solution was stirred overnight at room temperature. By morning, the solution became a murky dispersion, which was diluted with water (500 mL), and 12N HCl (20 mL) to pH 10. The product was extracted with EtOAc (1×1000 mL) and ether (1×500 mL). The combined organic layers were washed with 1N HCl (1×300 mL), water (1×300 mL), saturated aqueous NaHCO$_3$ solution (1×300 mL) and saturated aqueous NaCl solution (1×300 mL), dried over Na$_2$SO$_4$, filtered and concentrated to give a light brown solid (310 g, 78%). (TLC 40% EtOAc/hexanes $R_f$ 0.55); $^1$H NMR (400 MHz, CDCl$_3$) δ 4.46 (s, 2H), 3.54 (s, 3H), 3.51 (s, 3H); GCMS m/z 322 (M)$^+$, 287, 289 (M-Cl)$^+$; mp 160–162° C.; Anal. Calcd for C$_9$H$_{10}$Cl$_4$O$_4$: C, 33.37; H, 3.11. Found C, 33.34; H, 3.16.

3-Benzyl-1,5,6,7-tetrachloro-8,8-dimethoxy-3-aza-bicyclo[3.2.1]oct-6-ene 1,4,5,6-Tetrachloro-7,7-dimethoxy-bicyclo[2.2.1]hept-5-ene-2,3-diol (155 g, 0.48 mol) in DCE (1 L) and water (750 mL) was charged with sodium periodate (151.7 g, 0.49 mol). This mixture was stirred at room temperature for 20 min then transferred to a separatory funnel. The layers were separated then back extracted with DCE (1×400 mL). The organic layer was washed with water (1×1000 mL) and 25% saturated aqueous NaCl solution (2×1000 mL or until no reaction to starch iodide is observed in the aqueous wash), then dried through a cotton plug into a mixture of benzylamine (53.8 g, 0.50 mol) and NaBH(OAc)$_3$ (324.5 g, 1.53 mol) in DCE (1300 mL), producing a slight exotherm. The reaction was stirred vigorously for ~63 h at room temperature then quenched with saturated aqueous Na$_2$CO$_3$ solution (~500 mL) and allowed to stir at 20° C. until CO$_2$ evolution ceased (~30 min). The organic layer was washed with saturated aqueous Na$_2$CO$_3$ solution (500 mL), saturated aqueous NaCl solution (500 mL), filtered through a silica pad (3×3 in) eluting with DCE, and concentrated to provide an amber oil (178 g, 94%). (TLC 100% DCE $R_f$ 0.88); $^1$H NMR (400 MHz, CDCl$_3$) δ 7.31–7.21 (5H), 3.74 (s, 2H), 3.59 (s, 3H), 3.56 (s, 3H), 2.80 (AB d, J=10.8 Hz, 2H), 2.74 (AB d, J=10.8 Hz, 2H); APCI MS m/z 397.8 (M+1)$^+$; Anal. Calcd for 4 C$_{16}$H$_{17}$Cl$_4$NO$_2$ H$_2$O: C, 47.85; H, 4.21; N, 3.43. Found C, 47.94; H, 4.21; N, 3.43.

3-Benzyl-8,8-dimethoxy-3-aza-bicyclo[3.2.1]oct-6-ene

To a 3 L 3NRB equipped with a thermometer, addition funnel and water condenser was added dioxane (1000 mL) then sodium (44.7 g, 1.94 mol). Upon heating under reflux (T ~100° C.), the sodium became a dispersed immiscible liquid. While maintaining this gentle reflux, a solution of 3-benzyl-1,5,6,7-tetrachloro-8,8-dimethoxy-3-aza-bicyclo[3.2.1]oct-6-ene (52.5 g, 0.132 mol), t-butanol (160 mL, 1.67 mol) and dioxane (150 mL) was added dropwise via the addition funnel over 30 min and heat continued overnight. Upon cooling to 70° C., the residual unreacted sodium was quenched with MeOH (150 mL) then water (1 L). The dioxane and MeOH were then removed in vacuo. The product was extracted from the aqueous layer with EtOAc (3×300 mL), washed with saturated aqueous NaCl solution (1×300 mL), dried over Na$_2$SO$_4$, filtered and concentrated to yield a dark brown oil (29.2 g, 85%). (TLC 40% EtOAc/hexanes R$_f$ 0.35); $^1$H NMR (400 MHz, CDCl$_3$) δ 7.28–7.20 (5H), 6.01 (t, J=1.6 Hz, 2H), 3.65 (s, 2H), 3.23 (s, 3H), 3.17 (s, 3H), 2.63 (s, 2H), 2.57 (AB d, J=10.1 Hz, 2H), 2.44 (AB d, J=10.1 Hz, 2H); GCMS m/z 259 (M)$^+$; APCI MS m/z 260.2 (M+1)$^+$.

3-Benzyl-8,8-dimethoxy-3-aza-bicyclo[3.2.1]octane

3-Benzyl-8,8-dimethoxy-3-aza-bicyclo[3.2.1]oct-6-ene (51.8 g, 0.2 mol) was dissolved in EtOAc (100 mL) in a 500 mL Parr bottle. To this was added 20% Pd(OH)$_2$/C (Degussa type, 2.60 g) and the mixture was shaken under 45 psi of H$_2$ for 4 h (or judged complete by TLC). The reaction was filtered through a Celite pad, rinsed with EtOAc, and concentrated to a brown liquid (50.4 g, 97%). (TLC 30% EtOAc/hexanes R$_f$ 0.63); $^1$H NMR (400 MHz, CDCl$_3$) δ 7.33–7.17 (5H), 3.51 (s, 2H), 3.22 (s, 3H), 3.16 (s, 3H), 2.50 (AB dd, J=10.4, 3.7 Hz, 2H), 2.40 (AB d, J=10.4 Hz, 2H), 2.04 (br s, 2H), 1.70–1.64 (m, 4H); APCI m/z 262.3 (M+1)$^+$.

3-Benzyl-3-aza-bicyclo[3.2.1]octan-8-one

3-Benzyl-8,8-dimethoxy-3-aza-bicyclo[3.2.1]octane (50.4 g, 0.19 mol) and 3N HCl (500 mL) were heated to reflux 4 h (or until judged complete by TLC). Upon cooling to room temperature, the aqueous solution containing product was washed with ether (2×200 mL) then back extracted from the ether layer with 1N HCl (100 mL). The combined aqueous layers were made alkaline with NaOH (~50 g) in water (500 mL). The product was extracted with EtOAc (3×300 mL), washed with saturated aqueous NaCl solution (1×200 mL), dried over Na$_2$SO$_4$, filtered through a pad of silica (5×4 in), rinsed with 100% EtOAc, and concentrated to a brown liquid (42.0 g, 100%). (TLC 30% EtOAc/hexanes R$_f$ 0.55); $^1$H NMR (400 MHz, CDCl$_3$) δ 7.37–7.24 (5H), 3.59 (s, 2H), 2.98 (ddd, J=9.5, 4.2, 2.1 Hz, 2H), 2.54 (d, J=10.8 Hz, 2H), 2.16 (brs, 2H), 2.06 (dd, J=12.4, 4.8 Hz, 2H), 1.85 (m, 2H); APCI MS m/z 216.3 (M+1)$^+$.

Preparation 2

1,5,6,7-Tetrachloro-8,8-dimethoxy-3-(4-methoxy-benzyl)-3-aza-bicyclo[3.2.1]oct-6-ene 1,4,5,6-Tetrachloro-7,7-dimethoxy-bicyclo[2.2.1]hept-5-ene-2,3-diol (1.23 g, 3.80 mmol) and sodium periodate (1.19 g, 3.80 mmol) were stirred vigorously for 1.5 h in DCE (10 mL) and water (10 mL). The di-aldehyde was extracted with DCE (2×15 mL), washed with water (5×10 mL, or until no reaction to starch iodide is observed in the aqueous wash), then filtered through a cotton plug under N$_2$ into a slurry of p-methoxybenzylamine (0.52 mL, 3.99 mmol) and NaBH(OAc)$_3$ (2.58 g, 12.16 mmol) in DCE (10 mL). After 3 h at room temperature the reaction was judged complete by TLC. The solvent was removed in vacuo, and the residue was quenched with saturated aqueous NaHCO$_3$ solution. The product was extracted with EtOAc (3×30 mL), washed with saturated aqueous NaCl solution (1×30 mL), dried over Na$_2$SO$_4$, filtered through a silica pad (2×3 in), eluted with 100% EtOAc and concentrated to yield the title compound as a white solid (1.32 g, 82%). (TLC 30% EtOAc/hexanes R$_f$ 0.65); $^1$H NMR (400 MHz, CDCl$_3$) δ 7.12 (d, J=8.3 Hz, 2H), 6.81 (d, J=8.3 Hz, 2H), 3.77 (s, 3H), 3.61 (s, 2H), 3.59 (s, 3H), 3.56 (s, 3H), 2.76 (d, J=11.4 Hz, 2H), 2.71 (d, J=11.1 Hz, 2H); GCMS m/z 427 (M)$^+$.

8,8-Dimethoxy-3-(4-methoxy-benzyl)-3-aza-bicyclo[3.2.1]oct-6-ene 1,5,6,7-Tetrachloro-8,8-dimethoxy-3-(4-methoxy-benzyl)-3-aza-bicyclo[3.2.1]oct-6-ene (6.23 g, 146 mmol) and t-butanol (25.13 mL, 263 mmol) were dissolved in dioxane (75 mL) in a flame dried 3N RB equipped with a water condenser and thermometer then heated to a gentle reflux (internal temp 92° C.). Sodium (5.36 g, 233 mmol) was pre-washed sequentially with hexanes/ethanol/THF/hexanes then added portionwise to the above refluxing mixture over 45 min The reaction was heated overnight and judged complete by GCMS. The reaction solution was decanted from the unreacted sodium, then washed with methanol to fully quench residual sodium. Solvent was removed in vacuo, diluted in water (100 mL), cooled in an ice bath, then acidified with 6 N HCl (100 mL). At room temperature, the acidic aqueous layers were washed with ether (2×100 mL) then made alkaline with 1N NaOH. The product was extracted with EtOAc (3×100 mL), washed with saturated aqueous NaCl solution (1×100 mL), dried over Na$_2$SO$_4$, filtered and concentrated to yield the title compound (3.97 g, 94%). (TLC 5% MeOH/CH$_2$Cl$_2$, (NH$_3$) R$_f$ 0.40); $^1$H NMR (400 MHz, CDCl$_3$) δ 7.16 (d, J=8.3 Hz, 2H), 6.79 (d, J=8.3 Hz, 2H), 5.97 (s, 2H), 3.76 (s, 3H), 3.56 (s, 2H), 3.20 (s, 3H), 3.13 (s, 3H), 2.59 (br s, 2H), 2.53 (d, J=10.6 Hz, 2H), 2.39 (d, J=10.6 Hz, 2H); GCMS m/z 287 (M)$^+$.

8,8-Dimethoxy-3-(4-methoxy-benzyl)-3-aza-bicyclo[3.2.1]octane 8,8-Dimethoxy-3-(4-methoxy-benzyl)-3-aza-bicyclo[3.2.1]oct-6-ene (5.92 g, 20.5 mmol) was dissolved in EtOAc (50 mL) in a 250 mL Parr bottle. To this was added catalytic 20% Pd(OH)$_2$/C (Pearlman's catalyst, 500 mg) and the mixture was shaken under 40 psi of H$_2$ for 4 h or until judged complete by TLC. The reaction was filtered through a Celite pad and concentrated to a yellow oil (4.88 g, 82%). (TLC 5% MeOH/CH$_2$Cl$_2$, (NH$_3$) R$_f$ 0.60); $^1$H NMR (400 MHz, CDCl$_3$) δ 7.21 (d, J=8.3 Hz, 2H), 6.81 (d, J=8.3 Hz, 2H), 3.76 (s, 3H), 3.43 (s, 2H), 3.21 (s, 3H), 3.15 (s, 3H), 2.48 (dd, J=10.3, 3.3 Hz, 2H), 2.36 (d, J=10.3 Hz, 2H), 2.02 (br s, 2H), 1.65 (m, 4H); GCMS m/z 291 (M)$^+$.

3-(4-Methoxy-benzyl)-3-aza-bicyclo[3.2.1]octan-8-one 8,8-Dimethoxy-3-(4-methoxy-benzyl)-3-aza-bicyclo[3.2.1]octane (4.88 g, 0.0167 mol) was dissolved in 1N HCl (50 mL) then heated to reflux 2 h (or until judged complete by TLC). The reaction was cooled to room temperature, washed with ether (1×50 mL), then the aqueous layer was made alkaline with 1 N NaOH and saturated aqueous NaHCO$_3$ solution. The product was extracted with EtOAc (4×70 mL) then CH$_2$Cl$_2$ (1×50 mL), washed with saturated aqueous NaCl solution (200 mL), dried over Na$_2$SO$_4$, filtered then concentrated to yellow oil (3.88 g, 94%). (TLC 50% EtOAc/hexanes R$_f$ 0.55); $^1$H NMR (400 MHz, CDCl$_3$) δ 7.22 (d, J=8.3 Hz, 2H), 6.83 (d, J=8.3 Hz, 2H), 3.77 (s, 3H), 3.49 (s, 2H), 2.92 (dd, J=11.4, 3.9 Hz, 2H), 2.46 (d, J=10.8 Hz, 2H), 2.12 (br s, 2H), 2.00 (dd, J=12.7, 4.6 Hz, 2H), 1.83 (m, 2H); GCMS m/z 245 (M)$^+$.

Preparation 3

3-(4-Methoxy-benzyl)-8-(3-methoxy-phenyl)-3-aza-bicyclo[3.2.1]octan-8-ol 3-(4-Methoxy-benzyl)-3-aza-bicyclo[3.2.1]octan-8-one (1.09 g, 4.44 mmol) was azeotroped from THF (3×50 mL) then dissolved in anhydrous THF (20 mL) under N$_2$ and cooled to −78° C. This was treated with 3-methoxyphenylmagnesiumbromide (4.89 mL, 4.89 mmol) dropwise and stirred at −78° C. for 5 min, then warmed to room temperature. The reaction was quenched with 1N HCl (pH 1), washed with ether (2×50 mL), then the organic layer was back extracted with water (1×50 mL). The combined aqueous layers were neutralized to pH 8 with saturated aqueous NaHCO$_3$ solution, extracted with CH$_2$Cl$_2$ (3×50 mL), washed with saturated aqueous NaCl solution (1×50 mL), dried through a cotton plug, and concentrated to yield a yellow oil (1.75 g, 100%). (TLC 50% EtOAc/hexanes R$_f$ 0.30); $^1$H NMR (400 MHz, CDCl$_3$) δ 7.26 (t, J=7.9 Hz; 2H), 7.05 (d, J=7.4 Hz, 1H), 7.01 (s, 1H), 6.84–6.78 (m, 4H), 3.77 (s, 3H), 3.76 (s, 3H), 3.52 (s, 2H), 2.83 (d, J=10.3 Hz, 2H), 2.58 (d, J=8.3 Hz, 2H), 2.36 (s, 2H), 1.75 (d, J=7.5 Hz, 2H), 1.41 (m, 2H); GCMS m/z 353 (M)$^+$; APCI MS m/z 354.4 (M+1)$^+$.

8-Chloro-3-(4-methoxy-benzyl)-8-(3-methoxy-phenyl)-3-aza-bicyclo[3.2.1]octane 3-(4-Methoxy-benzyl)-8-(3-methoxy-phenyl)-3-aza-bicyclo[3.2.1]octan-8-ol (1.48 g, 4.19 mmol) was dissolved in EtOAc (20 mL), charged with 2.5N HCl/EtOAc (6 mL), and azeotroped with MeOH (2×50 mL) to yield the HCl salt. This salt was slurried in CH$_2$Cl$_2$ (20 mL) and pyridine (0.34 mL, 4.19 mmol) then treated with thionyl chloride (0.92 mL, 12.6 mmol) dropwise, causing the dispersion to dissolve. The reaction was judged complete by TLC after 2 h, at which time it was carefully added to 1N NaOH (50 mL) at 0° C., bringing the final pH to 9. The product was extracted with CH$_2$Cl$_2$ (3×20 mL), washed with saturated aqueous NaCl solution (1×50 mL), filtered through a cotton plug and concentrated to brown oil. Flash chromatography provided a white solid (1.31 g, 84%). (TLC 40% EtOAc/hexanes R$_f$ 0.75); $^1$H NMR (400 MHz, CDCl$_3$) δ 7.23 (m, 3H), 7.04 (d, J=7.5 Hz, 1H), 6.99 (s, 1H), 6.84 (d, J=8.7 Hz, 2H), 6.79 (dd, J=7.9, 2.1 Hz, 1H), 3.78 (s, 6H), 3.53 (br s, 2H), 2.95 (d, J=10.3 Hz, 2H), 2.67 (br s, 2H), 2.65 (m, 2H), 1.79 (d, J=1.0 Hz, 2H), 1.45 (m, 2H); LCMS m/z 372.2 (M+1)$^+$; mp 99–102° C.

3-(4-Methoxy-benzyl)-8-(3-methoxy-phenyl)-3-aza-bicyclo[3.2.1]octane

8-Chloro-3-(4-methoxy-benzyl)-8-(3-methoxy-phenyl)-3-aza-bicyclo[3.2.1]octane (2.46 g, 6.61 mmol) and t-butanol (9.48 mL, 99.1 mmol) in dioxane (25 mL) was heated to a gentle reflux with an oil bath (110° C.). Sodium (1.52 g, 66.1 mmol) was pre-washed sequentially with hexanes/ethanol/THF/hexanes then added portionwise to the above refluxing mixture over 20 min. The reaction mixture was heated overnight then cooled to room temperature. To this was added methanol (50 mL) to quench residual sodium. The solvent was removed in vacuo, and the product was partitioned between water (100 mL) and EtOAc (100 mL). The layers were separated and the product was further extracted with EtOAc (3×40 mL), washed with saturated aqueous NaCl solution (1×50 mL), dried over Na$_2$SO$_4$, filtered and concentrated to a light brown oil. Flash chromatography provided the title compound (780 mg, 35%). (TLC 20% EtOAc/hexanes R$_f$ 0.60); $^1$H NMR (400 MHz, CDCl$_3$) δ 7.29 (d, J=8.7 Hz, 2H), 7.23 (t, J=7.7 Hz, 1H), 6.89 (d, J=8.7 Hz, 2H), 6.88 (m, 1H), 6.84 (s, 1H), 6.74 (dd, J=7.9, 2.5 Hz, 1H), 3.82 (s, 3H), 3.81 (s, 3H), 3.52 (s, 2H), 2.86 (dd, J=10.8, 3.7 Hz, 2H), 2.75 (s, 1H), 2.51 (br s, 2H), 2.28 (d, J=10.0 Hz, 2H), 1.79 (dd, J=12.7, 5.8 Hz, 2H), 1.63 (m, 2H); GCMS m/z 337 (M)$^+$.

8-(3-Methoxy-phenyl)-3-aza-bicyclo[3.2.1]octane 3-(4-Methoxy-benzyl)-8-(3-methoxy-phenyl)-3-aza-bicyclo[3.2.1]octane (104 mg, 0.31 mmol)) was dissolved in EtOAc (20 mL), charged with 2.5N HCl/EtOAc (4 mL), then azeotroped with MeOH (2×50 mL) to yield the HCl salt. This salt was dissolved in MeOH (3 mL) with piperidine (0.152 mL, 1.54 mmol), formic acid (0.035 mL, 0.924 mmol) and 20% Pd(OH)$_2$/C (Pearlman's catalyst, ~50 mg) then heated under a gentle reflux for 2 h (or until completion by TLC). The reaction mixture was filtered through a Celite pad, then azeotroped from MeOH/toluene until excess piperidine was removed to yield a white solid (102 mg, 100%). (TLC 20% MeOH/CH$_2$Cl$_2$, (NH$_3$) R$_f$ 0.45); $^1$H NMR (400 MHz, CD$_3$OD, HCl salt) δ 7.20 (t, J=7.9 Hz, 1H), 6.83 (d, J=7.9 Hz, 1H), 6.81 (s, 1H), 6.75 (dd, J=7.9, 2.5 Hz, 1H), 3.75 (s, 3H), 3.26 (AB m 4H), 3.13 (s, 1H), 2.75 (br s, 2H), 1.83 (m, 2H), 1.71 (m, 2H); GCMS m/z 217 (M)$^+$.

3-(3-Aza-bicyclo[3.2.1]oct-8-yl)-phenol 8-(3-Methoxy-phenyl)-3-aza-bicyclo[3.2.1]octane (162 mg, 0.638 mmol) was dissolved in glacial HOAc (2 mL), charged with hydrobromic acid (48%, 2 mL), then heated to a gentle reflux overnight (or until judged complete by TLC). The reaction was carefully poured onto 1N NaOH (30 mL); pH 14 was achieved. The product was extracted with n-butanol/toluene (3/1, 6×6 mL), washed with saturated aqueous NaCl solution (1×10 mL), dried over Na$_2$SO$_4$, and concentrated to yield a yellow semi-solid. To this was added 2.5N HCl/EtOAc (4 mL), then azeotroped from MeOH (2×10 mL) to yield the title compound as a yellow solid (130 mg, 85%). (TLC 10% MeOH/CH$_2$Cl$_2$, (NH$_3$) R$_f$ 0.10); $^1$H NMR (400 MHz, CD$_3$OD, HCl salt) δ 7.05 (t, J=7.9 Hz, 1H), 6.67 (d, J=7.9 Hz, 1H), 6.54 (s, 1H), 6.53 (dd, J=7.9, 2.3 Hz, 1H), 3.27 (ddd, J=3.3, 3.3, 1.7 Hz, 1H), 2.85 (d, J=12.9 Hz, 2H), 2.80 (dd, J=12.9, 3.1 Hz, 2H), 2.39 (br s, 2H), 1.67 (m, 2H), 1.57 (m, 2H); GCMS m/z 203 (M)$^+$; LCMS m/z 204.3 (M+1)$^+$.

Preparation 4

8-(3-Hydroxy-phenyl)-3-aza-bicyclo[3.2.1]octane-3-carboxylic acid benzyl ester 3-(3-Aza-bicyclo[3.2.1]oct-8-yl)-phenol as HCl salt (547 mg, 1.93 mmol) was stirred vigorously in 1N NaOH (10 mL), saturated aqueous Na$_2$CO$_3$ solution (20 mL) and CH$_2$Cl$_2$ (30 mL) then charged with benzyl chloroformate (5 mL, 35.0 mmol) slowly via syringe. After stirring overnight, the layers were separated and the product was extracted with CH$_2$Cl$_2$ (1×10 mL), washed with saturated aqueous NaHCO$_3$ solution, dried through a cotton plug and concentrated to a brown liquid. Flash chromatography provided the desired product as a thick clear oil (420 mg, 65%). (TLC 30% EtOAc/hexanes R$_f$ 0.34); $^1$H NMR (400 MHz, CDCl$_3$) δ 7.33 (m, 5H), 7.11 (t, J=7.9 Hz, 1H), 6.73 (d, J=7.9 Hz, 1H), 6.71 (s, 1H), 6.66 (d, J=7.9 Hz, 1H), 5.14 (s, 2H), 4.05 (dd, J=12.2, 2.7 Hz, 1H), 3.96 (dd, J=12.2, 2.7 Hz, 1H), 3.09 (m, 2H), 2.85 (s, 1H), 2.50 (br s, 1H), 2.46 (br s, 1H), 1.64 (m, 2H), 1.48 (m, 2H).

8-[3-(Trifluoro-methanesulfonyloxy)-phenyl]-3-aza-bicyclo[3.2.1]octane-3-carboxylic acid benzyl ester 8-(3-Hydroxy-phenyl)-3-aza-bicyclo[3.2.1]octane-3-carboxylic acid benzyl ester (420 mg, 1.24 mmol) was dissolved in CH$_2$Cl$_2$ (20 mL) with triethylamine (0.294 mL, 2.11 mmol) and N-phenyltrifluoromethanesulfonimide (0.67 g, 1.87 mmol). The reaction was judged complete by TLC after 4 h, then quenched with water (20 mL). The product was extracted with CH$_2$Cl$_2$ (3×20 mL), washed with 1N HCl (1×20 mL), water (1×20 mL), saturated aqueous NaCl solution (1×20 mL), filtered through a silica pad (2×3 in), eluted with 50% EtOAc/hexanes and concentrated to a semi-solid (800 mg, >100%). (TLC 50% EtOAc/hexanes R$_f$ 0.70); $^1$H NMR (400 MHz, CDCl$_3$) δ 7.54 (m, 2H), 7.35 (m, 3H), 7.25 (m, 2H), 7.09 (m, 2H), 5.13 (s, 2H), 4.08 (dd, J=10.0, 2.9 Hz, 1H), 4.00 (dd, J=12.0, 2.5 Hz, 1H), 3.13 (d, J=12.4 Hz, 1H), 3.07 (d, J=12.0, 1H), 2.93 (s, 1H), 2.54 (br s, 1H), 2.47 (br s, 1H), 1.60–1.49 (m, 4H); APCI m/z 470.0 (M+1)$^+$.

8-(3-Amino-phenyl)-3-aza-bicyclo[3.2.1]octane-3-carboxylic acid benzyl ester

8-[3-(Trifluoro-methanesulfonyloxy)-phenyl]-3-aza-bicyclo[3.2.1]octane-3-carboxylic acid benzyl ester (800 mg, theoretical amount 1.24 mmol) was azeotroped with THF (2×20 mL) then dissolved in anhydrous THF (10 mL) with benzophenone imine (0.260 mL, 1.55 mmol), cesium carbonate (606 mg, 1.86 mmol) and BINAP (racemic, 77 mg, 0.12 mmol). The reaction vessel was degassed (evac./$N_2$ purge 3×) before charging with palladium (II) acetate (28 mg, 0.12 mmol). The reaction was warmed to 80° C. 18 h, at which point it was judged complete by APCI MS. To this was added fresh THF (10 mL) followed by 2N HCl (5 mL) and this solution was allowed to stir at room temperature 30 min. The reaction mixture was neutralized with saturated aqueous $NaHCO_3$ solution. The product was extracted with EtOAc (3×30 mL), washed with saturated aqueous NaCl solution (1×30 mL), dried over $Na_2SO_4$ and concentrated to give the crude product. Flash chromatography provided the title compound as a thick yellow oil (236 mg, 57%). (TLC 30% EtOAc/hexanes $R_f$ 0.15). $^1$H NMR (400 MHz, $CDCl_3$) δ 7.35 (m, 2H), 7.30 (m, 3H), 7.10 (m, 1H), 6.65 (m, 1H), 6.55 (m, 2H), 5.15 (s, 2H), 4.07 (dd, J=12.5, 2.5 Hz, 1H), 3.99 (dd, J=12.5, 2.5 Hz, 1H), 3.13 (d, J=12.5 Hz, 1H), 3.08 (d, J=12.5 Hz, 1H), 2.86 (s, 1H), 2.55 (brs, 1H), 2.48 (br s, 1H), 1.69 (m, 2H), 1.52 (m, 2H). APCI MS m/z 338.1 $(M+1)^+$; 378.3 $(M+CH_3CN)^+$.

8-(3-Methanesulfonylamino-phenyl)-3-aza-bicyclo[3.2.1]octane-3-carboxylic acid benzyl ester 8-(3-Amino-phenyl)-3-aza-bicyclo[3.2.1]octane-3-carboxylic acid benzyl ester (185 mg, 0.55 mmol) was dissolved in pyridine (3 mL), cooled to 0° C. then charged with methanesulfonylchloride (0.064 mL, 0.825 mmol) dropwise, causing a color change from yellow to bright orange. The reaction was warmed to room temperature and judged complete by APCI MS after 1 h. Following a 1N HCl quench (10 mL), the product was extracted with EtOAc (2×30 mL), washed with saturated aqueous $NaHCO_3$ solution (1×30 mL), saturated aqueous NaCl solution (1×30 mL), dried over $Na_2SO_4$, filtered and concentrated to give an orange liquid (153 mg, 67%). (TLC 30% EtOAc/hexanes $R_f$ 0.15); $^1$H NMR (400 MHz, $CDCl_3$) δ 7.33–7.19 (m, 5H), 7.21 (t, J=7.9 Hz, 1H), 7.14 (s, 1H), 7.05 (d, J=7.9 Hz, 1H), 6.99 (d, J=7.9 Hz, 1H), 5.24 (s, 2H), 4.03 (d, J=12.5 Hz, 1H), 3.94 (d, J=12.6 Hz, 1H), 3.07 (d, J=12.5 Hz, 1H), 3.03 (d, J=12.5 Hz, 1H), 2.90 (s, 3H), 2.86 (s, 1H), 2.50 (br s, 1H), 2.44 (br s, 1H), 1.60 (m, 2H), 1.47 (m, 2H); APCI MS m/z 415.1 $(M+1)^+$.

N-[3-(3-Aza-bicyclo[3.2.1]oct-8-yl)-Phenyl]-methanesulfonamide 8-(3-Methanesulfonylamino-phenyl)-3-aza-bicyclo[3.2.1]octane-3-carboxylic acid benzyl ester (153 mg, 0.370 mmol) in MeOH (10 mL) was placed in a 250 mL Parr bottle with charged with 20% $Pd(OH)_2$/C (Pearlman's, 20 mg) and shaken under hydrogen at 40 psi overnight Budged complete by APCI MS). The reaction was filtered through a Celite pad, rinsed with MeOH and concentrated to a yellow semi-solid. This free amine product was dissolved in EtOAc (6 mL), then azeotroped from 2.5N HCl/EtOAc (1×4 mL) then MeOH (2×20 mL) to yield the HCl salt of the title compound as a yellow solid (80 mg, 68%). $^1$H NMR (400 MHz, $CD_3OD$, HCl salt) δ 7.26 (m, 1H), 7.17 (s, 1H), 7.07 (d, J=8.3 Hz, 1H), 7.05 (d, J=8.3 Hz, 1H), 3.26 (s, 4H), 3.17 (s, 1H), 2.88 (s, 3H), 2.76 (br s, 2H), 1.83 (br s, 2H), 1.72 (d, J=8.3 Hz, 2H); APCI MS m/z 281.1 $(M+1)^+$.

Preparation 5

3-Benzyl-8-(3-bromo-phenyl)-8-hydroxy-3-aza-bicyclo[3.2.1]octane 1,3-Dibromobenzene (20.2 ml, 167 mmol) in anhydrous ether (100 ml) in a flame dried 1LRB flask, at −78° C. was treated with a 2.5M solution of n-butyllithium in hexanes (58 ml, 145 mmol) via an addition funnel over 20 min. After 1 h at −78° C., the mixture was treated with a solution of 3-benzyl-3-aza-bicyclo[3.2.1]octan-8-one (18.0 g, 83.6 mmol) in anhydrous ether (100 ml) via addition funnel over 20 min. The reaction stirred at −78° C. 30 min, warmed to room temperature and judged complete by TLC. The reaction solution was quenched with saturated aqueous $NH_4Cl$ solution (200 ml) and stirred 18 h. The layers were separated and the aqueous layer extracted with ether (2×100 ml). The organic layer was washed with saturated aqueous $Na_2CO_3$ solution (150 mL), saturated aqueous NaCl solution (100 ml), dried over $Na_2SO_4$, filtered and concentrated to a dark oil. Passage through a silica pad (3×8 in) eluted with 5% EtOAc/hexanes yielded a light yellow oil (31 g, 100%). (TLC 20% EtOAc/hexanes $R_f$ 0.21); $^1$H NMR (400 MHz, $CDCl_3$) δ 7.61 (s, 1H), 7.41–7.19 (m, 8H), 3.58 (s, 2H), 2.83 (d, J=10.4 Hz, 2H), 2.60 (d, J=8.3 Hz, 2H), 2.35 (br s, 2H), 1.80 (d, J=7.5 Hz, 2H), 1.39 (m, 2H); APCI MS m/z 372.1, 374.1 $(M+1)^+$.

3-Benzyl-8-(3-phenyl boronic acid-)-8-hydroxy-3-aza-bicyclo[3.2.1]octane

3-Benzyl-8-(3-bromo-phenyl)-3-aza-bicyclo[3.2.1]octan-8-ol (0.737 g, 1.98 mmol) in THF (10 mL), at −78° C. was treated with a 2.5M solution of n-butyllithium in hexanes (0.87 mL, 2.18 mmol) dropwise. After 1 h at −78° C., the solution was warmed to 10° C. It was determined by TLC that starting material was still present. The mixture was re-cooled to −78° C. and re-treated with an additional 1.1 equivalents of the 2.5M solution of n-butyllithium in hexanes (0.871 mL, 2.18 mmol). After 20 min, starting material was judged to be consumed by APCI MS. The reaction was treated with triisopropylborate (1.10 mL, 4.74 mmol), then allowed to warm to room temperature. After 20 min the reaction was quenched with water (10 mL) and 1N HCl (2 mL) to bring the final pH to 8. The product was extracted with EtOAc (3×10 mL), washed with saturated aqueous NaCl solution (1×10 mL), dried over $Na_2SO_4$, filtered and concentrated to yield the title product (521 mg, 78%). (TLC 50% EtOAc/hexanes $R_f$ 0.15); APCI MS m/z 338.2 $(M+1)^+$.

3-Benzyl-8-(3-hydroxy-phenyl)-3-aza-bicyclo[3.2.1]octan-8-ol

3-Benzyl-8-(3-phenyl boronic acid-)-8-hydroxy-3-aza-bicyclo[3.2.1]octane (521 mg, 1.55 mmol) in THF (15 mL) and 4-methylmorpholine N-oxide (313 mg, 2.32 mmol) were heated to reflux in an oil bath for 2 h (or until judged complete by APCI MS). After cooling to room temperature, the reaction was quenched with 1N HCl (10 mL), washed with ether (2×20 mL), and the organic layer was back extracted with water (1×10 mL). The combined aqueous layers were neutralized with saturated aqueous $NaHCO_3$ solution. The product was extracted with EtOAc (3×20 mL), washed with saturated aqueous NaCl solution (1×20 mL), dried over $Na_2SO_4$, filtered and concentrated to give the crude product. Flash chromatography provided product as a yellow semi-solid (210 mg, 44%). (TLC 80% EtOAc/hexanes $R_f$ 0.56); $^1$H NMR (400 MHz, $CDCl_3$) δ 7.36–7.15 (m, 6H), 6.99 (d, J=7.9 Hz, 1H), 6.90 (br s, 1H), 6.72 (dd, J=7.9, 2.1 Hz, 1H), 3.59 (s, 2H), 2.85 (d, J=10.4 Hz, 2H), 2.61 (dd, J=10.4, 3.1 Hz, 2H), 2.32 (br s, 2H), 1.76 (d, J=7.5 Hz, 2H), 1.39 (m, 2H); APCI MS m/z 310.2 $(M+1)^+$.

8-(3-Hydroxy-phenyl)-3-aza-bicyclo[3.2.1]octan-8-ol

3-Benzyl-8-(3-hydroxy-phenyl)-3-aza-bicyclo[3.2.1]octan-8-ol (210 mg, 0.607 mmol) was dissolved in EtOAc (20 mL), charged with 2.5 N HCl/EtOAc (4 mL), then azeotroped with MeOH (2×50 mL) to yield the HCl salt. This salt was dissolved in MeOH (10 mL) in a 250 mL parr bottle. To this was added 20% Pd(OH)$_2$/C (Pearlman's catalyst, 35 mg) and the mixture was shaken under 45 psi of H$_2$ overnight, at which point it was judged to be 50% complete by APCI MS. The reaction was filtered through a Celite pad, concentrated and re-subjected with an additional catalyst load (35 mg) in MeOH (10 mL) and shaken under 45 psi at 50° C. over the weekend. The reaction was filtered through a Celite pad and concentrated to afford the crude product (180 mg, >100%); $^1$H NMR (400 MHz, CD$_3$OD, HCl salt) δ 7.18 (t, J=7.9 Hz, 1H), 6.97 (d, J=7.9 Hz, 1H), 6.94 (s, 1H), 6.72 (dd, J=7.9, 2.0 Hz, 1H), 3.77 (d, J=12.0 Hz, 2H), 3.10 (m, 2H), 2.62 (br s, 2H), 1.66 (m, 4H); APCI MS m/z 220.2 (M+1)$^+$.

Preparation 6

8-(3-Amino-phenyl)-3-benzyl-3-aza-bicyclo[3.2.1]octan-8-ol

3-Benzyl-8-(3-bromo-phenyl)-3-aza-bicyclo[3.2.1]octan-8-ol (4.69 g, 7.82 mmol) was dissolved in toluene (40 mL) in a flame dried RB flask. To this was added benzophenone imine (1.57 mL, 9.38 mmol), sodium t-butoxide (1.05 g, 11.0 mmol), then BINAP (racemic, 0.487 g, 0.782 mmol). The reaction was degassed (evac./N$_2$ purged 3×) before adding palladium II acetate (0.175 g, 0.782 mmol), then heated to 100° C. in an oil bath under N$_2$ overnight (or until judged complete by TLC). The imine was cooled to room temperature, treated with 6 N HCl (25 mL), and heated to 100° C. After 1 h, the reaction was cooled to room temperature, filtered through a Celite pad, rinsed with ether (50 mL) then water (50 mL). The filtrate was washed with ether (2×100 mL), then the aqueous layer was basified to pH 10 with 1 N NaOH, and saturated aqueous Na$_2$CO$_3$ solution. The product was extracted with EtOAc (3×100 mL), washed with saturated aqueous NaCl solution (1×100 mL), dried over Na$_2$SO$_4$, filtered through a Silica pad (2×3 in) eluted with 100% EtOAc and concentrated to an orange foam (2.34 g, 97%). (TLC 50% EtOAc/hexanes R$_f$ 0.30); $^1$H NMR (400 MHz, CDCl$_3$) δ 7.38–7.20 (m, 5H), 7.12 (t, J=7.9 Hz, 1H), 6.86 (d, J=7.9 Hz, 1H), 6.79 (s, 1H), 6.59 (m, 1H), 3.64–3.57 (m, 2H–NH$_2$, 2H), 2.85 (d, J=9.9 Hz, 2H), 2.58 (m, 2H), 2.34 (br s, 2H), 1.77 (d, J=7.1 Hz, 2H), 1.43 (m, 2H); APCI MS m/z 309.2 (M+1)$^+$.

N-{3-[8-Hydroxy-3-(4-methoxy-benzyl)-3-aza-bicyclo[3.2.1]oct-8-yl]-phenyl}-methanesulfonamide 8-(3-Amino-phenyl)-3-(4-methoxy-benzyl)-3-aza-bicyclo[3.2.1]octan-8-ol (2.11 g, 6.23 mmol) in pyridine (15 mL) at 0° C. was charged with methanesulfonylchloride (0.72 mL, 9.35 mmol) dropwise. The reaction was warmed to room temperature and judged complete by TLC after 3 h. Following a water addition (20 mL), the product was extracted with EtOAc (4×30 mL), the organic layer was washed with saturated aqueous NaCl solution (6×50 mL), dried over Na$_2$SO$_4$, filtered and concentrated to give a crude orange liquid. Flash chromatography provided the title compound as a yellow semi-solid (1.28 g, 49%). (TLC 50% EtOAc/Hexanes R$_f$ 0.24); 400 MHz $^1$H NMR (400 MHz, CDCl3) δ 7.30 (d, J=8.7 Hz, 2H), 7.27 (m, 3H), 7.14 (dd, J=7.1, 2.1 Hz, 1H), 6.83 (d, J=8.7 Hz, 2H), 3.77 (s, 3H), 3.53 (m, 2H), 2.96 (s, 3H), 2.82 (m, 2H), 2.60 (m, 2H), 2.36 (br s, 2H), 1.78 (m, 2H), 1.36 (m, 2H); APCI MS m/z 417.1 (M+1)$^+$; LCMS m/z 417.1 (M+1)$^+$.

N-[3-(8-Hydroxy-3-aza-bicyclo[3.2.1]oct-8-yl)-phenyl]-methanesulfonamide

N-{3-[8-Hydroxy-3-(4-methoxy-benzyl)-3-aza-bicyclo[3.2.1]oct-8-yl]-phenyl}-methanesulfonamide (0.505 g, 1.21 mmol) was dissolved in EtOAc (20 mL), charged with 2.5 N HCl/EtOAc (4 mL), and azeotroped with MeOH (2×50 mL) to yield the HCl salt. This salt was dissolved in MeOH (6 mL) then treated with a solution of formic acid (0.14 mL, 3.64 mmol) and piperidine (0.60 mL, 6.06 mmol) and 20% Pd(OH)$_2$/C (Pearlman's catalyst, ~100 mg) then heated to 65° C. for 2 h (or until judged complete by TLC). The reaction mixture was filtered through a Celite pad, concentrated, and azeotroped from MeOH (2×50 mL) to provide the crude product. $^1$H NMR (400 MHz, CD$_3$OD, HCl salt) δ 7.37 (s, 1H), 7.32 (m, 2H), 7.18 (d, J=7.9 Hz, 1H), 3.78 (d, J=12.1 Hz, 2H), 3.29 (d, J=12.1 Hz, 2H), 2.92 (s, 3H), 2.67 (br d, 2H), 1.72 (m, 2H), 1.53 (m, 2H).

Preparation 7

3-(3-Benzyl-8-hydroxy-3-aza-bicyclo[3.2.1]oct-8-yl)-benzonitrile

3-Benzyl-8-(3-bromo-phenyl)-3-aza-bicyclo[3.2.1]octan-8-ol (2.17 g, 5.83 mmol) and zinc cyanide (1.03 g, 8.75 mmol) were combined in DMF (30 mL), degassed (evac/N$_2$ purge 3×) then charged with tetrakistriphenylphosphine palladium (0) (3.37 g, 2.91 mmol). The resulting reaction mixture was heated to 85 □ C. in an oil bath for 5 h (or until complete by TLC). After cooling to room temperature, the reaction mixture was filtered through a Celite pad and rinsed with EtOAc. The filtrate was extracted with 1 N HCl (2×50 mL) then neutralized to pH 8 with 1 N NaOH and saturated aqueous NaHCO$_3$ solution, causing an emulsion to form. The product was extracted with EtOAc (3×100 mL), washed with saturated aqueous NaCl solution (2×100 mL), dried over Na$_2$SO$_4$, filtered and concentrated. The resulting crude product was dissolved in ether (100 mL), washed with 50% saturated aqueous NaCl solution (4×100 mL), dried over Na$_2$SO$_4$, filtered and concentrated to a brown oil (1.86 g, 100%). (TLC 40% EtOAc/Hexanes R$_f$ 0.42); $^1$H NMR (400 MHz, CDCl$_3$) δ 7.76–7.72 (m, 2H), 7.55 (br d, J=7.9 Hz, 1H), 7.45 (t, J=7.9 Hz, 1H), 7.36–7.20 (m, 5H), 3.59 (br s, 2H), 2.84 (d, J=10.8 Hz, 2H), 2.61 (br d, J=10.8 Hz, 2H), 2.36 (br, s, 2H), 1.83 (d, J=7.5 Hz, 2H), 1.35 (m, 2H); APCI MS m/z 319.2 (M+1)$^+$.

3-(3-Benzyl-8-hydroxy-3-aza-bicyclo[3.2.1]oct-8-yl)-benzamide 3-(3-Benzyl-8-hydroxy-3-aza-bicyclo[3.2.1]oct-8-yl)-benzonitrile (1.86 g, 5.84 mmol) in DMSO (30 mL) with potassium carbonate (0.121 g, 0.88 mmol) was charged with 30% aqueous hydrogen peroxide (2.98 mL, 29.2 mmol) and allowed to stir at room temperature for 2 h (or until judged complete by TLC). The reaction was cooled in an ice bath then quenched with water (50 mL) causing the product precipitate as white solids. The mixture was acidified to pH 1 with 1N HCl (25 mL) to dissolve the product and the aqueous layer was washed with ether (2×30 mL). The ether extracts were back extracted with water (1×30 mL). The combined acidic aqueous layers were neutralized to pH 8 with saturated aqueous NaHCO$_3$ solution. The product was extracted with EtOAc (3×50 mL), washed with 50% saturated aqueous NaCl solution (3×50 mL) then dried by azeotroping with THF (3×100 mL) yielding a white solid (1.69 g, 86%). $^1$H NMR (400 MHz, CD$_3$OD) δ 7.96 (t, J=1.5 Hz, 1H), 7.95 (d, J=7.9 Hz, 1H), 7.64 (d, J=7.4 Hz, 1H), 7.41–7.15 (m, 6H), 3.56 (br s, 2H), 2.88 (m, 2H), 2.61 (m, 2H), 2.46 (br, s, 2H), 1.76 (m, 2H), 1.35 (m, 2H); APCI MS m/z 337.2 (M+1)$^+$; mp 210–214° C.

3-(8-Hydroxy-3-aza-bicyclo[3.2.1]oct-8-yl)-benzamide 3-(3-Benzyl-8-hydroxy-3-aza-bicyclo[3.2.1]oct-8-yl)-benzamide (1.38 g, 4.10 mmol) was dissolved in EtOAc (20 mL), charged with 2.5 N HCl/EtOAc (4 mL), then azeotroped with MeOH (2×50 mL) to yield the HCl salt. This salt was dissolved in MeOH (20 mL) in a 250 mL parr bottle. To this was added 20% Pd(OH)$_2$/C (Pearlman's catalyst, 35 mg) and the mixture was shaken under 45 psi of H$_2$ overnight., at which point it was 25% complete by APCI MS. The reaction was re-subjected and shaken under 45 psi at 60° C. overnight. The reaction solution was filtered through a Celite pad and concentrated to afford the crude product (1.35 g). $^1$H NMR (400 MHz, CD$_3$OD, HCl salt) δ 8.02 (s, 1H), 7.80 (d, J=7.5 Hz, 1H), 7.70 (d, J=7.7 Hz, 1H), 7.47 (m, 1H), 3.79 (d, J=11.6 Hz, 2H), 3.12 (d, J=10.3 Hz, 2H), 2.72 (br s, 2H), 1.67–1.76 (m, 4H); APCI MS m/z 247.2 (M+1)$^+$.

Preparation 8

2-Methoxy-ethanesulfonic acid [3-(3-benzyl-8-hydroxy-3-aza-bicyclo[3.2.1]oct-8-yl)-phenyl]-amide 8-(3-Amino-phenyl)-3-benzyl-3-aza-bicyclo[3.2.1]octan-8-ol (1.63 g, 5.28 mmol) stirred in pyridine (20 ml) at 0° C. was charged with 2-methoxy-ethanesulfonyl chloride (1.26 g, 7.93 mmol) dropwise causing a color change from yellow to bright orange. The reaction was warmed to room temperature and judged complete by TLC after 1 h. Following addition of water (20 ml), the product was extracted with EtOAc (4×30 ml), washed with saturated aqueous NaCl solution (6×30 ml), dried over Na$_2$SO$_4$, filtered and concentrated to a crude red oil (2.37 g, >100%). $^1$H NMR (400 MHz, CDCl$_3$) δ 7.35–7.10 (m, 4H), 3.78 (ddd, J=7.5, 3.3, 2.1 Hz, 2H), 3.59 (s, 2H), 3.36 (d, J=2.5 Hz, 3H), 3.17, (m, 2H), 2.85 (d, J=16.3 Hz, 3H), 2.61 (d, J=8.3 Hz, 2H), 2.36 (s, 2H), 1.79 (d, J=7.0 Hz, 2H), 1.37 (d, J=10.0 Hz, 2H); APCI MS m/z 431.2 (M+1)$^+$.

2-Methoxy-ethanesulfonic acid [3-(8-hydroxy-3-aza-bicyclo[3.2.1]oct-8-yl)-phenyl]-amide 2-Methoxy-ethanesulfonic acid [3-(3-benzyl-8-hydroxy-3-aza-bicyclo[3.2.1]oct-8-yl)-phenyl]-amide (2.30 g, 5.34 mmol) was dissolved in EtOAc (20 ml), charged with 2.5 N HCl/EtOAc (6 ml), then azeotroped with MeOH (2×50 ml) to yield the HCl salt. This salt was dissolved in MeOH (20 ml) in a 250 ml Parr bottle. To this was added 20% Pd(OH)$_2$/C (Pearlman's catalyst, 25 mg) and the mixture was shaken under 45 psi of H$_2$ overnight or until judged complete by APCI MS. The reaction was filtered through a Celite pad and concentrated to afford the crude product as a green foam (1.88 g, >100%). $^1$H NMR (CD$_3$OD, HCl salt) δ 7.42 (s, 1H), 7.31 (m, 2H), 7.15 (dd, J=7.5, 1.6 Hz, 1H), 3.78 (d, J=11.6 Hz, 2H), 3.70 (t, J=6.0 Hz, 2H), 3.26 (m, 2H), 3.24 (s, 3H), 3.11(dd, J=11.6, 2.1 Hz, 2H), 2.62 (br s, 2H), 1.72 (m, 4H); APCI MS m/z 341.2 (M+1)$^+$. C$_{16}$H$_{24}$N$_2$O$_4$S Preparation 9

3-Benzyl-8-(3-bromo-phenyl)-8-methoxy-3-aza-bicyclo[3.2.1]octane 1,3-Dibromobenzene (12.4 ml, 0.102 mol) in anhydrous ether (200 ml) in a flame dried 1LRB flask, at −78° C. was treated with a 2.5M solution of n-butyllithium in hexanes (41.0 ml, 0.102 mol) via addition funnel over 15 min. After 1 h at −78° C., the mixture was treated with a suspension of 3-benzyl-3-aza-bicyclo[3.2.1]octan-8-one (11.02 g, 51.2 mmol) in anhydrous ether (100 ml) via addition funnel over 20 min. The reaction stirred at −78° C. 45 min, warmed to room temperature and judged complete by TLC. The reaction solution was carefully concentrated in vacuo under N$_2$ to remove ~250 mL of ether. The reaction slurry was charged with 250 ml of fresh anhydrous THF, followed by iodomethane (9.56 ml, 0.154 mol) and allowed to stir at room temperature for 60 h. After quenching with 1 N HCl (100 ml to pH 1), the layers were separated, then extracted with ether (2×100 ml). The acidic aqueous layer was basified with saturated aqueous Na$_2$CO$_3$ solution to pH 11, and extracted with EtOAc (2×100 ml). All organic extracts were combined, washed with saturated aqueous Na$_2$CO$_3$ solution (1×100 ml), saturated aqueous NaCl solution (1×100 ml), dried over Na$_2$SO$_4$, filtered and concentrated to a dark oil. Passage through a Silica pad (3×8 in) eluted with 5% EtOAc/hexanes yielded a light yellow oil (22.4 g, >100%). (TLC 20% EtOAc/Hexanes R$_f$ 0.70); $^1$H NMR (400 MHz, CDCl$_3$) δ 7.55 (s, 1H), 7.41–7.19 (m, 8H), 3.60 (s, 2H), 2.84 (s, 3H), 2.75 (d, J=9.9 Hz, 2H), 2.53 (d, J=7.9 Hz, 2H), 2.43 (br s, 2H), 1.80 (d, J=7.5 Hz, 2H), 1.38 (m, 2H); APCI MS m/z 386.1, 388.1 (M+1)$^+$.

3-Benzyl-8-(3-phenylboronic acid)-8-methoxy-3-aza-bicyclo[3.2.1]octane

3-Benzyl-8-(3-bromo-phenyl)-8-methoxy-3-aza-bicyclo[3.2.1]octane (0.76 g, 1.97 mmol) in THF (10 ml), at −78° C. was treated with a 2.5M solution of n-butyllithium in hexanes (0.87 ml, 2.16 mmol). After stirring 1 h at −78° C., there was no starting material by APCI MS. The reaction was treated with triisopropylborate (0.55 ml, 2.36 mmol), and allowed to warm to 0° C., when it was quenched with water (10 ml) and 1N HCl (2 ml) to bring the final pH to 8. The product was extracted with EtOAc (3×10 ml), washed with saturated aqueous NaCl solution (1×10 ml), dried over Na$_2$SO$_4$, filtered and concentrated to give a yellow solid (510 mg, 74%). (TLC 20% EtOAc/Hexanes R$_f$ 0.15); APCI MS m/z 352.2 (M+1)$^+$.

3-(3-Benzyl-8-methoxy-3-aza-bicyclo[3.2.1]oct-8-yl)-phenol

The boronic acid (510 mg, 1.45 mmol) from above in THF (15 ml) and 4-methylmorpholine N-oxide (294 mg, 2.18 mmol) was heated to reflux in an oil bath overnight. After cooling to room temperature, the reaction was quenched with water (20 ml). The product was extracted with EtOAc (3×20 ml), washed with saturated aqueous NaCl solution (1×20 ml), dried over Na$_2$SO$_4$, filtered and concentrated to the crude product. Flash chromatography provided the desired product (158 mg, 34%). (TLC 60% EtOAc/Hexanes R$_f$ 0.45); $^1$H NMR (400 MHz, CDCl$_3$) δ 7.38–7.17 (m, 6H), 6.98 (d, J=7.9 Hz, 1H), 6.93 (br s, 1H), 6.77 (dd, J=7.9, 1.6 Hz, 1H), 3.60 (s, 2H), 2.89 (s, 3H), 2.79 (d, J=10.0 Hz, 2H), 2.58 (m, 2H), 2.46 (br s, 2H), 1.79 (d, J=7.9 Hz, 2H), 1.43 (m, 2H); APCI MS m/z 324.2 (M+1)$^+$.

3-(8-Methoxy-3-aza-bicyclo[3.2.1]oct-8-yl)-phenol 3-(3-Benzyl-8-methoxy-3-aza-bicyclo[3.2.1]oct-8-yl)-phenol (158 mg, 0.488 mmol) was dissolved in EtOAc (20 ml), charged with 2.5 N HCl/EtOAc (4 ml), then azeotroped with MeOH (2×50 ml) to yield the HCl salt. This salt was dissolved in MeOH (10 ml) in a 250 ml Parr bottle. To this was added 20% Pd(OH)$_2$/C (Pearlman's catalyst, 25 mg) and the mixture was shaken under 45 psi of H$_2$ overnight or until judged complete by APCI MS. The reaction was filtered through a Celite pad and concentrated to afford the crude product as a clear oil (150 mg, >100%). $^1$H NMR (400 MHz, CD$_3$OD, HCl salt) δ 7.18 (m, 1H), 6.89 (m, 1H), 6.77

(m, 1H), 3.61 (d, J=10.0, Hz, 2H), 3.10 (m, 2H), 2.87 (br s, 3H), 2.74 (br s, 2H), 1.79–1.68 (m, 4H); APCI MS m/z 234.2 (M+1)$^+$.

Preparation 10

3-Benzyl-8-(3-aniline)-8-methoxy-3-aza-bicyclo[3.2.1]octane

3-Benzyl-8-(3-bromo-phenyl)-8-methoxy-3-aza-bicyclo[3.2.1]octane (4.69 g, 12.1 mmol), benzophenone imine (2.45 ml, 14.5 mmol), sodium t-butoxide (1.63 g, 16.9 mol) and BINAP (racemic, 754 mg, 1.21 mmol) were combined in toluene (100 ml). The reaction vessel was degassed (evac./N$_2$ purged 3×) before adding palladium (II) acetate (0.272 g, 1.21 mmol), and heated to 100° C. in an oil bath under N$_2$ over 60 h (or until judged complete by TLC). The reaction mixture was cooled to room temperature, filtered through a Celite pad, eluted with EtOAc, then concentrated to a brown oil. This imine was diluted with THF (50 ml) then treated with 6 N HCl (25 ml) and allowed to stir at room temperature 2 h (or until complete by TLC). The reaction was washed with ether (2×100 ml), the aqueous layer was then basified to pH 10 with 1N NaOH and saturated aqueous Na$_2$CO$_3$ solution. The product was extracted with EtOAc (3×100 ml), washed with saturated aqueous NaCl solution (1×100 ml), dried over Na$_2$SO$_4$, filtered through a silica pad (2×3 in), eluted with 100% EtOAc, and concentrated to dark red oil (3.65 g, 93%). (TLC 100% EtOAc R$_f$ 0.60); $^1$H NMR (400 MHz, CDCl$_3$) δ 7.45–7.21 (5H), 7.10 (t, J=7.9 Hz, 1H), 6.81 (d, J=7.9 Hz, 1H), 6.80 (br s, 1H), 6.59 (ddd, J=7.9, 2.1, 0.8 Hz, 1H), 3.61–3.58 (2H+NH$_2$), 2.85 (s, 3H), 2.76 (d, J=10.0 Hz, 2H), 2.54 (br d, 2H), 2.43 (br, s, 2H), 1.78 (d, J=7.4 Hz, 2H), 1.43 (m, 2H); mp 131–134° C.

N-[3-(3-Benzyl-8-methoxy-3-aza-bicyclo[3.2.1]oct-8-yl)-phenyl]-methanesulfonamide 3-Benzyl-8-(3-aniline)-8-methoxy-3-aza-bicyclo[3.2.1]octane (2.98 g, 9.24 mol) in CH$_2$Cl$_2$ (10 ml) and pyridine (20 ml) at 0° C. was charged with methanesulfonylchloride (1.07 ml, 13.9 mol) dropwise, causing a color change from yellow to bright orange. The reaction was warmed to room temperature and judged complete by TLC after 1 h. Following a water quench (20 ml), the product was extracted with EtOAc (4×30 ml), washed with saturated aqueous NaCl solution (6×30 ml), dried over Na$_2$SO$_4$, filtered and concentrated to a crude orange liquid. Flash chromatography provided the title compound as a yellow semi-solid (2.59 g, 70%). $^1$H NMR (400 MHz, CDCl$_3$) δ 7.38–7.16 (m, 9H), 3.57 (br s, 2H), 2.97 (s, 3H), 2.83 (s, 3H), 2.75 (d, J=9.4 Hz, 2H), 2.54 (d, J=9.4 Hz, 2H), 2.45 (br s, 2H), 1.80 (d, J=7.5 Hz, 2H), 1.37 (m, 2H).

N-[3-(8-Methoxy-3-aza-bicyclo[3.2.1]oct-8-yl)-phenyl]-methanesulfonamide

N-[3-(3-Benzyl-8-methoxy-3-aza-bicyclo[3.2.1]oct-8-yl)-phenyl]-methanesulfonamide (1.38 g, 3.45 mmol) was dissolved in EtOAc (20 ml), charged with 2.5 N HCl/EtOAc (6 ml), stripped in vacuo then azeotroped with MeOH (2×50 ml) to yield the HCl salt. This salt was dissolved in MeOH (15 ml) in a 500 ml Parr bottle. To this was added 20% Pd(OH)$_2$/C (Degussa type, 200 mg) and the mixture was shaken under 50 psi of H$_2$ at 50° C. overnight. The reaction was not complete (TLC). It was re-dosed with additional catalyst (100 mg) and re-subjected to identical conditions overnight. The reaction was filtered through a Celite pad and concentrated to afford the crude product (0.78 g, 65%). $^1$H NMR (400 MHz, CD$_3$OD, HCl salt) δ 7.35–7.18 (m, 4H), 3.42 (d, J=12.5 Hz, 2H), 2.90 (s, 3H), 2.88 (s, 3H), 2.72 (dd, J=12.5, 2.9 Hz, 2H), 2.53 (br s, 2H), 1.70–1.59 (m, 4H); APCI MS m/z 311.3 (M+1)$^+$.

Preparation 11

[3-(3-Benzyl-8-methoxy-3-aza-bicyclo[3.2.1]oct-8-yl)-phenyl]-(2-methanesulfonyl-ethyl)-amine 3-Benzyl-8-(3-aniline)-8-methoxy-3-aza-bicyclo[3.2.1]octane (542 mg, 1.68 mmol) stirred in pyridine (5 ml) at 0° C. was charged with 2-methoxy-ethanesulfonyl chloride (0.40 g, 2.52 mmol) dropwise causing a color change from yellow to bright orange. The reaction was warmed to room temperature and judged complete by TLC after 1 h. Following addition of water (20 ml), the product was extracted with EtOAc (4×30 ml), washed with saturated aqueous NaCl solution (6×30 ml), dried over Na$_2$SO$_4$, filtered and concentrated to a crude orange liquid (800 mg, >100%). $^1$H NMR (400 MHz, CDCl$_3$) δ 7.18–7.39 (m, 9H), 3.79 (t, J=5.4 Hz, 2H), 3.57 (s, 2H), 3.38 (s, 3H), 3.17 (t, J=5.4 Hz, 2H), 2.83 (s, 3H), 2.75 (d, J=9.6 Hz, 2H), 2.54 (br s, 2H), 2.44 (br s, 2H), 1.79 (d, J=7.1 Hz, 2H), 1.56 (s, 2H); APCI MS m/z 445.3 (M+1)$^+$.

2-Methoxy-ethanesulfonic acid [3-(8-methoxy-3-aza-bicyclo[3.2.1]oct-8-yl)-phenyl]-amide

[3-(3-Benzyl-8-methoxy-3-aza-bicyclo[3.2.1]oct-8-yl)-phenyl]-(2-methanesulfonyl-ethyl)-amine (3.01 g, 5.09 mmol) was dissolved in EtOAc (20 ml), charged with 2.5 N HCl/EtOAc (6 ml), then azeotroped with MeOH (2×50 ml) to yield the HCl salt. This salt was dissolved in MeOH (20 ml) in a 250 ml Parr bottle. To this was added 20% Pd(OH)$_2$/C (Pearlman's catalyst, 25 mg) and the mixture was shaken under 45 psi of H$_2$ overnight or until judged complete by APCI MS. The reaction was filtered through a Celite pad and concentrated to afford the crude product as a green foam (3.00 g, >100%). $^1$H NMR (400 MHz, CD$_3$OD, HCl salt) δ 7.37 (m, 2H), 7.26 (d, J=7.9 Hz, 1H), 7.22 (dd, J=7.9, 1.3 Hz, 1H), 3.71 (t, J=6.0 Hz, 2H), 3.63 (d, J=12.1 Hz, 2H), 3.26 (s, 4H), 3.24 (s, 3H), 2.90 (s, 3H), 2.78 (br s, 2H), 1.75 (m, 2H), 1.66 (m, 2H); APCI MS m/z 401.3 (M+1)$^+$.

Preparation 12

3-Benzyl-8-(3-cyano-phenyl)-8-methoxy-3-aza-bicyclo[3.2.1]octane

3-Benzyl-8-(3-bromo-phenyl)-8-methoxy-3-aza-bicyclo[3.2.1]octane (2.17 g, 5.62 mmol) and zinc cyanide (0.99 g, 8.43 mmol) were combined in DMF (30 ml), degassed (evac./N$_2$ purge 3×) then charged with tetrakis(triphenylphosphine) palladium (0) (3.24 g, 2.81 mmol). The resulting reaction mixture was heated to 85° C. in an oil bath for 5 h. Upon cooling to room temperature, the reaction mixture was filtered through a Celite pad and rinsed with EtOAc. The filtrate was extracted with 1 N HCl (2×50 ml) then neutralized to pH 8 with 1 N NaOH and saturated aqueous NaHCO$_3$, causing an emulsion to form. The product was extracted with EtOAc (3×100 ml), washed with saturated aqueous NaCl solution (2×100 ml), dried over Na$_2$SO$_4$, filtered, and concentrated. The resulting crude product was dissolved in ether (100 ml) then washed with 50% saturated aqueous NaCl solution (4×100 ml), dried over Na$_2$SO$_4$, filtered and concentrated to a yellow oil (1.40 g, 75%). (TLC 20% EtOAc/hexanes R$_f$ 0.40); $^1$H NMR (400 MHz, CDCl$_3$) δ 7.69 (m, 2H), 7.56 (d, J=7.9 Hz, 1H), 7.45 (t, J=7.9 Hz, 1H), 7.36–7.20 (m, 5H), 3.58 (br s, 2H), 2.82 (s, 3H), 2.75 (d, J=10.3 Hz, 2H), 2.54 (br d, J=10.3 Hz, 2H), 2.43 (br s, 2H), 1.83 (d, J=8.1 Hz, 2H), 1.33 (m, 2H); APCI MS m/z 333.2 (M+1)$^+$.

3-Benzyl-8-(3-carboxamide-phenyl)-8-methoxy-3-aza-bicyclo[3.2.1]octane

3-Benzyl-8-(3-cyano-phenyl)-8-methoxy-3-aza-bicyclo[3.2.1]octane (1.40 g, 4.21 mmol) in DMSO (30 ml) was charged with potassium carbonate (87 mg, 0.632 mmol) then 30% aqueous hydrogen peroxide (2.15 ml, 21.1 mmol). The reaction mixture was allowed to stir at room temperature for 2 h. After a water quench (50 ml), the product was extracted with EtOAc (3×50 ml), washed with 50% saturated aqueous NaCl solution (5×50 ml), dried over $Na_2SO_4$, filtered and concentrated to a white solid (1.17 g, 80%). (TLC 50% EtOAc/hexanes $R_f$ 0.10); $^1$H NMR (400 MHz, $CDCl_3$) δ 7.89 (t, J=1.6 Hz, 1H), 7.69 (ddd, J=7.9, 2.4, 1.6 Hz, 1H), 7.59 (d, J=7.9 Hz, 1H), 7.43–7.19 (m, 6H), 3.58 (br s, 2H), 2.82 (s, 3H), 2.77 (d, J=10.0 Hz, 2H), 2.55 (br d, J=10.0 Hz, 2H), 2.51 (br s, 2H), 1.81 (d, J=7.4 Hz, 2H), 1.37 (m, 2H); APCI MS m/z 351.2 (M+1)$^+$.

8-(3-Carboxamide-phenyl)-8-methoxy-3-aza-bicyclo[3.2.1]octane

3-Benzyl-8-(3-carboxamide-phenyl)-8-methoxy-3-aza-bicyclo[3.2.1]octane (920 mg, 2.61 mmol) was dissolved in EtOAc (20 ml), charged with 2.5 N HCl/EtOAc (6 ml), then azeotroped with MeOH (2×50 ml) to yield the HCl salt. This salt was dissolved in MeOH (20 ml) in a 500 ml Parr bottle. To this was added 20% $Pd(OH)_2$/C (Pearlman's catalyst, 180 mg) and the mixture was shaken under 45 psi of $H_2$ for 4 h or until judged complete by TLC. The reaction was filtered through a Celite pad and concentrated to a yellow solid (1.0 g, >100%). $^1$H NMR (400 MHz, $CD_3OD$, HCl salt) δ 7.94 (s, 1H), 7.80 (d, J=7.1 Hz, 1H), 7.62 (d, J=6.6 Hz, 1H), 7.46 (m, 1H), 3.58 (br d, J=10.5 Hz, 2H), 3.08 (br d, J=10.5 Hz, 2H), 2.15 (br s, 5H), 1.74 (m, 2H), 1.63 (m, 2H); APCI MS m/z 261.2 (M+1)$^+$.

General Procedures

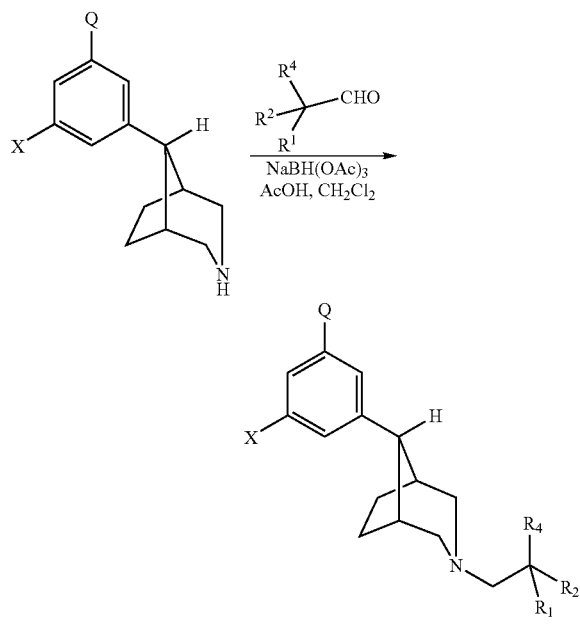

General Procedure for the Reductive Alkylation of Compounds of Formula I $R^a$=H A compound of the general formula I where $R^a$=H in dichloromethane or dichloroethane (0.2 M) at room temperature was treated with an appropriate aldehyde of formula (1.2 equiv), glacial acetic acid (catalytic ~2 drops) and sodium triacetoxyborohydride (1.5 equiv). The reaction mixture was stirred at room temperature for up to 24 h. The mixture was concentrated in vacuo and the resulting crude material was purified by flash chromatography to yield the desired tertiary amines in 40–95% yield.

The following compounds were made using the above procedure, starting with the appropriate starting amine and the appropriate corresponding aldehyde reagent.

Example 1

3-(3-Cyclopropylmethyl-3-aza-bicyclo[3.2.1]oct-8-yl)-phenol:

$^1$H NMR (400 MHz, $CD_3OD$, HCl salt) δ 7.10 (t, J=7.9 Hz, 1H), 6.74 (d, J=7.9 Hz, 1H), 6.68 (s, 1H), 6.61 (d, J=7.9 Hz, 1H), 3.62 (d, J=10.4 Hz, 2H), 3.30 (m, 2H), 3.10 (s, 1H), 3.02 (d, J=5.0 Hz, 2H), 2.80 (br s, 2H), 1.88 (d, 2H), 1.74 (m, 2H), 1.13 (m, 1H), 0.75 (m, 2H), 0.41 (m, 2H); GCMS m/z 257 (M)$^+$.

Example 2

N-(3-{3-[3-(1-Hydroxy-cyclohexyl)-propyl]-8-methoxy-3-aza-bicyclo[3.2.1]oct-8-yl}-phenyl)-methanesulfonamide $^1$H NMR (400 MHz, $CDCl_3$) δ 7.38 (s, 1H), 7.34 (t, J=7.9 Hz, 1H), 7.25 (d, J=7.9 Hz, 1H), 7.18 (d, J=7.9 Hz, 1H), 3.20 (m, 2H), 3.04 (d, J=9.9 Hz, 2H), 2.98 (s, 3H), 2.84 (m, 5H), 2.60 (br s, 2H), 2.02 (m, 2H), 1.83 (d, 2H), 1.61–1.22 (m, 14H); APCI MS m/z 451.3 (M+1)$^+$.

Example 3

3-{3-[3-(1-Hydroxy-cyclohexyl)-propyl]-8-methoxy-3-aza-bicyclo[3.2.1]oct-8-yl}-phenol $^1$H NMR (400 MHz, $CDCl_3$) δ 7.14 (t, J=7.9 Hz, 1H), 7.03 (s, 1H), 6.90 (d, J=7.9 Hz, 1H), 6.75 (d, J=7.9 Hz, 1H), 3.41 (m, 2H), 3.32 (d, J=9.2 Hz, 2H), 3.08 (t, J=7.5 Hz, 2H), 2.78 (s, 3H), 2.66 (br s, 2H), 2.03 (m, 2H), 1.95 (m, 2H), 1.58–1.18 (14H); APCI MS m/z 374.3 (M+1)$^+$.

Example 4

2-Methoxy-ethanesulfonic acid (3-{8-hydroxy-3-[3-(1-hydroxy-cyclohexyl)-propyl]-3-aza-bicyclo[3.2.1]oct-8-yl}-phenyl)-amide $^1$H NMR (400 MHz, $CDCl_3$) δ 7.38 (s, 1H), 7.30–7.23 (m, 3H), 3.76 (d, J=5.8 Hz, 2H), 3.33–3.22 (m, 7H), 2.86 (t, J=6.6 Hz, 2H), 2.52 (br s, 2H), 1.95 (m, 3H), 1.86 (d, J=8.6 Hz, 2H), 1.77 (d, J=6.5 Hz, 2H), 1.56–1.22 (m, 11H); APCI MS m/z 481.3 (M+1)$^+$.

Example 5

N-(3-{8-Hydroxy-3-[3-(1-hydroxy-cyclohexyl)-propyl]-3-aza-bicyclo[3.2.1]oct-8-yl}-phenyl)-methanesulfonamide $^1$H NMR (400 MHz, $CD_3OD$, citrate salt) δ 7.42 (s, 1H), 7.34 (m, 2H), 7.16 (d, J=7.4 Hz, 1H), 3.67 (d, J=12.0 Hz, 2H), 3.40 (br d, J=12.0 Hz, 2H), 3.12 (m, 2H), 2.92 (s, 3H), 2.81 (dd, J=12.4, 2.9 Hz, 2H), 2.79 (AB q, ΔAB=29.4, J=15.4, 4H), 2.66 (br s, 2H), 1.98–1.44 (m, 18H); APCI MS m/z 437.3 (M+1)+.

Example 6

3-{3-[3-(1-Hydroxy-cyclohexyl)-propyl]-8-methoxy-3-aza-bicyclo[3.2.1]oct-8-yl}-benzamide ¹H NMR (400 MHz, CD₃OD) δ 7.99 (s, 1H), 7.87 (d, J=7.9 Hz, 1H), 7.68 (d, J=7.9 Hz, 1H), 7.53 (t, J=7.9 Hz, 1H), 3.53 (d, J=11.5 Hz, 2H), 3.36 (d, J=11.5 Hz, 2H), 3.12 (br t, J=7.0 Hz, 2H), 2.91 (br s, 2H), 2.89 (s, 3H), 1.88–1.32 (m, 18H); APCI MS m/z 401.3 (M+1)+.

Example 7

3-[3-(1-Hydroxy-cyclohexyl)-propyl]-8-(3-hydroxy-phenyl)-3-aza-bicyclo[3.2.1]octan-8-ol ¹H NMR (400 MHz, CD₃OD) δ 7.18 (t, J=7.9 Hz, 1H), 6.96 (d, J=7.9 Hz, 1H), 6.93 (d, J=2.1 Hz, 1H), 6.72 (dd, J=7.9, 2.1 Hz, 1H), 3.66 (d, J=11.8 Hz, 2H), 3.37 (d, J=10.3 Hz, 2H), 3.11 (t, J=7.5 Hz, 2H), 2.65 (br s, 2H), 1.95–1.31 (m, 18H); APCI MS m/z 359.3 (M+1)+.

Example 8

3-(3-Cyclopropylmethyl-8-methoxy-3-aza-bicyclo[3.2.1]oct-8-yl)-benzamide

¹H NMR (400 MHz, CDCl₃) δ 7.90 (s, 1H), 7.70 (d, J=7.9 Hz, 1H), 7.59 (d, J=7.8 Hz, 1H), 7.41 (m, 1H), 6.25 (br s, NH) 5.99 (br s, NH), 2.80 (s, 3H), 2.74 (s, 4H), 2.52 (s, 2H), 2.32 (d, J=6.6 Hz, 2H), 1.79 (m, 2H), 1.37 (m, 2H), 0.87 (m, 1H), 0.47 (d, J=1.3 Hz, 2H), 0.45 (d, J=1.2 Hz, 2H); LCMS m/z 315.1 (M+1)+.

Furthermore, pharmaceutically acceptable salts of the compounds listed above can be prepared as follows. To a stirring solution of compounds of the general formula I (prepared as described above, 1.0 equiv) in a suitable solvent such as methyl ethyl ketone, dichloromethane/methanol (1:1) or methanol (0.1 M) at room temperature was added the appropriate acid, such as citric acid, p-toluenesulfonic acid, methanesulfonic acid or benzene sulfonic acid (1.0 equiv) in one portion. The resulting mixture was stirred at room temperature for up to 18 h, during which time a precipitate formed. Filtration of the solid and drying under reduced pressure afforded the desired salts.

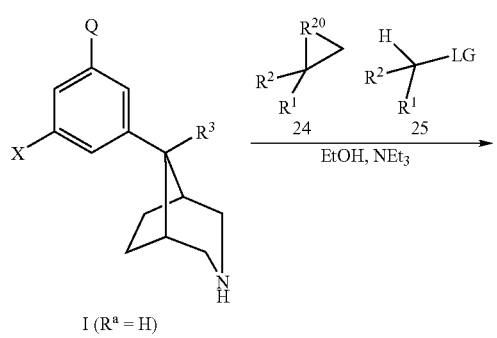

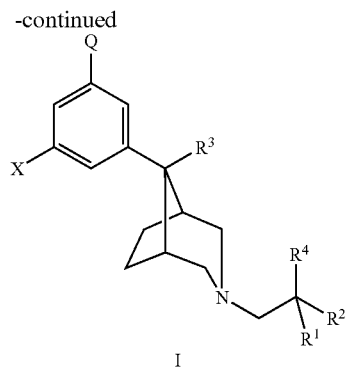

General Procedure for the Alkylation of Compounds of Formula I where R$^a$=H A compound of formula I where R$^a$=H in ethanol (0.1 M) at room temperature was treated with triethylamine (3.0 equiv) and the appropriate alkylation reagent (1.2 equiv). The resulting mixture was heated to 80° C. for 1–5 h and then cooled to room temperature. The mixture was concentrated in vacuo and the resulting crude material was purified by flash chromatography to yield the desired tertiary amines in 50–90% yield The following compounds were made using the above procedure, starting with the appropriate starting amine and the appropriate alkylation reagent.

Example 9

2-[8-(3-Hydroxy-phenyl)-3-aza-bicyclo[3.2.1]oct-3-ylmethyl]-indan-2-ol

¹H NMR (400 MHz, CDCl₃, HCl salt) δ 7.20 (m, 2H), 7.16 (m, 2H), 7.14 (m, 1H), 6.75 (t, J=7.9 Hz, 1H), 6.70 (d, J=7.9 Hz, 1H), 6.62 (d, J=7.9 Hz, 1H), 3.72 (d, J=10.0 Hz, 2H), 3.31–3.14 (9H), 2.85 (br s, 2H), 1.87 (d, 2H), 1.80 (m, 2H); APCI MS m/z 350.2 (M+1)+.

Example 10

N-{3-[3-(2-Hydroxy-indan-2-ylmethyl)-8-methoxy-3-aza-bicyclo[3.2.1]oct-8-yl]-phenyl}-methanesulfonamide ¹H NMR (400 MHz, CDCl₃) δ 7.36–7.13 (m, 8H), 3.06 (d, J=10.0 Hz, 2H), 2.98 (m, 7H), 2.86 (s, 3H), 2.73 (m, 4H), 2.51 (br s, 2H), 1.77 (d, 2H), 1.47 (m, 2H); APCI MS m/z 457.2 (M+1)+.

Example 11

N-{3-[3-(2-Hydroxy-indan-2-ylmethyl)-3-aza-bicyclo[3.2.1]oct-8-yl]-phenyl}-methanesulfonamide ¹H NMR (400 MHz, CDCl₃) δ 7.23–7.10 (m, 6H), 7.05 (d, J=7.5 Hz, 1H), 6.99 (d, J=7.9 Hz, 1H), 2.98 (s, 3H), 2.94 (s, 2H), 2.77 (s, 1H), 2.66 (s, 2H), 2.57(d, J=9.9 Hz, 2H), 2.51 (s, 2H), 1.70 (d, 2H), 1.62 (m, 2H); APCI MS m/z 427.1 (M+1)+.

Example 12

2-[8-(3-Hydroxy-phenyl)-8-methoxy-3-aza-bicyclo[3.2.1]oct-3-ylmethyl]-indan-2-ol ¹H NMR (400 MHz, CDCl₃) δ 7.23–7.11 (5H), 6.94 (d, J=7.4 Hz, 1H), 6.88 (s, 1H), 6.69 (d, J=7.8 Hz, 1H), 3.07 (d, J=9.5 Hz, 2H), 3.08 (br s, 4H), 2.86 (s, 3H), 2.74–2.70 (4H), 2.49 (s, 2H), 1.73 (d, J=7.4 Hz, 2H), 1.50 (m, 2H); APCI MS m/z 380.3 (M+1)$^+$.

Example 13

2-Methoxy-ethanesulfonic acid {3-[8-hydroxy-3-(2-hydroxy-indan-2-ylmethyl)-3-aza-bicyclo[3.2.1]oct-8-yl]-phenyl}-amide
$^1$H NMR (400 MHz, CDCl$_3$) δ 7.38 (s, 1H), 7.31 (m, 2H), 7.16 (m, 3H), 7.12 (m, 2H), 3.79 (t, J=5.8 Hz, 2H), 3.38 (s, 3H), 3.19 (m, 4H), 3.01 (AB m, 4H), 2.85 (m, 4H), 2.44 (br s, 2H), 1.79 (d, J=7.9 Hz, 2H), 1.45 (m, 2H); APCI MS m/z 487.3 (M+1)$^+$.

Example 14

N-{3-[8-hydroxy-3-(2-hydroxy-indan-2-ylmethyl)-3-aza-bicyclo[3.2.1]oct-8-yl]-phenyl}-methanesulfonamide
$^1$H NMR (400 MHz, CD$_3$OD, citrate salt) δ 7.43 (s, 1H), 7.34 (m, 2H), 7.20–7.11 (m, 5H), 3.70 (d, J=11.2 Hz, 2H), 3.39 (br d, J=9.5 Hz, 2H), 3.14 (AB q, ΔAB=48 Hz, J=16.2 Hz, 2H), 2.92 (s, 3H), 2.74 (AB q, ΔAB=31.0, J=15.3 Hz, 4H), 2.62 (br s, 2H), 1.86 (br d, J=8.7 Hz, 2H), 1.63 (m, 2H); LCMS m/z 443.1 (M+1)$^+$, m/z 331.1 (M+1)$^+$.

Example 15

2-Methoxy-ethanesulfonic acid {3-[3-(2-hydroxy-indan-2-ylmethyl)-8-methoxy-3-aza-bicyclo[3.2.1]oct-8-yl]-phenyl}-amide
$^1$H NMR (400 MHz, CDCl$_3$) δ 7.35–7.11 (m, 8H), 3.81 (t, J=5.4 Hz, 2H), 3.40 (s, 3H), 3.18 (t, J=5.4 Hz, 2H), 3.06 (d, J=10.4 Hz, 2H), 3.00 (s, 3H), 2.86 (s, 2H), 2.73 (s, 2H), 2.71 (dd, J=10.4, 2.7 Hz, 2H), 2.51 (br s, 2H), 1.76 (m, 2H), 1.47 (m, 2H); LCMS m/z 501.1 (M+1)$^+$.

Example 16

3-(2-Hydroxy-indan-2-ylmethyl)-8-(3-hydroxy-phenyl)-3-aza-bicyclo[3.2.1]octan-8-ol
$^1$H NMR (400 MHz, CD$_3$OD) δ 7.13 (m, 2H), 7.08 (m, 2H), 6.95 (d, J=7.9 Hz, 1H), 6.92 (s, 1H), 6.66 (dd, J=7.9, 2.7 Hz, 1H), 3.19 (m, 2H), 3.12 (AB d, J=16.2, 2H), 2.93 (AB d, J=16.2 Hz, 2H), 2.79 (m, 2H), 2.75 (br s, 2H), 2.41 (br s, 2H), 1.7 (d, J=7.4 Hz, 2H), 1.48 (m, 2H); APCI MS m/z 366.2 (M+1)$^+$.

Example 17

3-[3-(2-Hydroxy-indan-2-ylmethyl)-8-methoxy-3-aza-bicyclo[3.2.1]oct-8-yl]-benzamide
$^1$H NMR (400 MHz, CDCl$_3$) δ 7.92 (s, 1H), 7.69 (d, J=7.4 Hz, 1H), 7.60 (d, 7.9 Hz, 1H), 7.44 (t, J=7.9 Hz, 1H), 7.19–7.11 (m, 4H), 3.08 (t, J=5.0 Hz, 2H), 3.00 (s, 4H), 2.85 (s, 3H), 2.73 (br s, 4H), 2.58 (br s, 2H), 1.77 (d, J=7.5 Hz, 2H), 1.47 (br s, 2H); APCI MS m/z 407.4 (M+1)$^+$.

Example 18

2,2,2-Trifluoro-1-{3-[3-(2-hydroxy-indan-2-ylmethyl)-8-methoxy-3-aza-bicyclo[3.2.1]oct-8-yl]-phenyl}-ethanone
$^1$H NMR (400 MHz, CD$_3$OD, besylate salt) δ 7.90 (s, 1H), 7.81 (m, 2H), 7.62 (d, J=7.9 Hz, 1H), 7.49 (t, J=7.9 Hz, 1H), 7.42 (m, 4H), 7.23 (t, J=3.3 Hz, 2H), 7.19 (m, 2H), 3.81 (d, J=11.6 Hz, 2H), 3.60 (m, 4H), 3.29 (s, 15.3, 2H), 3.16 (d, J=16.2, 2H), 2.97 (s, 3H), 2.92 (s, 2H), 1.91 (m, 2H), 1.79 (m, 2H); LCMS m/z 475.2 (M+1)$^+$; APCI MS m/z 475.3 (M+1)$^+$.

Furthermore, pharmaceutically acceptable salts of the compounds listed above can be prepared as follows. To a stirring solution of compounds of the general formula I (prepared as described above, 1.0 equiv) in a suitable solvent such as methyl ethyl ketone, dichloromethane/methanol (1:1) or methanol (0.1 M) at room temperature was added the appropriate acid, such as citric acid, p-toluenesulfonic acid, methanesulfonic acid or benzene sulfonic acid (1.0 equiv) in one portion. The resulting mixture was stirred at room temperature for up to 18 h, during which time a precipitate formed. Filtration of the solid and drying under reduced pressure afforded the desired salts.

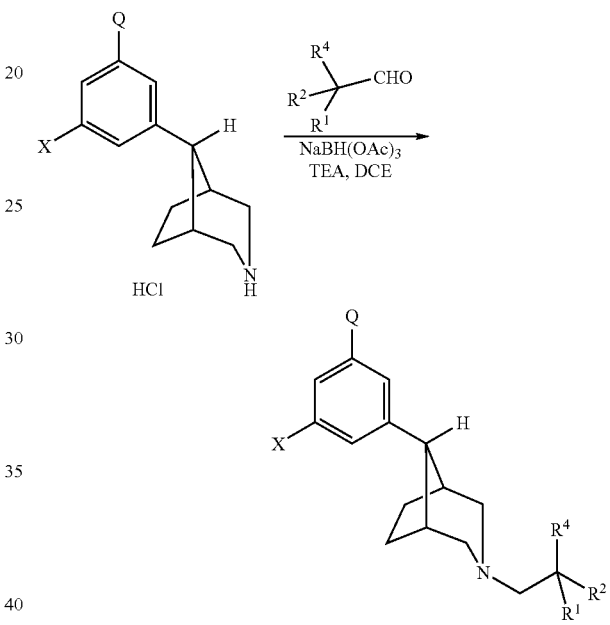

General Procedure for the Reductive Alkylation of Compounds of Salts of Formula R$^α$=H An appropriate aldehyde (2.0 equiv) in dichloroethane (0.1 M) at room temperature was treated with triethylamine (4.0 equiv) and an amine of formula I R$^α$=H (1 equiv) as the HCl salt. The reaction vessel was sealed and briefly shaken to mix these materials. The vessel was then opened and sodium triacetoxyborohydride (approximately 2.0 or more equiv) was introduced. The reaction vessel was again sealed then briefly vortexed. The reaction vessel was then shaken at room temperature for up to 24 h. The mixture was then quenched with the addition of 1 N NaOH (2.0 mL) and extracted with dichloromethane (3×2.45 mL). Each sequential extract was loaded onto SPE cartridges that contained 1 g of preconditioned SCX adsorbent. (The SCX adsorbent, "strong cation exchange modified silica", was preconditioned by pre-eluting with methanol (1×5 mL) then dichloromethane (2×5 mL).) After the extract solutions were passed through the adsorbent, the adsorbent was washed with methanol (5 mL). These filtrates were eventually discarded. Crude product was then eluted into separate tared collection vessels with 1N triethylamine in methanol (5 mL). The material was concentrated under a stream of nitrogen and weighed. The resulting crude material was purified by reverse phase HPLC to yield the desired tertiary amines in 1.2–70.2%.

The following compounds were made using the above procedure, starting with the appropriate starting amine of formula I ($R^a$=H) and the appropriate aldehyde reagent.

Example 19

3-(3-Ethyl-8-methoxy-3-aza-bicyclo[3.2.1]oct-8-yl)-benzamide LCMS m/z 289.1 (M+1)$^+$.

Example 20

3-[8-Methoxy-3-(3-methyl-butyl)-3-aza-bicyclo[3.2.1]oct-8-yl]-benzamide LCMS m/z 331.2 (M+1)$^+$.

Example 21

3-(8-Methoxy-3-pentyl-3-aza-bicyclo[3.2.1]oct-8-yl)-benzamide LCMS m/z 331.2 (M+1)$^+$.

Example 22

3-[8-Methoxy-3-(1H-pyrrol-2-ylmethyl)-3-aza-bicyclo[3.2.1]oct-8-yl]-benzamide LCMS m/z 340.1 (M+1)$^+$.

Example 23

3-(3-Hexyl-8-methoxy-3-aza-bicyclo[3.2.1]oct-8-yl)-benzamide LCMS m/z 345.2 (M+1)$^+$.

Example 24

3-[3-(2-Ethyl-butyl)-8-methoxy-3-aza-bicyclo[3.2.1]oct-8-yl]-benzamide MW LCMS m/z 345.2 (M+1)$^+$.

Example 25

3-[8-Methoxy-3-(1-methyl-1H-pyrrol-2-ylmethyl)-3-aza-bicyclo[3.2.1]oct-8-yl]-benzamide LCMS m/z 354.2 (M+1)$^+$.

Example 26

3-(8-Methoxy-3-thiophen-3-ylmethyl-3-aza-bicyclo[3.2.1]oct-8-yl)-benzamide LCMS m/z 357.6 (M+1)$^+$.

Example 27

3-(8-Methoxy-3-thiazol-2-ylmethyl-3-aza-bicyclo[3.2.1]oct-8-yl)-benzamide LCMS m/z 358 (M+1)$^+$.

Example 28

3-(8-Methoxy-3-octyl-3-aza-bicyclo[3.2.1]oct-8-yl)-benzamide LCMS m/z 373.2 (M+1)$^+$.

Example 29

3-[8-Methoxy-3-(3-phenyl-prop-2-ynyl)-3-aza-bicyclo[3.2.1]oct-8-yl]-benzamide LCMS m/z 375.2 (M+1)$^+$.

Example 30

3-[8-Methoxy-3-(3-phenyl-propyl)-3-aza-bicyclo[3.2.1]oct-8-yl]-benzamide LCMS m/z 379.2 (M+1)$^+$.

Example 31

3-[3-(1H-Indol-3-ylmethyl)-8-methoxy-3-aza-bicyclo[3.2.1]oct-8-yl]-benzamide LCMS m/z 390.1 (M+1)$^+$.

Example 32

3-(3-Benzofuran-2-ylmethyl-8-methoxy-3-aza-bicyclo[3.2.1]oct-8-yl)-benzamide LCMS m/z 391.1 (M+1)$^+$.

Example 33

3-(8-Methoxy-3-naphthalen-2-ylmethyl-3-aza-bicyclo[3.2.1]oct-8-yl)-benzamide LCMS m/z 401.2 (M+1)$^+$.

Example 34

3-(8-Methoxy-3-quinolin-3-ylmethyl-3-aza-bicyclo[3.2.1]oct-8-yl)-benzamide LCMS m/z 402.1 (M+1)$^+$.

Example 35

3-[3-(4-Chloro-2-fluoro-benzyl)-8-methoxy-3-aza-bicyclo[3.2.1]oct-8-yl]-benzamide LCMS m/z 403.1 (M+1)$^+$.

Example 36

3-[8-Methoxy-3-(1-methyl-1H-indol-3-ylmethyl)-3-aza-bicyclo[3.2.1]oct-8-yl]-benzamide LCMS m/z 404.2 (M+1)$^+$.

Example 37

3-[8-Methoxy-3-(2-phenethyloxy-ethyl)-3-aza-bicyclo[3.2.1]oct-8-yl]-benzamide LCMS m/z 409.2 (M+1)$^+$.

Example 38

2-Methoxy-ethanesulfonic acid [3-(8-hydroxy-3-pentyl-3-aza-bicyclo[3.2.1]oct-8-yl)-phenyl]-amide LCMS m/z 411.3 (M+1)$^+$.

Example 39

2-Methoxy-ethanesulfonic acid {3-[8-hydroxy-3-(3-methyl-butyl)-3-aza-bicyclo[3.2.1]oct-8-yl]-phenyl}-amide LCMS m/z 411.3 (M+1)$^+$.

Example 40

3-[3-(4-Hydroxy-naphthalen-1-ylmethyl)-8-methoxy-3-aza-bicyclo[3.2.1]oct-8-yl]-benzamide LCMS m/z 417.1 (M+1)$^+$.

Example 41

3-[8-Methoxy-3-(4-pyrrolidin-1-yl-benzyl)-3-aza-bicyclo[3.2.1]oct-8-yl]-benzamide LCMS m/z 420.2 (M+1)$^+$.

Example 42

3-[8-Methoxy-3-(3-methyl-benzo[b]thiophen-2-ylmethyl)-3-aza-bicyclo[3.2.1]oct-8-yl]-benzamide LCMS m/z 421.1 (M+1)$^+$.

Example 43

3-[3-(1-Hydroxy-3-phenyl-cyclobutylmethyl)-8-methoxy-3-aza-bicyclo[3.2.1]oct-8-yl]-benzamide LCMS m/z 421.1 (M+1)$^+$.

Example 44

2-Methoxy-ethanesulfonic acid [3-(3-hexyl-8-hydroxy-3-aza-bicyclo[3.2.1]oct-8-yl)-phenyl]-amide LCMS m/z 425.2 (M+1)$^+$.

Example 45

3-(3-Biphenyl-4-ylmethyl-8-methoxy-3-aza-bicyclo[3.2.1]oct-8-yl)-benzamide LCMS m/z 427.1 (M+1)$^+$.

Example 46

2-Methoxy-ethanesulfonic acid [3-(8-hydroxy-3-pyridin-3-ylmethyl-3-aza-bicyclo[3.2.1]oct-8-yl)-phenyl]-amide LCMS m/z 432.1 (M+1)$^+$.

Example 47

3-[8-Methoxy-3-(3-trifluoromethoxy-benzyl)-3-aza-bicyclo[3.2.1]oct-8-yl]-benzamide LCMS m/z 435.1 (M+1)$^+$.

Example 48

2-Methoxy-ethanesulfonic acid [3-(8-hydroxy-3-thiophen-3-ylmethyl-3-aza-bicyclo[3.2.1]oct-8-yl)-phenyl]-amide LCMS m/z 437.3 (M+1)$^+$.

Example 49

2-Methoxy-ethanesulfonic acid [3-(3-cyclohexylmethyl-8-hydroxy-3-aza-bicyclo[3.2.1]oct-8-yl)-phenyl]-amide LCMS m/z 437.16 (M+1)$^+$.

Example 50

3-[3-(9H-Fluoren-2-ylmethyl)-8-methoxy-3-aza-bicyclo[3.2.1]oct-8-yl]-benzamide LCMS m/z 439.1 (M+1)$^+$.

Example 51

3-[8-Methoxy-3-(3-phenoxy-benzyl)-3-aza-bicyclo[3.2.1]oct-8-yl]-benzamide LCMS m/z 443.1 (M+1)$^+$.

Example 52

3-[3-(4-Dimethylamino-naphthalen-1-ylmethyl)-8-methoxy-3-aza-bicyclo[3.2.1]oct-8-yl]-benzamide LCMS m/z 444.2 (M+1)$^+$.

Example 53

2-Methoxy-ethanesulfonic acid [3-(8-hydroxy-3-phenethyl-3-aza-bicyclo[3.2.1]oct-8-yl)-phenyl]-amide LCMS m/z 445.3 (M+1)$^+$.

Example 54

2-Methoxy-ethanesulfonic acid [3-(8-hydroxy-3-octyl-3-aza-bicyclo[3.2.1]oct-8-yl)-phenyl]-amide LCMS m/z 453.3 (M+1)$^+$.

Example 55

2-Methoxy-ethanesulfonic acid {3-[8-hydroxy-3-(3-phenyl-prop-2-ynyl)-3-aza-bicyclo[3.2.1]oct-8-yl]-phenyl}-amide LCMS m/z 455.3 (M+1)$^+$.

Example 56

2-Methoxy-ethanesulfonic acid {3-[8-hydroxy-3-(3-phenyl-propyl)-3-aza-bicyclo[3.2.1]oct-8-yl]-phenyl}-amide LCMS m/z 459.3 (M+1)$^+$.

Example 57

2-Methoxy-ethanesulfonic acid {3-[3-(4-chloro-benzyl)-8-hydroxy-3-aza-bicyclo[3.2.1]oct-8-yl]-phenyl}-amide LCMS m/z 465.1 (M+1)$^+$.

Example 58

2-Methoxy-ethanesulfonic acid {3-[8-hydroxy-3-(1H-indol-3-ylmethyl)-3-aza-bicyclo[3.2.1]oct-8-yl]-phenyl}-amide LCMS m/z 470.3 (M+1)$^+$.

Example 59

2-Methoxy-ethanesulfonic acid [3-(3-benzofuran-2-ylmethyl-8-hydroxy-3-aza-bicyclo[3.2.1]oct-8-yl)-phenyl]-amide LCMS m/z 471.3 (M+1)$^+$.

Example 60

2-Methoxy-ethanesulfonic acid[3-(8-hydroxy-3-naphthalen-2-ylmethyl-3-aza-bicyclo[3.2.1]oct-8-yl)-phenyl]-amide LCMS m/z 481.3 (M+1)$^+$.

Example 61

2-Methoxy-ethanesulfonic acid [3-(8-hydroxy-3-naphthalen-1-ylmethyl-3-aza-bicyclo[3.2.1]oct-8-yl)-phenyl]-amide LCMS m/z 481.3 (M+1)$^+$.

Example 62

2-Methoxy-ethanesulfonic acid [3-(8-hydroxy-3-quinolin-4-ylmethyl-3-aza-bicyclo[3.2.1]oct-8-yl)-phenyl]-amide LCMS m/z 482.3 (M+1)$^+$.

Example 63

2-Methoxy-ethanesulfonic acid [3-(8-hydroxy-3-quinolin-3-ylmethyl-3-aza-bicyclo[3.2.1]oct-8-yl)-phenyl]-amide LCMS m/z 482.3 (M+1)$^+$.

Example 64

2-Methoxy-ethanesulfonic acid {3-[8-hydroxy-3-(1-methyl-1H-indol-3-ylmethyl)-3-aza-bicyclo[3.2.1]oct-8-yl]-phenyl}-amide LCMS m/z 484.3 (M+1)$^+$.

Example 65

2-Methoxy-ethanesulfonic acid {3-[8-hydroxy-3-(2-phenethyloxy-ethyl)-3-aza-bicyclo[3.2.1]oct-8-yl]-phenyl}-amide LCMS m/z 489.3 (M+1)$^+$.

Example 66

2-Methoxy-ethanesulfonic acid {3-[8-hydroxy-3-(4-hydroxy-naphthalen-1-ylmethyl)-3-aza-bicyclo[3.2.1]oct-8-yl]-phenyl}-amide LCMS m/z 497.3 (M+1)+.

Example 67

2-Methoxy-ethanesulfonic acid {3-[8-hydroxy-3-(4-pyrrolidin-1-yl-benzyl)-3-aza-bicyclo[3.2.1]oct-8-yl]-phenyl}-amide LCMS m/z 500.38 (M+1)+.

Example 68

2-Methoxy-ethanesulfonic acid {3-[8-hydroxy-3-(3-methyl-benzo[b]thiophen-2-ylmethyl)-3-aza-bicyclo[3.2.1]oct-8-yl]-phenyl}-amide LCMS m/z 501.3 (M+1)+.

Example 69

2-Methoxy-ethanesulfonic acid [3-(3-biphenyl-4-ylmethyl-8-hydroxy-3-aza-bicyclo[3.2.1]oct-8-yl)-phenyl]-amide LCMS m/z 507.36 (M+1)+.

Example 70

2-Methoxy-ethanesulfonic acid {3-[3-(9H-fluoren-2-ylmethyl)-8-hydroxy-3-aza-bicyclo[3.2.1]oct-8-yl]-phenyl}-amide LCMS m/z 519.3 (M+1)+.

Example 71

2-Methoxy-ethanesulfonic acid {3-[8-hydroxy-3-(3-phenoxy-benzyl)-3-aza-bicyclo[3.2.1]oct-8-yl]-phenyl}-amide LCMS m/z 523.3 (M+1)+.

Example 72

2-Methoxy-ethanesulfonic acid {3-[3-(4-dimethylamino-naphthalen-1-ylmethyl)-8-hydroxy-3-aza-bicyclo[3.2.1]oct-8-yl]-phenyl}-amide LCMS m/z 524.34 (M+1)+.

Furthermore, pharmaceutically acceptable salts of the compounds listed above can be prepared as follows. To a stirring solution of compounds of the general formula I (prepared as described above, 1.0 equiv) in a suitable solvent such as methyl ethyl ketone, dichloromethane/methanol (1:1) or methanol (0.1 M) at room temperature was added the appropriate acid, such as citric acid, p-toluenesulfonic acid, methanesulfonic acid or benzene sulfonic acid (1.0 equiv) in one portion. The resulting mixture was stirred at room temperature for up to 18 h, during which time a precipitate formed. Filtration of the solid and drying under reduced pressure afforded the desired salts.

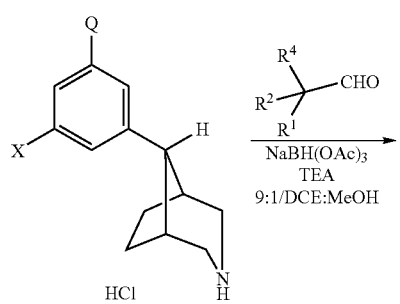

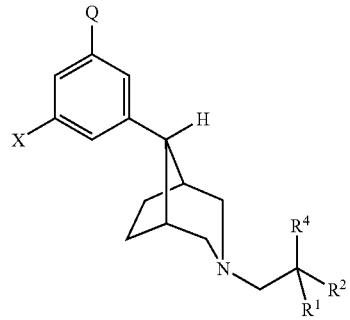

General Procedure for the Reductive Alkylation of Salts of Compounds of Formula $R^a$=H An appropriate aldehyde (2.0 equiv) at room temperature was treated with a slurry of an amine of formula I $R^a$=H (1 equiv) as the HCl salt in 9:1 dichloroethane:methanol. The reaction vessel was sealed and briefly shaken to mix these materials. The vessel was then opened and sodium triacetoxyborohydride (approximately 5.0 or more equiv) was introduced. The reaction vessel was shaken at room temperature for up to 24 h. The mixtures were then quenched by the addition of water (0.75 mL) and extracted with dichloromethane (3×2.45 mL). Each sequential extract was loaded onto SPE cartridges that contained 1 g of preconditioned SCX absorbant. (The SCX absorbant, "strong cation exchange modified silica", was preconditioned by pre-eluting with MeOH (1×5 mL) then dichloromethane (2×5 mL).) After the extract solutions were passed through the adsorbent, the adsorbent was washed with dichloromethane (5 mL) then methanol (5 mL). These filtrates were eventually discarded. Crude product was then eluted into separate tared collection vessels with 1N triethylamine in methanol (5 mL). The material was concentrated under a stream of nitrogen and weighed. The resulting crude material was purified by reverse phase HPLC to yield the desired tertiary amines in 1.8–48.3%.

The following compounds were made using the above procedure, starting with the appropriate starting amine of formula I $R^a$=H and the appropriate aldehyde reagent.

Example 73

N-[3-(3-Cyclopropylmethyl-8-methoxy-3-aza-bicyclo[3.2.1]oct-8-yl)-phenyl]-methanesulfonamide LCMS m/z 365.1 (M+1)+.

Example 74

3-(8-Methoxy-3-phenethyl-3-aza-bicyclo[3.2.1]oct-8-yl)-benzamide LCMS m/z 365.2 (M+1)+.

Example 75

N-[3-(3-Isobutyl-8-methoxy-3-aza-bicyclo[3.2.1]oct-8-yl)-phenyl]-methanesulfonamide LCMS m/z 367.2 (M+1)+.

Example 76

N-{3-[8-Methoxy-3-(3-methyl-butyl)-3-aza-bicyclo[3.2.1]oct-8-yl]-phenyl}-methanesulfonamide LCMS m/z 381.2 (M+1)+.

Example 77

N-[3-(8-Methoxy-3-pentyl-3-aza-bicyclo[3.2.1]oct-8-yl)-phenyl]-methanesulfonamide LCMS m/z 381.2 (M+1)$^+$.

Example 78

N-{3-[3-(2-Ethyl-butyl)-8-methoxy-3-aza-bicyclo[3.2.1]oct-8-yl]-phenyl}-methanesulfonamide LCMS m/z 395.2 (M+1)$^+$.

Example 79

N-[3-(3-Hexyl-8-methoxy-3-aza-bicyclo[3.2.1]oct-8-yl)-phenyl]-methanesulfonamide LCMS m/z 395.2 (M+1)$^+$.

Example 80

N-[3-(8-Methoxy-3-pyridin-3-ylmethyl-3-aza-bicyclo[3.2.1]oct-8-yl)-phenyl]-methanesulfonamide LCMS m/z 402.2 (M+1)$^+$.

Example 81

N-[3-(8-Methoxy-3-thiazol-2-ylmethyl-3-aza-bicyclo[3.2.1]oct-8-yl)-phenyl]-methanesulfonamide LCMS m/z 408.1 (M+1)$^+$.

Example 82

N-[3-(3-Heptyl-8-methoxy-3-aza-bicyclo[3.2.1]oct-8-yl)-phenyl]-methanesulfonamide LCMS m/z 409.2 (M+1)$^+$.

Example 83

N-[3-(8-Methoxy-3-phenethyl-3-aza-bicyclo[3.2.1]oct-8-yl)-phenyl]-methanesulfonamide LCMS m/z 415.1 (M+1)$^+$.

Example 84

N-{3-[3-(4-Fluoro-benzyl)-8-methoxy-3-aza-bicyclo[3.2.1]oct-8-yl]-phenyl}-methanesulfonamide LCMS m/z 419.1 (M+1)$^+$.

Example 85

N-{3-[3-(2-Ethyl-hexyl)-8-methoxy-3-aza-bicyclo[3.2.1]oct-8-yl]-phenyl}-methanesulfonamide LCMS m/z 423.2 (M+1)$^+$.

Example 86

N-[3-(8-Methoxy-3-octyl-3-aza-bicyclo[3.2.1]oct-8-yl)-phenyl]-methanesulfonamide LCMS m/z 423.2 (M+1)$^+$.

Example 87

N-{3-[8-Methoxy-3-(4-methoxy-benzyl)-3-aza-bicyclo[3.2.1]oct-8-yl]-phenyl}-methanesulfonamide LCMS m/z 431.1 (M+1)$^+$.

Example 88

N-{3-[3-(4-Chloro-benzyl)-8-methoxy-3-aza-bicyclo[3.2.1]oct-8-yl]-phenyl}-methanesulfonamide LCMS m/z 435 (M+1)$^+$.

Example 89

N-{3-[3-(1H-indol-3-ylmethyl)-8-methoxy-3-aza-bicyclo[3.2.1]oct-8-yl]-phenyl}-methanesulfonamide LCMS m/z 440.1 (M+1)$^+$.

Example 90

N-[3-(3-Benzofuran-2-ylmethyl-8-methoxy-3-aza-bicyclo[3.2.1]oct-8-yl)-phenyl]-methanesulfonamide LCMS m/z 441.1 (M+1)$^+$.

Example 91

N-[3-(8-Methoxy-3-naphthalen-1-ylmethyl-3-aza-bicyclo[3.2.1]oct-8-yl)-phenyl]-methanesulfonamide LCMS m/z 451.1 (M+1)$^+$.

Example 92

N-[3-(8-Methoxy-3-naphthalen-2-ylmethyl-3-aza-bicyclo[3.2.1]oct-8-yl)-phenyl]-methanesulfonamide LCMS m/z 451.1 (M+1)$^+$.

Example 93

N-[3-(8-Methoxy-3-quinolin-4-ylmethyl-3-aza-bicyclo[3.2.1]oct-8-yl)-phenyl]-methanesulfonamide LCMS m/z 452.1 (M+1)$^+$.

Example 94

N-[3-(8-Methoxy-3-quinolin-3-ylmethyl-3-aza-bicyclo[3.2.1] oct-8-yl)-phenyl]-methanesulfonamide LCMS m/z 452.1 (M+1)$^+$.

Example 95

N-{3-[3-(4-Chloro-2-fluoro-benzyl)-8-methoxy-3-aza-bicyclo[3.2.1]oct-8-yl]-phenyl}-methanesulfonamide LCMS m/z 453.1 (M+1)$^+$.

Example 96

N-{3-[8-Methoxy-3-(1-methyl-1H-indol-3-ylmethyl)-3-aza-bicyclo[3.2.1]oct-8-yl]-phenyl}-methanesulfonamide LCMS m/z 454.1 (M+1)$^+$.

Example 97

N-{3-[3-(4-Hydroxy-naphthalen-1-ylmethyl)-8-methoxy-3-aza-bicyclo[3.2.1]oct-8-yl]-phenyl}-methanesulfonamide LCMS m/z 467.1 (M+1)$^+$.

Example 98

N-{3-[8-Methoxy-3-(4-pyrrolidin-1-yl-benzyl)-3-aza-bicyclo[3.2.1]oct-8-yl]-phenyl}-methanesulfonamide LCMS m/z 469.2 (M+1)$^+$.

Example 99

N-{3-[8-Methoxy-3-(3-methyl-benzo[b]thiophen-2-ylmethyl)-3-aza-bicyclo[3.2.1]oct-8 -yl]-phenyl}-methanesulfonamide LCMS m/z 471.1 (M+1)$^+$.

Example 100

N-[3-(3-Biphenyl-4-ylmethyl-8-methoxy-3-aza-bicyclo[3.2.1]oct-8-yl)-phenyl]-methanesulfonamide LCMS m/z 477.1 (M+1)+.

Example 101

N-{3-[8-Methoxy-3-(3-trifluoromethoxy-benzyl)-3-aza-bicyclo[3.2.1]oct-8-yl]-phenyl}-methanesulfonamide LCMS m/z 485 (M+1)+.

Example 102

N-{3-[3-(9H-Fluoren-2-ylmethyl)-8-methoxy-3-aza-bicyclo[3.2.1]oct-8-yl]-phenyl}-methanesulfonamide LCMS m/z 489.1 (M+1)+.

Example 103

N-{3-[8-Methoxy-3-(3-phenoxy-benzyl)-3-aza-bicyclo[3.2.1]oct-8-yl]-phenyl}-methanesulfonamide LCMS m/z 493.1 (M+1)+.

Example 104

N-{3-[3-(4-Dimethylamino-naphthalen-1-ylmethyl)-8-methoxy-3-aza-bicyclo[3.2.1]oct-8-yl]-phenyl}-methanesulfonamide LCMS m/z 494.1 (M+1)+.

Furthermore, pharmaceutically acceptable salts of the compounds of the invention can be prepared as follows. To a stirring solution of compounds of the general formula I (prepared as described above, 1.0 equiv) in a suitable solvent such as methyl ethyl ketone, dichloromethane/methanol (1:1) or methanol (0.1 M) at room temperature was added the appropriate acid, such as citric acid, p-toluenesulfonic acid, methanesulfonic acid or benzene sulfonic acid (1.0 equiv) in one portion. The resulting mixture was stirred at room temperature for up to 18 h, during which time a precipitate formed. Filtration of the solid and drying under reduced pressure afforded the desired salts.

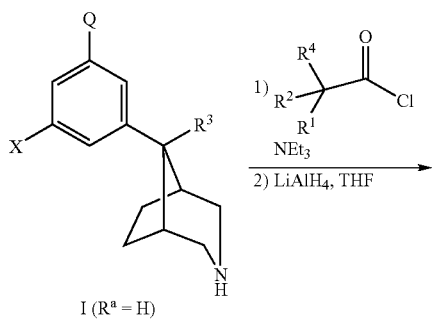

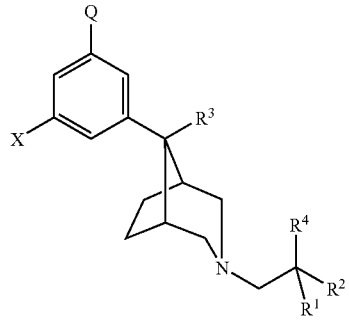

Alternative General Procedure for the Preparation of Compounds of formula I.

To a stirring solution of 1.0 equiv of a compound of formula I where $R^a$=H in anhydrous THF (0.1 M) at room temperature, was added $Et_3N$ (5.0 equiv) or pyridine (5.0 equiv) and an appropriately substituted acid chloride (2.0 equiv). After stirring up to 24 h, the reaction was quenched by the addition of water and diluted with methylene chloride. The layers were separated, the aqueous layer was extracted with methylene chloride and the combined organic layers were dried over anhydrous $Na_2SO_4$ and concentrated. The resulting crude material was purified through flash chromatography, then carried onto the next step.

To a stirring solution of 1.0 equiv of the amide prepared above in THF (0.2M) at room temperature was added lithium aluminum hydride (4.0 equiv). The resulting mixture was stirred at room temperature until judged complete by TLC. The reaction was cooled to 0° C. then carefully quenched by the slow addition of water (1.0 equiv by mass relative to LAH), 10% NaOH (1.0 equiv by mass relative to LAH) then water (3.0 equiv by mass relative to LAH). The resulting slurry was stirred at room temperature for up to 16 hours. The slurry was filtered and washed with THF. The resulting solution was concentrated to yield crude material that was purified by flash chromatography to afford the desired tertiary amines of formula I.

The following compound was made using the above procedure, starting with the appropriate starting amine of formula I and the appropriate acid chloride reagent.

Example 105

3-(3-Cyclohexyl-propyl)-8-(3-hydroxy-phenyl)-3-aza-bicyclo[3.2.1]octan-8-ol $^1$H NMR (400 MHz, CDCl$_3$) δ 7.09 (m, 1H), 6.75 (d, J=7.4 Hz, 1H), 6.69 (s, 1H), 6.61 (d, J=7.9 Hz, 1H), 2.90 (d, J=8.3 Hz, 2H), 2.65 (s, 1H), 2.44 (s, 2H), 2.30 (d, J=6.6 Hz, 2H), 2.20 (d, J=9.9 Hz, 2H), 1.68–1.11 (m, 19H); GCMS m/z 327 (M)+.

Furthermore, pharmaceutically acceptable salts of the compound listed above can be prepared as follows. To a stirring solution of compounds of the general formula I (prepared as described above, 1.0 equiv.) in a suitable solvent such as methyl ethyl ketone, methylene chloride/methanol (1:1) or methanol (0.1 M) at room temperature was added the appropriate acid, such as citric acid, p-toluenesulfonic acid, methansulfonic acid or benzene sulfonic acid (1.0 equiv) in one portion. The resulting mixture was stirred at room temperature for up to 18 h, during which time a precipitate formed. Filtration of the solid and drying under reduced pressure afforded the desired salts.

We claim:

1. A compound according to formula I, or a pharmaceutically acceptable salt thereof:

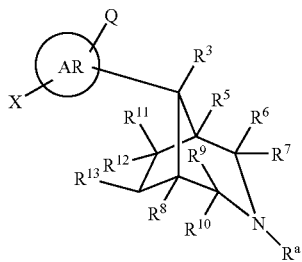

I wherein $R^a$ is a

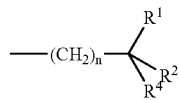

group;

is a phenyl group;

X is H, halogen, —OH, —CN, —C≡C—$R^{3a}$, a —$C_1$–$C_4$ alkyl group optionally substituted with from one to three halogen atoms, or a —O($C_1$–$C_4$ alkyl) group optionally substituted with from one to three halogen atoms;

Q is substituted at a meta position on said phenyl group and is selected from the group consisting of —C(=O)NH$_2$, —OH and —NHSO$_2R^{15}$;

$R^{3a}$ is H or $C_1$–$C_6$ alkyl which may be optionally substituted with one or more halogen groups;

$R^1$ and $R^2$ are independently H, a $C_1$–$C_6$ alkyl, —(CH$_2$)$_j$-aryl, —(CH$_2$)$_j$-heteroaryl, wherein said alkyl, —(CH$_2$)$_j$aryl or —(CH$_2$)$_j$-heteroaryl group is optionally substituted with one or more $R^{16}$ groups, or with the carbon to which $R^1$ and $R^2$ are attached, $R^1$ and $R^2$ form a $C_3$–$C_7$ carbocyclic or 4- to 7-membered heterocyclic group, wherein said heterocyclic group comprises from one to three heteroatoms selected from the group consisting of O, S and N and said carbocyclic or heterocyclic group optionally contains a —C(=O) group or optionally contains one or more double bonds and is optionally fused to or substituted with a $C_6$–$C_{14}$ aryl or a 5- to 14-membered heteroaryl group, wherein said $C_3$–$C_7$ carbocyclic or 4- to 7-membered heterocyclic group formed by $R^1$ and $R^2$ may optionally be substituted with from one to three $R^{16}$ groups, and said optionally fused or substituted aryl or heteroaryl group may each optionally independently be substituted with from one to six $R^{16}$ groups;

each $R^{16}$ is independently selected from $R^{17}$, H, halogen, —OR$^{17}$, —NO$_2$, —CN, —C$_1$–C$_6$ alkyl, —C$_3$–C$_6$ cycloalkyl, —C(R$^4$)R$^{16a}$R$^{16b}$, aryl optionally substituted with from 1 to 3 R$^4$ groups, —(CH$_2$)$_v$NR$^{17}$R$^{18}$, —NR$^{17}$C(=O)R$^{18}$, —C(=O)NR$^{17}$R$^{18}$, —OC(=O)R$^{17}$, —C(=O)OR$^{17}$, —C(=O)R$^{17}$, —NR$^{17}$C(=O)OR$^{18}$, —NR$^{17}$C(=O)N R$^{18}$R$^{19}$, —NR$^{17}$S(=O)$_2$R$^{18}$, —NR$^{17}$S(=O)$_2$NR$^{18}$R$^{19}$, and —S(=O)$_2$R$^{17}$;

$R^3$ is H, F, Cl, —OH, —C$_1$–C$_4$ alkyl, —C≡N, —NR$^{17}$C(=O)R$^{18}$, —C(=O)NR$^{17}$R$^{18}$, —O(C$_1$–C$_4$)alkyl, —(CH$_2$)$_n$OH, —(CH$_2$)$_n$—C≡N, —(CH$_2$)$_n$—NR$^{17}$C(=O)R$^{18}$, —(CH$_2$)$_n$—C(=O)NR$^{17}$R$^{18}$, —(CH$_2$)$_n$—O(C$_1$–C$_4$)alkyl, or —(CH$_2$)$_n$—NR$^{16a}$R$^{16b}$;

$R^4$ is absent or is H, —C$_1$–C$_4$ alkyl, which optionally contains one or two unsaturated bonds, —OH, —O(C$_1$–C$_4$)alkyl, —(C$_1$–C$_4$)alkylOH, —(CH$_2$)$_n$—NR$^{16a}$R$^{16b}$, —(CH$_2$)$_n$—NHC(=O)(C$_1$–C$_4$ alkyl), —(CH$_2$)$_n$—NO$_2$, —(CH$_2$)$_n$—C≡N, —(CH$_2$)$_n$—C(=O)NH$_2$, —(CH$_2$)$_n$—C(=O)NR$^{16a}$R$^{16b}$;

$R^5$ and $R^8$ are independently selected from H, Cl, F, —OH, C$_1$–C$_4$ alkyl, —O(C$_1$–C$_4$)alkyl, —C(=O)R$^{20}$, —(C$_1$–C$_4$ alkyl)-OR$^{20}$, —C(=O)OR$^{20}$, —OC(=O)R$^{20}$, —S(O)$_m$R$^{20}$ and —NHSO$_2$(C$_1$–C$_4$)alkyl;

$R^6$, $R^7$, $R^9$, $R^{10}$, $R^{11}$, $R^{12}$, $R^{13}$ and $R^{14}$ are each independently selected from H, F, Cl, —OH, —(C$_1$–C$_4$)alkyl and —O(C$_1$–C$_4$)alkyl;

$R^{15}$, $R^{17}$, $R^{18}$ and $R^{19}$ are independently H, —C$_1$–C$_4$ alkyl, —(C$_2$–C$_4$ alkyl)-O—(C$_1$–C$_4$ alkyl), —(CH$_2$)$_v$—NR$^{21}$R$^{22}$, or a 4- to 7-membered heterocyclic group optionally substituted with a —C$_1$–C$_4$ alkyl;

each $R^{16a}$ and $R^{16b}$ is independently selected from H and C$_1$–C$_4$ alkyl; or, independently in each instance of —C(R$^4$)R$^{16a}$R$^{16b}$, R$^{16a}$ and R$^{16b}$ connect to form a C$_3$–C$_7$ carbocyclic ring;

$R^{20}$ is a C$_1$–C$_4$ alkyl group, a C$_3$–C$_7$ carbocyclic or a 4- to 7-membered heterocyclic group comprising from one to three heteroatoms selected from the group consisting of O, S and N, wherein said carbocyclic and heterocyclic groups are optionally independently substituted with from one to three R$^{16}$ groups, optionally independently contain one or more double bonds, and are optionally fused to a C$_8$–C$_{14}$ aryl or a C$_5$–C$_{14}$ heteroaryl group comprising from one to three heteroatoms selected from the group consisting of O, S and N, and wherein said optionally fused aryl or heteroaryl groups can each optionally independently be substituted with from one to six R$^{16}$ groups;

$R^{21}$ and $R^{22}$ are each independently H or C$_1$–C$_6$ alkyl; or, independently in each instance of —NR$^{21}$R$^{22}$, R$^{21}$ and R$^{22}$ connect to form a 4- to 7-membered heterocyclic ring comprising from one to three hetero atoms selected from O, S, and N;

j is in each instance independently an integer from 0 to 5;

m is in each instance independently an integer from 0 to 2;

n is in each instance independently an integer from 0 to 5;
v is in each instance independently an integer from 0 to 5;
or a pharmaceutically acceptable salt thereof;
with the provisos that
a) when $R^a$ is

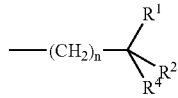

and n is 0, and when the carbon to which $R^1$, $R^2$ and $R^4$ are bound is $sp^3$ hybridized (i.e., "saturated"), then none of $R^1$, $R^2$ and $R^4$ can be a heteroatom or contain a heteroatom which is directly linked to the carbon of said

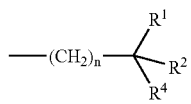

group;
b) $R^{15}$ cannot be H when part of a —NHS(=O)$_2R^{15}$ group, $R^{17}$ cannot be H when part of a —S(=O)$_2R^{17}$ group and $R^{18}$ cannot be H when part of a —NR$^{17}$S(=O)$_2R^{18}$ group;
c) when $R^3$ is OCH$_3$ or OH,

cannot be 3-hydroxyphenyl or 3-methoxyphenyl; and
d) when —(CH$_2$)$_v$— is connected to N, O, or S, then v cannot be 1.

2. A compound according to claim 1 wherein X is H, F or C≡N.

3. A compound according to claim 1, wherein $R^3$ is H, OH, Cl, methyl, ethyl, isopropyl, OMe, OEt, O-iPr, O-allyl or O-n-Pr.

4. A compound according to claim 1, wherein $R^1$ and $R^2$ taken together with the carbon to which they are attached form a cyclobutane, cyclopentane, cyclohexane, indane-2-yl or 1,2,3,4-tetrahydronaphth-2-yl which may be unsubstituted or substituted with $R^{16}$ groups; and wherein $R^4$ is H, OH, —NH(=O)—CH$_3$, —C(=O)NH$_2$, —CH$_2$OH or —OCH$_3$.

5. A compound according to claim 1, wherein n is 1, 2 or 3.

6. A compound according to claim 1, wherein $R^5$, $R^6$, $R^7$, $R^8$, $R^9$, $R^{10}$, $R^{11}$, $R^{12}$, $R^{13}$ and $R^{14}$ are each H.

7. A compound according to claim 1 selected from the group consisting of
3-(3-Cyclopropylmethyl-3-aza-bicyclo[3.2.1]oct-8-yl)-phenol;
3-(3-Ethyl-8-methoxy-3-aza-bicyclo[3.2.1]oct-8-yl)-benzamide;
3-(3-Cyclopropylmethyl-8-methoxy-3-aza-bicyclo[3.2.1]oct-8-yl)-benzamide;
3-[3-(3-Cyclohexyl-propyl)-3-aza-bicyclo[3.2.1]oct-8-yl]-phenol;
3-[8-Methoxy-3-(3-methyl-butyl)-3-aza-bicyclo[3.2.1]oct-8-yl]-benzamide;
3-(8-Methoxy-3-pentyl-3-aza-bicyclo[3.2.1]oct-8-yl)-benzamide;
3-[8-Methoxy-3-(1H-pyrrol-2-ylmethyl)-3-aza-bicyclo]3.2.1]oct-8-yl]-benzamide;
3-(3-Hexyl-8-methoxy-3-aza-bicyclo[3.2.1]oct-8-yl)-benzamide;
3-[3-(2-Ethyl-butyl)-8-methoxy-3-aza-bicyclo[3.2.1]oct-8-yl]-benzamide;
2-[8-(3-Hydroxy-phenyl)-3-aza-bicyclo[3.2.1]oct-3-ylmethyl]-indan-2-ol;
3-[8-Methoxy-3-(1-methyl-1H-pyrrol-2-ylmethyl)-3-aza-bicyclo[3.2.1]oct-8-yl]-benzamide;
3-(8-Methoxy-3-thiophen-3-ylmethyl-3-aza-bicyclo[3.2.1]oct-8-yl)-benzamide;
3-(8-Methoxy-3-thiazol-2-ylmethyl-3-aza-bicyclo[3.2.1]oct-8-yl)-benzamide;
3-[3-(1-Hydroxy-cyclohexyl)-propyl]-8-(3-hydroxy-phenyl)-3-aza-bicyclo[3.2.1]octan-8-ol;
N-[3-(3-Cyclopropylmethyl-8-methoxy-3-aza-bicyclo[3.2.1]oct-8-yl)-phenyl]-methanesulfonamide;
3-(8-Methoxy-3-phenethyl-3-aza-bicyclo[3.2.1]oct-8-yl)-benzamide;
3-(2-Hydroxy-indan-2-ylmethyl)-8-(3-hydroxy-phenyl)-3-aza-bicyclo[3.2.1]octan-8-ol;
N-[3-(3-Isobutyl-8-methoxy-3-aza-bicyclo[3.2.1]oct-8-yl)-phenyl]-methanesulfonamide;
3-(8-Methoxy-3-octyl-3-aza-bicyclo[3.2.1]oct-8-yl)-benzamide;
3-{3-[3-(1-Hydroxy-cyclohexyl)-propyl]-8-methoxy-3-aza-bicyclo[3.2.1]oct-8-yl}-phenol;
3-[8-Methoxy-3-(3-phenyl-prop-2-ynyl)-3-aza-bicyclo[3.2.1]oct-8-yl]-benzamide;
3-[8-Methoxy-3-(3-phenyl-propyl)-3-aza-bicyclo[3.2.1]oct-8-yl]-benzamide;
2-[8-(3-Hydroxy-phenyl)-8-methoxy-3-aza-bicyclo[3.2.1]oct-3-ylmethyl]-indan-2-ol;
N-{3-[8-Methoxy-3-(3-methyl-butyl)-3-aza-bicyclo[3.2.1]oct-8-yl]-phenyl}-methanesulfonamide;
N-[3-(8-Methoxy-3-pentyl-3-aza-bicyclo[3.2.1]oct-8-yl)-phenyl]-methanesulfonamide;
3-[3-(1H-Indol-3-ylmethyl)-8-methoxy-3-aza-bioyclo[3.2.1]oct-8-yl]-benzamide;
3-(3-Benzofuran-2-ylmethyl-8-methoxy-3-aza-bicyclo[3.2.1]oct-8-yl)-benzamide;
3-[3-(2-Hydroxy-1,2,3,4-tetrahydro-naphthalen-2-ylmethyl)-3-aza-bicyclo[3.2.1]oct-8-yl]-benzamide;
N-{3-[3-(2-Ethyl-butyl)-8-methoxy-3-aza-bicyclo[3.2.1]oct-8-yl]-phenyl}-methanesulfonamide;
N-[3-(3-Hexyl-8-methoxy-3-aza-bicyclo[3.2.1]oct-8-yl)-phenyl-methanesulfonamide;
3-(8-Methoxy-3-naphthalen-2-ylmethyl-3-aza-bicyclo[3.2.1]oct-8-yl)-benzamide;
3-{3-[3-(1-Hydroxy-cyclohexyl)-propyl]-8-methoxy-3-aza-bicyclo[3.2.1]oct-8-yl}-benzamide;
3-(8-Methoxy-3-quinolin-3-ylmethyl-3-aza-bicyclo[3.2.1]oct-8-yl)-benzamide;
N-[3-(8-Methoxy-3-pyridin-3-ylmethyl-3-aza-bicyclo[3.2.1]oct-8-yl)-phenyl]-methanesulfonamide;
3-[3-(4-Chloro-2-fluoro-benzyl)-8-methoxy-3-aza-bicyclo[3.2.1]oct-8-yl]-benzamide;
3-[8-Methoxy-3-(1-methyl-1H-indol-3-ylmethyl)-3-aza-bicyclo[3.2.1]oct-8-yl]-benzamide;
3-[3-(2-Hydroxy-1,2,3,4-tetrahydro-naphthalen-2-ylmethyl)-8-hydroxy-3-aza-bicyclo[3.2.1]oct-8-yl]-benzamide;

3-[3-(2-Hydroxy-indan-2-ylmethyl)-8-methoxy-3-aza-bicyclo[3.2.1]oct-8-yl]-benzamide;
N-[3-(8-Methoxy-3-thiazol-2-ylmethyl-3-aza-bicyclo[3.2.1]oct-8-yl)-phenyl]-methanesulfonamide;
3-[8-Methoxy-3-(2-phenethyloxy-ethyl)-3-aza-bicyclo[3.2.1]oct-8-yl]-benzamide;
N-[3-(3-Heptyl-8-methoxy-3-aza-bicyclo[3.2.1]oct-8-yl)-phenyl]-methanesulfonamide;
2-Methoxy-ethanesulfonic acid [3-(8-hydroxy-3-pentyl-3-aza-bicyclo[3.2.1]oct-8-yl)-phenyl]-amide;
2-Methoxy-ethanesulfonic acid {3-[8-hydroxy-3-(3-methyl-butyl)-3-aza-bicyclo[3.2.1]oct-8-yl]-phenyl}-amide;
N-[3-(8-Methoxy-3-phenethyl-3-aza-bicyolo[3.2.1]oct-8-yl)-phenyl]-methanesulfonamide;
3-[3-(4-Hydroxy-naphthalen-1-ylmethyl)-8-methoxy-3-aza-bicyclo[3.2.1]oct-8-yl]-benzamide;
N-{3-[3-(4-Fluoro-benzyl)-8-methoxy-3-aza-bicyclo[3.2.1]oct-8-yl]-phenyl}-methanesulfonamide;
3-[8-Methoxy-3-(4-pyrrolidin-1-yl-benzyl)-3-aza-bicyclo[3.2.1]oct-8-yl]-benzamide;
3-[8-Methoxy-3-(3-methyl-benzol-benzo[b]thiophen-2-ylmethyl)-3-aza-bicyclo[3.2.1]oct-8-yl]-benzamide;
3-[3-(2-Hydroxy-1,2,3,4-tetrahydro-naphthalen-2ylmethyl)-8-methoxy-3-aza-bicyclo[3.2.1]oct-8-yl]-benzamide;
3-[3-(1-Hydroxy-3-phenyl-cyclobutylmethyl)-8-methoxy-3-aza-bicyclo[3.2.1]oct-8-yl]-benzamide;
N-{3-[3-(2-Ethyl-hexyl)-8-methoxy-3-aza-bicyclo[3.2.1]oct-8-yl]-phenyl}-methanesulfonamide;
N-[3-(8-Methoxy-3-octyl-3-aza-bicyclo[3.2.1]oct-8-yl)-phenyl]-methanesulfonamide;
2-Methoxy-ethanesulfonic acid [3-(3-hexyl-8-hydroxy-3-aza-bicyclo[3.2.1]oct-8-yl)-phenyl]-amide;
3-(3-Biphenyl-4-ylmethyl-8-methoxy-3-aza-bicyclo[3.2.1]oct-8-yl)-benzamide;
N-{3-[3-(2-Hydroxy-indan-2-ylmethyl)-3-aza-bicyclo(3.2.1)oct-8-yl]-phenyl}-methanesulfonamide;
N-{3-[8-Methoxy-3-(4-methoxy-benzyl)-3-aza-bicyclo[3.2.1]oct-8-yl]-phenyl}-methanesulfonamide;
2-Methoxy-ethanesulfonic acid [3-(8-hydroxy-3-pyridin-3-ylmethyl-3-aza-bicyclo[3.2.1]oct-8-yl)-phenyl]-amide;
3-[8-Methoxy-3-(3-trifluoromethoxy-benzyl)-3-aza-bicyclo[3.2.1]oct-8-yl]-benzamide;
N-{3-[3-(4-Chloro-benzyl)-8-methoxy-3-aza-bicyclo[3.2.1]oct-8-yl-phenyl}-methanesulfonamide;
2-Methoxy-ethanesulfonic acid [3-(8-hydroxy-3-thiophen-3-ylmethyl-3-aza-bicyclo[3.2.1]oct-8-yl)-phenyl]-amide;
2-Methoxy-ethanesulfonic acid [3-(3-cyclohexylmethyl-8-hydroxy-3-aza-bicyclo[3.2.1]oct-8-yl)-phenyl]-amide;
N-(3-{8-Hydroxy-3-[3-(1-hydroxy-cyclohexyl)-propyl]-3-aza-bicyclo[3.2.1]oct-8-yl}-phenyl)-methanesulfonamide;
3-[3-(9H-Fluoren-2-ylmethyl)-8-methoxy-3-aza-bicyclo[3.2.1]oct-8-yl]-benzamide;
N-{3-[3-(1H-Indol-3-ylmethyl)-8-methoxy-3-aza-bicyclo[3.2.1]oct-8-yl]-phenyl}-methanesulfonamide;
N-[3-(3-Benzofuran-2-ylmethyl-8-methoxy-3-aza-bicyclo[3.2.1]oct-8-yl)-phenyl]-methanesulfonamide;
N-{3-[3-(2-Hydroxy-1,2,3,4-tetrahydro-naphthalen-2-yl-methyl)-3-aza-bicyclo[3.2.1]oct-8-yl]-phenyl}-methanesulfonamide;
3-[8-Methoxy-3-(3-phenoxy-benzyl)-3-aza-bicyclo[3.2.1]oct-8-yl]-benzamide;
N-{3-[8-Hydroxy-3-(2-hydroxy-indan-2-ylmethyl)-3-aza-bicyclo[3.2.1]oct-8-yl]-phenyl}-methanesulfonamide;
3-[3-(4-Dimethylamino-naphthalen-1-ylmethyl)-8-methoxy-3-aza-bicyclo[3.2.1]oct-8-yl]-benzamide;
2-Methoxy-ethanesulfonic acid [3-(8-hydroxy-3-phenethyl-3-aza-bicyclo[3.2.1]oct-8-yl)-phenyl]-amide;
N-[3-(8-Methoxy-3-naphthalen-1-ylmethyl-3-aza-bicyclo[3.2.1]oct-8-yl)-phenyl]-methanesulfonamide;
N-[3-(8-Methoxy-3-naphthalen-1-ylmethyl-3-aza-bicyclo[3.2.1]oct-8-yl)-phenyl]-methanesulfonamide;
N-(3-{3-[3-(1-Hydroxy-cyclohexyl)-propyl]-8-methoxy-3-aza-bicyclo[3.2.1]oct-8-yl}-phenyl)-methanesulfonamide;
N-[3-(8-Methoxy-3-quinolin-4-ylmethyl-3-aza-bicyclo[3.2.1]oct-8-yl)-phenyl]-methanesulfonamide;
N-[3-(8-Methoxy-3-quinolin-3-ylmethyl-3-aza-bicyclo[3.2.1]oct-8-yl)-phenyl]-methanesulfonamide;
N-{3-[3-(4-Chloro-2-fluoro-benzyl)-8-methoxy-3-aza-bicyclo[3.2.1]oct-8-yl]-phenyl}-methanesulfonamide;
2-Methoxy-ethanesulfonic acid [3-(8-hydroxy-3-octyl-3-aza-bicyclo[3.2.1]oct-8-yl)-phenyl]-amide;
N-{3-[8-Methoxy-3-(1-methyl-1H-indol-3-ylmethyl)-3-aza-bicyclo[3.2.1]oct-8-yl]-phenyl}-methanesulfonamide;
2-Methoxy-ethanesulfonic acid {3-[8-hydroxy-3-(3-phenyl-prop-2-ynyl)-3-aza-bicyclo[3.2.1]oct-8-yl]-phenyl}-amide;
N-{3-[8-Hydroxy-3-(2-hydroxy-1,2,3,4-tetrahydro-naphthalen-2-ylmethyl)-3-aza-bicyclo[3.2.1]oct-8-yl-phenyl}-methanesulfonamide;
N-{3-[3-(2-Hydroxy-indan-2-ylmethyl)-8-methoxy-3-aza-bicyclo[3.2.1]oct-8-yl]-phenyl}-methanesulfonamide;
2-Methoxy-ethanesulfonic acid {3-[8-hydroxy-3-(3-phenyl-propyl)-3-aza-bicyclo[3.2.1]oct-8-yl]-phenyl}-amide;
2-Methoxy-ethanesulfonic acid {3-[3-(4-chloro-benzyl)-8-hydroxy-3-aza-bicyclo[3.2.1]oct-8-yl]-phenyl}-amide;
N-{3-[3-(4-Hydroxy-naphthalen-1-ylmethyl)-8-methoxy-3-aza-bicyclo[3.2.1]oct-8-ylJ-phenyl}-methanesulfonamide;
2-Methoxy-ethanesulfonic acid {3-[8-hydroxy-3-(1H-indol-3-ylmethyl)-3-aza-bicyclo[3.2.1]oct-8-yl]-phenyl}-amide;
N-{3-[8-Methoxy-3-(4-pyrrolidin-1-yl-benzyl)-3-aza-bicyclo[3.2.1]oct-8-yl]-phenyr}-methanesulfonamide;
N-{3-8-Methoxy-3-(3-methyl-benzo[b]thiophen-2-ylmethyl)-3-aza-bicyclo[3.2.1]oct-8-yl]-phenyl}-methanesulfonamide;
2-Methoxy-ethanesulfonic acid [3-(3-benzofuran-2-ylmethyl-8-hydroxy-3-aza-bicyclo[3.2.1]oct-8-yl)-phenyl]-amide;
N-{3-[3-(2-Hydroxy-1,2,3,4-tetrahydro-naphthalen-2-ylmethyl)-8-methoxy-3-aza-bicyclo[3.2.1]oct-8-yl]-phenyl}-methanesulfonamide;
N-[3-(3-Biphenyl-4-ylmethyl-8-methoxy-3-aza-bicyclo[3.2.1]oct-8-yl)-phenyl]-methanesulfonamide;
2-Methoxy-ethanesurfonic acid [3-(8-hydroxy-3-naphthalen-2-ylmethyl-3-aza-bicyclo[3.2.1]oct-8-yl)-phenyl]-amide;
2-Methoxy-ethanesulfonic acid [3-(8-hydroxy-3-naphthalen-1-ylmethyl-3-aza-bicyclo[3.2.1]oct-8-yl)-phenyl]-amide;

2-Methoxy-ethanesulfonic acid (3-{8-hydroxy-3-[3-(1-hydroxy-cyclohexyl)-propyl]-3-aza-bicyclo[3.2.1]oct-8-yl}-phenyl)-amide;

2-Methoxy-ethanesulfonic acid [3-(8-hydroxy-3-quinolin-4-ylmethyl-3-aza-bicyclo[3.2.1]oct-8-yl)-phenyl]-amide;

2-Methoxy-ethanesulfonic acid [3-(8-hydroxy-3-quinolin-3-ylmethyl-3-aza-bicyclo[3.2.1]oct-8-yl)-phenyl]-amide;

2-Methoxy-ethanesulfonic acid {3-[8-hydroxy-3-(1-methyl-1H-indol-3-ylmethyl)-3-aza-bicyclo[3.2.1]oct-8-yl]-phenyl}-amide;

N-{3-[8-Methoxy-3-(3-trifluoromethoxy-benzyl)-3-aza-bicyclo[3.2.1]oct-8-yl]-phenyl}-methanesulfonamide;

2-Methoxy-ethanesulfonic acid{3-[3-(2-hydroxy-1,2,3,4-tetrahydro-naphthalen-2-ylmethyl)-3-aza-bioyclo[3.2.1]oct-8-yl]-phenyl}-amide;

2-Methoxy-ethanesulfonic acid {3-[8-hydroxy-3-(2-hydroxy-indan-2-ylmethyl)-3-aza-bicyclo[3.2.1]oct-8-yl]-phenyl}-amide;

N-{3-[3-(9H-Fluoren-2-ylmethyl)-8-methoxy-3-aza-bicyclo[3.2.1]oct-8-yl]-phenyl}-methanesulfonamide;

2-Methoxy-ethanesulfonic acid {3-]8-hydroxy-3-(2-phenethyloxy-ethyl)-3-aza-bicyclo[3.2.1]oct-8-yl]-phenyl}-amide;

N-{3-[8-Methoxy-3-(3-phenoxy-benzyl)-3-aza-bicyclo[3.2.1]oct-8-yl]-phenyl}-methanesulfonamide;

N-{3-[3-(4-Dimethylamino-naphthalen-1-ylmethyl)-8-methoxy-3-aza-bicyclo[3.2.1]oct-8-yl]-phenyl}-methanesulfonamide;

2-Methoxy-ethanesulfonic acid (3-[8-hydroxy-3-(4-hydroxy-naphthalen-1-ylmethyl)-3-aza-bicyclo[3.2.1]oct-8-yl]-phenyl}-amide;

2-Methoxy-ethanesulfonic acid {3-[8-hydroxy-3-(4-pyrrolidin-1-yl-benzyl)-3-aza-bicyclo[3.2.1]oct-8-yl]-phenyl}-amide;

2-Methoxy-ethanesulfonic acid {3-[8-hydroxy-3-(3-methyl-benzo[b]thiophen-2-ylmethyl)-3-aza-bicyclo[3.2.1]oct-8-yl]-phenyl}-amide;

2-Methoxy-ethanesulfonic acid {3-[3-(2-hydroxy-1,2,3,4-tetrahydro-naphthalen-2-ylmethyl)-8-hydroxy-3-aza-bicyclo[3.2.1]oct-8-yl]-phenyl}-amide;

2-Methoxy-ethanesulfonic acid {3-[3-(2-hydroxy-indan-2-ylmethyl)-8-methoxy-3-aza-bicyclo[3.2.1]oct-8-yl]-phenyl}-amide;

2-Methoxy-ethanesulfonic acid [3-(3-biphenyl-4-ylmethyl-8-hydroxy-3-aza-bicyclo[3.2.1]oct-8-yl)-phenyl]-amide;

2-Methoxy-ethanesulfonic acid {3-[3-(2-hydroxy-1,2,3,4-tetrahydro-naphthalen-2-ylmethyl)-8-methoxy-3-aza-bicyclo[3.2.1]oct-8-yl]-phenyl}-amide;

2-Methoxy-ethanesulfonic acid {3-[3-(9H-fluoren-2-ylmethyl)-8-hydroxy-3-aza-bicyclo[3.2.1]oct-8-yl]-phenyl}-amide;

2-Methoxy-ethanesultonic acid {3-[8-hydroxy-3-(3-phenoxy-benzyl)-3-aza-bicyclo[3.2.1]oct-8-yl]-phenyl}-amide;

2-Methoxy-ethanesulfonic acid {3-[3-(4-dimethylamino-naphthalen-1-ylmethyl)-8-hydroxy-3-aza-bicyclo[3.2.1]oct-8-yl]-phenyl}-amide;

3-(3-Cyclopropylmethyl-8-hydroxy-3-aza-bicyclo[3.2.1]oct-8-yl)-phenol;

3-{3-[3-(1-Hydroxy-cyclohexyl)-propyl]-3-aza-bicyclo[3.2.1]oct-8-yl}-phenol; and 3-(3-Cyclohexyl-propyl)-8-(3-hydroxy-phenyl)-3-aza-bicyclo[3.2.1]octan-8-ol;

or pharmaceutically acceptable salts thereof.

8. A pharmaceutical composition comprising an effective amount of a compound according to claim 1 in combination with a pharmaceutically acceptable carrier, excipient or additive.

* * * * *